US008048452B2

(12) United States Patent
Curatolo et al.

(10) Patent No.: US 8,048,452 B2
(45) Date of Patent: Nov. 1, 2011

(54) PHARMACEUTICAL COMPOSITIONS OF CHOLESTERYL ESTER TRANSFER PROTEIN INHIBITOR

(75) Inventors: William J. Curatolo, Niantic, CT (US); Dwayne T. Friesen, Bend, OR (US); Michael J. Gumkowski, Old Lyme, CT (US); Douglas A. Lorenz, Bend, OR (US); James A. S. Nightingale, Bend, OR (US); Roger B. Ruggeri, Waterford, CT (US); Ravi M. Shanker, Groton, CT (US)

(73) Assignee: Bend Research, Inc., Bend, OR (US)

( * ) Notice: Subject to any disclaimer, the term of this patent is extended or adjusted under 35 U.S.C. 154(b) by 1552 days.

(21) Appl. No.: 11/421,888

(22) Filed: Jun. 2, 2006

(65) Prior Publication Data
US 2006/0211654 A1  Sep. 21, 2006

Related U.S. Application Data

(63) Continuation of application No. 09/918,127, filed on Jul. 30, 2001, now Pat. No. 7,115,279.

(60) Provisional application No. 60/223,279, filed on Aug. 3, 2000.

(51) Int. Cl.
A01N 25/34 (2006.01)
A61K 9/14 (2006.01)
A61K 9/22 (2006.01)
A61K 9/48 (2006.01)
A61K 47/32 (2006.01)
A61K 31/21 (2006.01)
A61K 31/19 (2006.01)
A61K 31/715 (2006.01)

(52) U.S. Cl. ........ 424/489; 424/468; 424/404; 424/451; 424/488; 514/772.4; 514/513; 514/557; 514/57

(58) Field of Classification Search .................. 424/468, 424/404, 451, 457, 488, 489; 514/772.4, 514/313, 513, 57, 557
See application file for complete search history.

(56) References Cited

U.S. PATENT DOCUMENTS

| | | | |
|---|---|---|---|
| 4,983,593 A | 1/1991 | Miyajima et al. | 514/110 |
| 5,093,371 A | 3/1992 | Quinn et al. | 514/682 |
| 5,340,591 A | 8/1994 | Nakano et al. | 424/499 |
| 5,446,207 A | 8/1995 | Pomponi et al. | 568/633 |
| 5,456,923 A | 10/1995 | Nakamichi et al. | 424/489 |
| 5,474,993 A | 12/1995 | Rubin et al. | 514/192 |
| 5,714,506 A | 2/1998 | Fisher et al. | 514/352 |
| 5,880,095 A | 3/1999 | Park et al. | 514/12 |
| 5,932,587 A | 8/1999 | Schmeck et al. | 514/278 |
| 5,942,631 A | 8/1999 | Deck et al. | 549/294 |
| 6,069,148 A | 5/2000 | Schmidt et al. | 514/277 |
| 6,140,342 A | 10/2000 | Goldstein et al. | 514/313 |
| 6,140,343 A | 10/2000 | DeNinno et al. | 514/313 |
| 6,147,089 A | 11/2000 | DeNinno et al. | 514/313 |
| 6,147,090 A | 11/2000 | DeNinno et al. | 514/313 |
| 6,177,101 B1 | 1/2001 | Martino et al. | 424/464 |
| 6,197,786 B1 | 3/2001 | DeNinno et al. | 514/313 |
| 6,310,075 B1 | 10/2001 | DeNinno et al. | 514/313 |
| 6,426,365 B1 * | 7/2002 | Shinkai et al. | 514/513 |
| 6,462,093 B1 | 10/2002 | Miyamoto et al. | 514/772.3 |
| 6,586,448 B1 | 7/2003 | DeNinno et al. | 514/313 |
| 6,706,283 B1 * | 3/2004 | Appel et al. | 424/473 |
| 6,763,607 B2 | 7/2004 | Beyerinck et al. | 34/372 |
| 6,906,082 B2 | 6/2005 | DeNinno et al. | 514/313 |
| 2001/0018446 A1 | 8/2001 | Sikorski et al. | 514/357 |
| 2001/0028895 A1 | 10/2001 | Bisgaier et al. | 424/450 |
| 2002/0009494 A1 | 1/2002 | Curatolo et al. | 424/489 |
| 2002/0015731 A1 * | 2/2002 | Appel et al. | 424/473 |
| 2003/0054038 A1 | 3/2003 | Crew et al. | 424/486 |
| 2003/0091643 A1 | 5/2003 | Friesen et al. | 424/486 |
| 2003/0092708 A1 | 5/2003 | Shinkai et al. | 514/227.5 |
| 2003/0170309 A1 | 9/2003 | Babcock et al. | 424/486 |
| 2004/0013734 A1 | 1/2004 | Babcock et al. | 424/488 |

FOREIGN PATENT DOCUMENTS

| | | | |
|---|---|---|---|
| EP | 0344603 | | 10/1991 |
| EP | 0580860 | | 10/1997 |
| EP | 0801060 | | 10/1997 |
| EP | 0901786 | | 3/1999 |
| EP | 0796846 | | 7/2000 |
| EP | 1020439 | | 7/2000 |
| EP | 1160330 | | 12/2001 |
| EP | 0818197 | | 11/2003 |
| EP | 0818448 | | 11/2003 |
| EP | 1114032 | | 6/2004 |
| EP | 1114031 | | 6/2005 |
| EP | 0992496 | | 8/2005 |
| GB | 2305665 | | 4/1997 |
| JP | 10287662 | | 10/1998 |
| WO | WO 9619239 | | 6/1996 |
| WO | WO 9804528 | | 2/1998 |
| WO | WO 98/35937 | * | 8/1998 |
| WO | WO 9839299 | | 9/1998 |
| WO | WO 99/14204 | * | 3/1999 |
| WO | WO 9914174 | | 3/1999 |
| WO | WO 9914204 | | 3/1999 |
| WO | WO 9914215 | | 3/1999 |
| WO | WO 9941237 | | 8/1999 |
| WO | WO 0017164 | | 3/2000 |
| WO | WO 0018721 | | 4/2000 |
| WO | WO 0018723 | | 4/2000 |
| WO | WO 0018724 | | 4/2000 |
| WO | WO 0072825 | | 12/2000 |
| WO | WO 0140190 | | 6/2001 |
| WO | WO 0211710 | | 2/2002 |

OTHER PUBLICATIONS

Gordon et al., Circulation, 1989, 79, pp. 8-15.
Kitahara et al., Japan. Journ. Pharmacol., vol. 69, issue 2, pp. 101-109, 1995.

(Continued)

Primary Examiner — Blessing Fubara
(74) Attorney, Agent, or Firm — Chernoff, Vilhauer, McClung & Stenzel

(57) ABSTRACT

A pharmaceutical composition comprises a solid amorphous dispersion of a cholesteryl ester transfer protein inhibitor and a concentration-enhancing polymer.

15 Claims, No Drawings

OTHER PUBLICATIONS

Toyoda et al., Japan. Journ. Pharmacol. vol. 103m, issue 5, pp. 231-239, 1994.

Martin et al., Physical Pharmacy, 2 ed., p. 85.

Bisgaler et al., Lipids, vol. 29, No. 12, pp. 811-818, 1994.

* cited by examiner

PHARMACEUTICAL COMPOSITIONS OF CHOLESTERYL ESTER TRANSFER PROTEIN INHIBITOR

CROSS REFERENCE TO RELATED APPLICATIONS

This application is a continuation of U.S. patent application Ser. No. 09/918,127 filed Jul. 30, 2001 now U.S. Pat. No. 7,115,279, which claims priority from U.S. Provisional Application No. 60/223,279 filed Aug. 3, 2000.

BACKGROUND OF THE INVENTION

This invention relates to cholesteryl ester transfer protein (CETP) inhibitors, pharmaceutical compositions containing such inhibitors and the use of such inhibitors to elevate certain plasma lipid levels, including high density lipoprotein (HDL)-cholesterol and to lower certain other plasma lipid levels, such as low density lipoprotein (LDL)-cholesterol and triglycerides and accordingly to treat diseases which are affected by low levels of HDL cholesterol and/or high levels of LDL-cholesterol and triglycerides, such as atherosclerosis and cardiovascular diseases in certain mammals (i.e., those which have CETP in their plasma), including humans.

CETP inhibitors, particularly those that have high binding activity, are generally hydrophobic, have extremely low aqueous solubility and have low oral bioavailability when dosed conventionally. Such compounds have generally proven to be difficult to formulate for oral administration such that high bioavailabilities are achieved.

Atherosclerosis and its associated coronary artery disease (CAD) is the leading cause of death in the industrialized world. Despite attempts to modify secondary risk factors (smoking, obesity, lack of exercise) and treatment of dyslipidemia with dietary modification and drug therapy, coronary heart disease (CHD) remains the most common cause of death in the U.S., where cardiovascular disease accounts for 44% of all deaths, with 53% of these associated with atherosclerotic coronary heart disease.

Risk for development of this condition has been shown to be strongly correlated with certain plasma lipid levels. While elevated LDL-cholesterol may be the most recognized form of dyslipidemia, it is by no means the only significant lipid associated contributor to CHD. Low HDL-cholesterol is also a known risk factor for CHD (Gordon, D. J., et al.,: "High-density Lipoprotein Cholesterol and Cardiovascular Disease", Circulation, (1989), 79: 8-15).

High LDL-cholesterol and triglyceride levels are positively correlated, while high levels of HDL-cholesterol are negatively correlated with the risk for developing cardiovascular diseases. Thus, dyslipidemia is not a unitary risk profile for CHD but may be comprised of one or more lipid aberrations.

Among the many factors controlling plasma levels of these disease dependent principles, cholesteryl ester transfer protein (CETP) activity affects all three. The role of this 70,000 dalton plasma glycoprotein found in a number of animal species, including humans, is to transfer cholesteryl ester and triglyceride between lipoprotein particles, including high density lipoproteins (HDL), low density lipoproteins (LDL), very low density lipoproteins (VLDL), and chylomicrons. The net result of CETP activity is a lowering of HDL cholesterol and an increase in LDL cholesterol. This effect on lipoprotein profile is believed to be pro-atherogenic, especially in subjects whose lipid profile constitutes an increased risk for CHD.

No wholly satisfactory HDL-elevating therapies exist. Niacin can significantly increase HDL, but has serious toleration issues which reduce compliance. Fibrates and the HMG CoA reductase inhibitors raise HDL-cholesterol only modestly (~10-12%). As a result, there is a significant unmet medical need for a well-tolerated agent which can significantly elevate plasma HDL levels, thereby reversing or slowing the progression of atherosclerosis.

CETP inhibitors have been developed which inhibit CETP activity, and thus, if present in the blood, should result in higher HDL cholesterol levels and lower LDL cholesterol levels. To be effective, such CETP inhibitors must be absorbed into the blood. Oral dosing of CETP inhibitors is preferred because to be effective such CETP inhibitors must be taken on a regular basis, such as daily. Therefore, it is preferred that patients be able to take CETP inhibitors by oral dosing rather than by injection.

However, it has proven to be difficult to formulate CETP inhibitors for oral administration such that therapeutic blood levels are achieved. CETP inhibitors in general possess a number of characteristics which render them poorly bioavailable when dosed orally in a conventional manner. CETP inhibitors tend to be quite hydrophobic and extremely water insoluble, with solubility in aqueous solution of usually less than about 10 µg/ml and typically less than 1 µg/ml. Often, the aqueous solubility of CETP inhibitors is less than 0.1 µg/ml. Indeed, the solubility of some CETP inhibitors is so low that it is in fact difficult to measure. Accordingly, when CETP inhibitors are dosed orally, concentrations of CETP inhibitor in the aqueous environment of the gastrointestinal tract tend to be extremely low, resulting in poor absorption from the GI tract to blood. The hydrophobicity of CETP inhibitors not only leads to low equilibrium aqueous solubility but also tends to make the drugs poorly wetting and slow to dissolve, further reducing their tendency to dissolve and be absorbed from the gastrointestinal tract. This combination of characteristics has resulted in the bioavailability for orally dosed conventional crystalline or amorphous forms of CETP inhibitors generally to be quite low, often having absolute bioavailabilities of less than 1%.

Various attempts have been made to improve the aqueous concentration of CETP inhibitors, but generally have met with limited success. At the outset, most methods aimed at enhancing aqueous concentration and bioavailability of low-solubility drugs only offer moderate improvements. Such improvements generally lead to enhancements in aqueous concentration on the order of from one to seven fold. In addition, the enhancement may be short-lived, with the drug concentration returning to the equilibrium concentration within 10 to 40 minutes. Such small, short-lived concentration enhancements have led to even lower levels of bioavailability enhancement when tested in vivo via oral administration. Thus, when conventional dosage forms of low-solubility drugs are tested in viva via oral administration, bioavailability enhancements are typically on the order of 2-fold to 4-fold or less. For CETP inhibitors having low absolute bioavailabilities, such small improvements are insufficient to allow convenient oral dosing of CETP inhibitors; that is, dosage forms having a convenient size and frequency of dosing.

Moreover, some standard methods for improving the concentration of pharmaceuticals in aqueous solution have proven inadequate when applied to CETP inhibitors. For example, even pre-dissolving the CETP inhibitor in a water miscible solvent such as polyethylene glycol followed by delivery as a solution to an aqueous environment of use has failed to raise the aqueous concentration of CETP inhibitor to an acceptable level.

Sikorski, et al., WO 99/14204, and Lee, et al., WO 99/41237, both disclose CETP inhibitors formulated for oral administration using hydroxy propyl methyl celluose in a controlled release dosage form which is characterized as a "dispersion." Both Sikorski and Lee appear to be using the term "dispersion" to mean a controlled release matrix in which drug particles are distributed within a polymer matrix that slowly erodes rather than a solid amorphous dispersion of the type of the present invention. Such controlled release matrix compositions would slow rather than enhance the dissolution and absorption of CETP inhibitor. In any event, both Sikorski and Lee state that CETP inhibitors may be orally dosed by simply dissolving the CETP inhibitor in water without any discussion of the difficulty of dissolving the CETP inhibitors in water. There is no recognition in either Sikorski or Lee of the need to improve the aqueous concentration or bioavailability of CETP inhibitors.

Curatolo et al., EP 0 901 786 A2 disclose solid pharmaceutical dispersions with enhanced bioavailability using spray dried dispersions of a sparingly soluble drug and hydroxy propyl methyl cellulose acetate succinate. However, Curatolo et al. do not disclose the use of CETP inhibitors, or discuss the problems associated with the formulation of CETP inhibitors for oral administration.

Nakamichi et al., U.S. Pat. No. 5,456,923 disclose a process for producing solid dispersions of sparingly soluble drugs and a variety of polymeric materials, such as hydroxy propyl methyl cellulose acetate succinate. However, Nakamichi et al. does not disclose dispersions containing CETP inhibitors, much less discuss the problems associated with formulating hydrophobic drugs.

Accordingly, there is still a need for developing compositions of CETP inhibitors that may be orally dosed, that improve the aqueous concentration of such drugs, that improve the bioavailability of such drugs relative to compositions of the drugs alone, and that does not adversely affect the ability of the drugs to act therapeutically.

BRIEF SUMMARY OF INVENTION

The present invention overcomes the drawbacks of the prior art by providing in a first aspect a pharmaceutical composition comprising a solid amorphous dispersion of CETP inhibitor and a concentration-enhancing polymer.

In a second aspect of the invention, a pharmaceutical composition comprises a solid amorphous dispersion of CETP inhibitor and a concentration-enhancing polymer, the CETP inhibitor having a solubility of less than about 10 µg/ml in aqueous solution at any pH of from 1 to 8 in the absence of the concentration-enhancing polymer.

In a third aspect of the invention, a pharmaceutical composition comprises a solid amorphous dispersion of a CETP inhibitor and a concentration-enhancing polymer, the composition providing a maximum concentration of the CETP inhibitor in a use environment that is at least about 10-fold the maximum concentration provided by a control composition comprising an equivalent amount of the CETP inhibitor and free from the polymer. As used herein, a "use environment" can be either the in vivo environment of the GI tract of a mammal, particularly a human, or the in vitro environment of a test solution, such as phosphate buffered saline (PBS) or Model Fasted Duodenal (MFD) solution.

In a fourth aspect of the invention, a pharmaceutical composition comprises a solid amorphous dispersion of a CETP inhibitor and a concentration-enhancing polymer, the composition providing a relative oral bioavailability that is at least about 4 relative to a control composition comprising an equivalent amount of the CETP inhibitor and free from the polymer.

In a fifth aspect of the invention, a method is provided for treating atherosclerosis, peripheral vascular disease, dyslipidemia, hyperbetalipoproteinemia, hypoalphalipoproteinemia, hypercholesterolemia, hypertriglyceridemia, familial-hypercholestcrolemia, cardiovascular disorders, angina, ischemia, cardiac ischemia, stroke, myocardial infarction, reperfusion injury, angioplastic restenosis, hypertension, vascular complications of diabetes, obesity or endotoxemia in a mammal (including a human being, either male or female) by administering to a mammal in need of such treatment a composition of the present invention comprised of a CETP inhibitor and concentration-enhancing polymer.

The composition may be dosed in a variety of dosage forms, including both immediate release and controlled release dosage forms, the latter including both delayed and sustained release forms. The composition may include blends of polymers, and may further include other polymers that improve the aqueous concentration of the CETP inhibitor.

The various aspects of the present invention each provide one or more of the following advantages. The compositions of the present invention improve the aqueous concentration of CETP inhibitors relative to compositions that are free from concentration-enhancing polymer, by providing aqueous concentration of CETP inhibitors of at least about 10-fold that of control compositions that are free from the concentration-enhancing polymer. Such solubility enhancements are unexpectedly large relative to that typically observed for dispersions of other types of drugs. Accordingly, the compositions of the present invention comprising a CETP inhibitor and concentration-enhancing polymer allow the dose of CETP inhibitor required to obtain adequate efficacy to be reduced.

In fact, compositions of the present invention often exhibit surprisingly large enhancements for some CETP inhibitors, on the order of 50 to 500-fold and in some cases up to a 80,000-fold improvement in concentration relative to that of a control crystalline composition. Such large enhancements are, for some CETP inhibitors, necessary for convenient oral administration. The compositions thus render hydrophobic, substantially insoluble CETP inhibitors therapeutically effective with a convenient dose (mass of drug) for oral administration.

The foregoing and other objectives, features, and advantages of the invention will be more readily understood upon consideration of the following detailed description of the invention.

DETAILED DESCRIPTION OF THE INVENTION

The present invention provides compositions of CETP inhibitors and at least one concentration-enhancing polymer. As discussed above in the Background, CETP inhibitors generally have (1) extremely low solubilities in aqueous solution (i.e., less than about 10 µg/mL) at physiologically relevant pH (e.g., any pH of from 1 through 8) measured at about 22° C.; (2) a relatively hydrophobic nature; and (3) a relatively low bioavailability when orally dosed in the crystalline state. Accordingly, CETP inhibitors require some kind of modification or formulation to enhance their solubility and thereby achieve good bioavailability. Surprisingly, the compositions of the present invention provide unusually large enhancements in aqueous concentration in an environment of use and unusually large enhancements in bioavailability compared with other conventional compositions used to formulate poorly soluble, hydrophobic drugs. The inventors have found that, contrary to conventional wisdom, the compositions provide the greatest enhancements for those drugs which have been thought most difficult to formulate for oral delivery. Specifically, the inventors have found that preparing CETP inhibitors as compositions comprising a solid amorphous dispersion of a CETP inhibitor and concentration-enhancing polymer, and preferably as a homogenous dispersion, improves the aqueous concentration of the CETP inhibitors as well as relative bioavailability. The compositions, CETP inhibitors, suitable polymers, and optional excipients are discussed in more detail as follows.

Compositions of CETP Inhibitors and Concentration-Enhancing Polymer

The present invention finds utility with any low-solubility CETP inhibitor, or any CETP inhibitor which would benefit by improved bioavailability or more rapid absorption. The compositions of the present invention comprise dispersions of a CETP inhibitor and at least one concentration-enhancing polymer. The CETP inhibitor in its pure state may be crystalline or amorphous. Preferably, at least a major portion of the CETP inhibitor in the composition is amorphous. By "amorphous" is meant simply that the CETP inhibitor is in a non-crystalline state. As used herein, the term "a major portion" of the CETP inhibitor means that at least 60% of the CETP inhibitor in the composition is in the amorphous form, rather than the crystalline form. Preferably, the CETP inhibitor in the dispersion is substantially amorphous. As used herein, "substantially amorphous" means that the amount of the CETP inhibitor in crystalline form does not exceed about 25%. More preferably, the CETP inhibitor in the dispersion is "almost completely amorphous" meaning that the amount of CETP inhibitor in the crystalline form does not exceed about 10%. Amounts of crystalline CETP inhibitor may be measured by powder X-ray diffraction, Scanning Electron Microscope (SEM) analysis, differential scanning calorimetry (DSC), or any other standard quantitative measurement.

The composition may contain from about 1 to about 80 wt % CETP inhibitor, depending on the dose of the CETP inhibitor and the effectiveness of the concentration-enhancing polymer. Enhancement of aqueous CETP inhibitor concentrations and relative bioavailability are typically best at low CETP inhibitor levels, typically less than about 25 to 40 wt %. However, due to the practical limit of the dosage form size, higher CETP inhibitor levels are often preferred and in many cases perform well.

The amorphous CETP inhibitor can exist within the solid amorphous dispersion as a pure phase, as a solid solution of CETP inhibitor homogeneously distributed throughout the polymer or any combination of these states or those states that lie intermediate between them. The dispersion is preferably substantially homogeneous so that the amorphous CETP inhibitor is dispersed as homogeneously as possible throughout the polymer. As used herein, "substantially homogeneous" means that the fraction of CETP inhibitor that is present in relatively pure amorphous domains within the solid dispersion is relatively small, on the order of less than 20%, and preferably less than 10% of the total amount of CETP inhibitor.

While the dispersion may have some CETP inhibitor-rich domains, it is preferred that the dispersion itself have a single glass transition temperature ($T_g$) which demonstrates that the dispersion is substantially homogeneous. This contrasts with a simple physical mixture of pure amorphous CETP inhibitor particles and pure amorphous polymer particles which generally display two distinct $T_g$s, one that of the CETP inhibitor and one that of the polymer. $T_g$ as used herein is the characteristic temperature where a glassy material, upon gradual heating, undergoes a relatively rapid (e.g., 10 to 100 seconds) physical change from a glass state to a rubber state. The $T_g$ of an amorphous material such as a polymer, drug or dispersion can be measured by several techniques, including by a dynamic mechanical analyzer (DMA), a dilatometer, dielectric analyzer, and by a differential scanning calorimeter (DSC). The exact values measured by each technique can vary somewhat but usually fall within 10° to 30° C. of each other. Regardless of the technique used, when an amorphous dispersion exhibits a single $T_g$, this indicates that the dispersion is substantially homogenous. Dispersions of the present invention that are substantially homogeneous generally are more physically stable and have improved concentration-enhancing properties and, in turn improved bioavailability, relative to nonhomogeneous dispersions.

The compositions comprising the CETP inhibitor and concentration-enhancing polymer provide enhanced concentration of the dissolved CETP inhibitor in in vitro dissolution tests. It has been determined that enhanced drug concentration in in vitro dissolution tests in Model Fasted Duodenal (MFD) solution or Phosphate Buffered Saline (PBS) is a good indicator of in vivo performance and bioavailability. An appropriate PBS solution is an aqueous solution comprising 20 mM sodium phosphate ($Na_2HPO_4$), 47 mM potassium phosphate ($KH_2PO_4$), 87 mM NaCl, and 0.2 mM KCl, adjusted to pH 6.5 with NaOH. An appropriate MFD solution is the same PBS solution wherein additionally is present 7.3 mM sodium taurocholic acid and 1.4 mM of 1-palmitoyl-2-oleyl-sn-glycero-3-phosphocholine. In particular, a composition of the present invention can be dissolution-tested by adding it to MFD or PBS solution and agitating to promote dissolution. Generally, the amount of composition added to the solution in such a test is an amount that, if all the drug in the composition dissolved, would produce a CETP inhibitor concentration that is at least about 10-fold and preferably at least 100-fold the equilibrium solubility of the CETP inhibitor alone in the test solution. To demonstrate even higher levels of dissolved CETP inhibitor concentration, addition of even larger amounts of the composition is desirable.

In one aspect, the compositions of the present invention provide a Maximum Drug Concentration (MDC) that is at least about 10-fold the equilibrium concentration of a control composition comprising an equivalent quantity of CETP inhibitor but free from the polymer. In other words, if the equilibrium concentration provided by the control composition is 1 μg/mL, then a composition of the present invention provides an MDC of at least about 10 μg/mL. The comparison composition is conventionally the undispersed CETP inhibitor alone (e.g., typically, the crystalline CETP inhibitor alone in its most thermodynamically stable crystalline form, or in cases where a crystalline form of the CETP inhibitor is unknown, the control may be the amorphous CETP inhibitor alone) or the CETP inhibitor plus a weight of inert diluent equivalent to the weight of polymer in the test composition. Preferably, the MDC of CETP inhibitor achieved with the compositions of the present invention is at least about 50-fold, more preferably at least about 200-fold and even more preferably at least about 500-fold, the equilibrium concentration of the control composition. Surprisingly, the present invention may achieve extremely large enhancements in aqueous concentration. In some cases, the MDC of CETP inhibitor provided by the compositions of the present invention are 200-fold to more than 1000-fold the equilibrium concentration of the control composition. For some CETP inhibitors, due to their extremely low aqueous solubilities, such large enhancements are required in order for the inhibitors to be sufficiently bioavailable when orally dosed.

Alternatively, the compositions of the present invention provide in an aqueous use environment a concentration versus time Area Under The Curve (AUC), for any period of at least 90 minutes between the time of introduction into the use environment and about 270 minutes following introduction to the use environment, that is at least 5-fold that of a control composition comprising an equivalent quantity of undispersed CETP inhibitor. Preferably, the compositions of the present invention provide in an aqueous use environment a concentration versus time AUC, for any period of at least 90 minutes between the time of introduction into the use environment and about 270 minutes following introduction to the use environment, that is at least about 25-fold, more preferably at least about 100-fold and even more preferably at least about 250-fold that of a control composition as described above. Such large enhancements in aqueous concentration versus time AUC values are surprising given the extremely low aqueous solubility and hydrophobicity of most CETP inhibitors.

A typical in vitro test to evaluate enhanced drug concentration in aqueous solution can be conducted by (1) adding with agitation a sufficient quantity of control composition, typically the CETP inhibitor alone, to the in vitro test medium, typically MFD or PBS solution, to achieve equilibrium concentration of the CETP inhibitor; (2) adding with agitation a sufficient quantity of test composition (e.g., the CETP inhibitor and polymer) in an equivalent test medium, such that if all the CETP inhibitor dissolved, the theoretical concentration of CETP inhibitor would exceed the equilibrium concentration of the CETP inhibitor by a factor of at least 10, and preferably a factor of at least 100; and (3) comparing the measured MDC and/or aqueous concentration versus time AUC of the test composition in the test medium with the equilibrium concentration, and/or the aqueous concentration versus time AUC of the control composition. In conducting such a dissolution test, the amount of test composition or control composition used is an amount such that if all of the CETP inhibitor dissolved the CETP inhibitor concentration would be at least 10-fold and preferably at least 100-fold that of the equilibrium concentration. Indeed, for some extremely insoluble CETP inhibitors, in order to identify the MDC achieved it may be necessary to use an amount of test composition such that if all of the CETP inhibitor dissolved, the CETP inhibitor concentration would be 10,000-fold or even more, that of the equilibrium concentration of the CETP inhibitor.

The concentration of dissolved CETP inhibitor is typically measured as a function of time by sampling the test medium and plotting CETP inhibitor concentration in the test medium vs. time so that the MDC can be ascertained. The MDC is taken to be the maximum value of dissolved CETP inhibitor measured over the duration of the test. The aqueous concentration of the CETP inhibitor versus time AUC is calculated by integrating the concentration versus time curve over any 90-minute time period between the time of introduction of the composition into the aqueous use environment (time equals zero) and 270 minutes following introduction to the use environment (time equals 270 minutes). Typically, when the composition reaches its MDC rapidly, less than about 30 minutes, the time interval used to calculate AUC is from time equals zero to time equals 90 minutes. However, if the AUC over any 90-minute time period described above of a composition meets the criterion of this invention, then the composition is a part of this invention.

To avoid large CETP inhibitor particulates which would give an erroneous determination, the test solution is either filtered or centrifuged. "Dissolved CETP inhibitor" is typically taken as that material that either passes a 0.45 µm syringe filter or, alternatively, the material that remains in the supernatant following centrifugation. Filtration can be conducted using a 13 mm, 0.45 µm polyvinylidine difluoride syringe filter sold by Scientific Resources under the trademark TITAN®. Centrifugation is typically carried out in a polypropylene microcentrifuge tube by centrifuging at 13,000 G for 60 seconds. Other similar filtration or centrifugation methods can be employed and useful results obtained. For example, using other types of microfilters may yield values somewhat higher or lower (±10-40%) than that obtained with the filter specified above but will still allow identification of preferred dispersions. It is recognized that this definition of dissolved CETP inhibitors encompasses not only monomeric solvated CETP inhibitor molecules but also a wide range of species such as polymer/CETP inhibitor assemblies that have submicron dimensions such as CETP inhibitor aggregates, aggregates of mixtures of polymer and CETP inhibitor, micelles, polymeric micelles, colloidal particles or nanocrystals, polymer/CETP inhibitor complexes, and other such CETP inhibitor-containing species that are present in the filtrate or supernatant in the specified dissolution test.

Alternatively, the compositions of the present invention, when dosed orally to a human or other animal, provide an AUC in CETP inhibitor concentration in the blood that is at least about 4-fold that observed when a control composition comprising an equivalent quantity of undispersed drug is dosed. It is noted that such compositions can also be said to have a relative bioavailability of about 4. Preferably, the compositions of the present invention, when dosed orally to a human or other animal, provide an AUC in CETP inhibitor concentration in the blood that is at least about 6-fold, more preferably at least about 10-fold, and even more preferably at least about 20-fold that observed when a control composition comprising an equivalent quantity of undispersed drug is dosed. Thus, the compositions of the present invention can be evaluated in either in vitro or in vivo tests, or both.

Relative bioavailability of CETP inhibitors in the dispersions of the present invention can be tested in vivo in animals or humans using conventional methods for making such a determination. An in vivo test, such as a crossover study, may be used to determine whether a composition of CETP inhibitor and concentration-enhancing polymer provides an enhanced relative bioavailability compared with a control composition comprised of a CETP inhibitor but no polymer as described above. In an in vivo crossover study a "test composition" of CETP inhibitor and polymer is dosed to half a group of test subjects and, after an appropriate washout period (e.g., one week) the same subjects are dosed with a "control composition" that comprises an equivalent quantity of CETP inhibitor as the "test composition" (but with no polymer present). The other half of the group is dosed with the control composition first, followed by the test composition. The relative bioavailability is measured as the concentration in the blood (serum or plasma) versus time area under the curve (AUC) determined for the test group divided by the AUC in the blood provided by the control composition. Preferably, this test/control ratio is determined for each subject, and then the ratios are averaged over all subjects in the study. In vivo determinations of AUC can be made by plotting the serum or plasma concentration of drug along the ordinate (y-axis) against time along the abscissa (x-axis).

Thus, as noted above, one embodiment of the present invention is one in which the relative bioavailability of the test composition is at least about 4 relative to a control composition comprised of a CETP inhibitor but with no polymer as described above. (That is, the in vivo AUC provided by the test composition is at least about 4-fold the in vivo AUC provided by the control composition.) A preferred embodiment of the invention is one in which the relative bioavailability of the test composition is at least about 6, and even more preferably at least about 10 relative to a control composition composed of the CETP inhibitor but with no polymer present, as described above. The determination of AUCs is a well-known procedure and is described, for example, in Welling, "Pharmacokinetics Processes and Mathematics," ACS Monograph 185 (1986).

The compositions of the present invention have particular utility when the "absolute bioavailability" of the CETP inhibitor is less than about 5%, and preferably less than about 1%. By "absolute bioavailability" is meant the ratio of the area under the blood plasma or serum drug concentration versus time curve for oral dosing of a test composition to that obtained by intravenous dosing of a solution of the CETP inhibitor (or the lowest-energy amorphous form of the CETP inhibitor where a crystalline form is unknown). Care must be taken when determining the absolute bioavailability of CETP inhibitors because their low solubility can result in precipitation of the crystalline form when dosed intravenously, leading to an inaccurate calculation of absolute bioavailability. For CETP inhibitors with such absolute bioavailabilities less than about 5%, the compositions of the present invention preferably provide a relative bioavailability that is at least about 6-fold relative to a control composition comprised of the CETP inhibitor but with no polymer present, as described above. More preferably, when the absolute bioavailability of the CETP inhibitor is less than about 1%, the compositions of the present invention provide relative bioavailability that is at least about 10-fold, and even more preferably at least about 20-fold relative to a control composition, as described above.

Cholesteryl Ester Transfer Protein Inhibitors

The invention is useful for CETP inhibitors which have sufficiently low aqueous solubility, low bioavailability or slow rate of absorption such that it is desirable to increase their concentration in an aqueous environment of use. Therefore, anytime one finds it desirable to raise the aqueous concentration of the CETP inhibitor in a use environment, the invention will find utility. The CETP inhibitor is "substantially water-insoluble" which means that the CETP inhibitor has a minimum aqueous solubility of less than about 0.01 mg/mL (or 10 μg/ml) at any physiologically relevant pH (e.g., pH 1-8) and at about 22° C. (Unless otherwise specified, reference to aqueous solubility herein and in the claims is determined at about 22° C.) Compositions of the present invention find greater utility as the solubility of the CETP inhibitors decreases, and thus are preferred for CETP inhibitors with solubilities less than about 2 μg/mL, and even more preferred for CETP inhibitors with solubilities less than about 0.5 μg/mL. Many CETP inhibitors have even lower solubilities (some even less than 0.1 μg/mL), and require dramatic concentration enhancement to be sufficiently bioavailable upon oral dosing for effective plasma concentrations to be reached at practical doses.

In general, it may be said that the CETP inhibitor has a dose-to-aqueous solubility ratio greater than about 100 mL, where the solubility (mg/mL) is the minimum value observed in any physiologically relevant aqueous solution (e.g., those with pH values from 1 to 8) including USP simulated gastric and intestinal buffers, and dose is in mg. Compositions of the present invention, as mentioned above, find greater utility as the solubility of the CETP inhibitor decreases and the dose increases. Thus, the compositions are preferred as the dose-to-solubility ratio increases, and thus are preferred for dose-to-solubility ratios greater than 1000 mL, and more preferred for dose-to-solubility ratios greater than about 5000 ml.

Oral delivery of many CETP inhibitors is particularly difficult because their aqueous solubility is usually extremely low, typically being less than 2 μg/ml, often being less than 0.1 μg/ml. Such low solubilities are a direct consequence of the particular structural characteristics of species that bind to CETP and thus act as CETP inhibitors. This low solubility is primarily due to the hydrophobic nature of CETP inhibitors. Clog P, defined as the base 10 logarithm of the ratio of the drug solubility in octanol to the drug solubility in water, is a widely accepted measure of hydrophobicity. In general, Clog P values for CETP inhibitors are greater than 4 and are often greater than 5 to 7. Thus, the hydrophobic and insoluble nature of CETP inhibitors as a class pose a particular challenge for oral delivery. Achieving therapeutic drug levels in the blood by oral dosing of practical quantities of drug generally requires a large enhancement in drug concentrations in the gastrointestinal fluid and a resulting large enhancement in bioavailability. Such enhancements in drug concentration in gastrointestinal fluid typically need to be at least about 10-fold and often at least about 50-fold or even at least about 200-fold to achieve desired blood levels. Surprisingly, the dispersions of the present invention have proven to have the required large enhancements in drug concentration and bioavailability.

In contrast to conventional wisdom, the relative degree of enhancement in aqueous concentration and bioavailability generally improves for CETP inhibitors as solubility decreases and hydrophobicity increases. In fact, the inventors have recognized a subclass of these CETP inhibitors that are essentially aqueous insoluble, highly hydrophobic, and are characterized by a set of physical properties. This subclass exhibits dramatic enhancements in aqueous concentration and bioavailability when formulated using the compositions of the present invention.

The first property of this subclass of essentially insoluble, hydrophobic CETP inhibitors is extremely low aqueous solubility. By extremely low aqueous solubility is meant that the minimum aqueous solubility at physiologically relevant pH (pH of 1 to 8) is less than about 10 μg/ml and preferably less than about 1 μg/ml.

A second property is a very high does-to-solubility ratio. Extremely low solubility often leads to poor or slow absorption of the drug from the fluid of the gastrointestinal tract, when the drug is dosed orally in a conventional manner. For extremely low solubility drugs, poor absorption generally becomes progressively more difficult as the dose (mass of drug given orally) increases. Thus, a second property of this subclass of essentially insoluble, hydrophobic CETP inhibitors is a very high dose (in mg) to solubility (in mg/ml) ratio (ml). By "very high dose-to-solubility ratio" is meant that the dose-to-solubility ratio has a value of at least 1000 ml, and preferably at least 5,000 ml, and more preferably at least 10,000 ml.

A third property of this subclass of essentially insoluble, hydrophobic CETP inhibitors is that they are extremely hydrophobic. By extremely hydrophobic is meant that the Clog P value of the drug, has a value of at least 4.0, preferably a value of at least 5.0, and more preferably a value of at least 5.5.

A fourth property of this subclass of essentially insoluble CETP inhibitors is that they have a low melting point. Generally, drugs of this subclass will have a melting point of about 150° C. or less, and preferably about 140° C. or less.

Primarily, as a consequence of some or all of these four properties, CETP inhibitors of this subclass typically have very low absolute bioavailabilities. Specifically, the absolute bioavailability of drugs in this subclass when dosed orally in their undispersed state is less than about 10% and more often less than about 5%.

For this subclass of CETP inhibitors, the CETP inhibitor, when dispersed in the dispersion, should be at least substantially amorphous, and more preferably is almost completely amorphous. In addition, the dispersion should be substantially homogeneous. As discussed below, such dispersions may be made by solvent processing, and preferably by spray-drying. When prepared in this fashion, this class of essentially insoluble, hydrophobic CETP inhibitors often exhibits dramatic enhancements in aqueous concentration in the use environment and in bioavailability when dosed orally. While the degree of enhancement will depend on the particular concentration-enhancing polymer, when preferred concentration-enhancing polymers are used (as discussed below), such compositions may provide a MDC in an aqueous use environment that is at least about 50-fold, and preferably at least about 200-fold, the equilibrium concentration of a control composition comprising an equivalent quantity of the essentially insoluble, hydrophobic CETP inhibitor but free from the concentration-enhancing polymer. Likewise, the compositions also display in an aqueous use environment an AUC, for any period of at least 90 minutes between the time of introduction into the use environment and about 270 minutes following introduction into the use environment that is at least about 25-fold, and preferably at least about 100-fold, that of the control composition comprising an equivalent quantity of drug but free from the concentration-enhancing polymer.

Turning now to the chemical structures of specific CETP inhibitors, one class of CETP inhibitors that finds utility with the present invention consists of oxy substituted 4-carboxyamino-2-methyl-1,2,3,4-tetrahydroquinolines having the Formula I

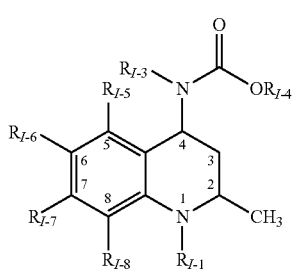

Formula I and pharmaceutically acceptable salts, enantiomers, or stereoisomers of said compounds;
wherein $R_{I-1}$ is hydrogen, $Y_I$, $W_I$—$X_I$, $W_I$—$Y_I$;
wherein $W_I$ is a carbonyl, thiocarbonyl, sulfinyl or sulfonyl;
$X_I$ is —O—$Y_I$, —S—$Y_I$, —N(H)—$Y_I$ or —N—$(Y_I)_2$;
wherein $Y_I$ for each occurrence is independently $Z_I$ or a fully saturated, partially unsaturated or fully unsaturated one to ten membered straight or branched carbon chain wherein the carbons, other than the connecting carbon, may optionally be replaced with one or two heteroatoms selected independently from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono-, or di-substituted with oxo, and said carbon chain is optionally mono-substituted with $Z_I$;

wherein $Z_I$ is a partially saturated, fully saturated or fully unsaturated three to eight membered ring optionally having one to four heteroatoms selected independently from oxygen, sulfur and nitrogen, or, a bicyclic ring consisting of two fused partially saturated, fully saturated or fully unsaturated three to six membered rings, taken independently, optionally having one to four heteroatoms selected independently from nitrogen, sulfur and oxygen;

wherein said $Z_I$ substituent is optionally mono-, di- or tri-substituted independently with halo, $(C_2$-$C_6)$alkenyl, $(C_1$-$C_6)$ alkyl, hydroxy, $(C_1$-$C_6)$alkoxy, $(C_1$-$C_6)$alkylthio, amino, nitro, cyano, oxo, carboxyl, $(C_1$-$C_6)$alkyloxycarbonyl, mono-N— or di-N,N—$(C_1$-$C_6)$alkylamino wherein said $(C_1$-$C_6)$ alkyl substituent is optionally mono-, di- or tri-substituted independently with halo, hydroxy, $(C_1$-$C_6)$alkoxy, $(C_1$-$C_6)$ alkylthio, amino, nitro, cyano, oxo, carboxyl, $(C_1$-$C_6)$alkyloxycarbonyl, mono-N— or di-N,N—$(C_1$-$C_6)$alkylamino, said $(C_1$-$C_6)$alkyl substituent is also optionally substituted with from one to nine fluorines;
$R_{1-3}$ is hydrogen or $Q_I$;

wherein $Q_I$ is a fully saturated, partially unsaturated or fully unsaturated one to six membered straight or branched carbon chain wherein the carbons, other than the connecting carbon, may optionally be replaced with one heteroatom selected from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono-, or di-substituted with oxo, and said carbon chain is optionally mono-substituted with $V_I$;

wherein $V_I$ is a partially saturated, fully saturated or fully unsaturated three to eight membered ring optionally having one to four heteroatoms selected independently from oxygen, sulfur and nitrogen, or a bicyclic ring consisting of two fused partially saturated, fully saturated or fully unsaturated three to six membered rings, taken independently, optionally having one to four heteroatoms selected independently from nitrogen, sulfur and oxygen;

wherein said $V_I$ substituent is optionally mono-, di-, tri-, or tetra-substituted independently with halo, $(C_1$-$C_6)$alkyl, $(C_2$-$C_6)$alkenyl, hydroxy, $(C_1$-$C_6)$alkoxy, $(C_1$-$C_4)$alkylthio, amino, nitro, cyano, oxo, carbamoyl, mono-N— or di-N,N—$(C_1$-$C_6)$ alkylcarbamoyl, carboxyl, $(C_1$-$C_6)$alkyloxycarbonyl, mono-N— or di-N,N—$(C_1$-$C_6)$alkylamino wherein said $(C_1$-$C_6)$alkyl or $(C_2$-$C_6)$alkenyl substituent is optionally mono-, di- or tri-substituted independently with hydroxy, $(C_1$-$C_6)$alkoxy, $(C_1$-$C_4)$alkylthio, amino, nitro, cyano, oxo, carboxyl, $(C_1$-$C_6)$alkyloxycarbonyl, mono-N— or di-N,N—$(C_1$-$C_6)$alkylamino, said $(C_1$-$C_6)$alkyl or $(C_2$-$C_6)$alkenyl substituents are also optionally substituted with from one to nine fluorines;
$R_{1-4}$ is $Q_{I-1}$ or $V_{I-1}$ wherein $Q_{I-1}$ is a fully saturated, partially unsaturated or fully unsaturated one to six membered straight or branched carbon chain wherein the carbons, other than the connecting carbon, may optionally be replaced with one heteroatom selected from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono-, or di-substituted with oxo, and said carbon chain is optionally mono-substituted with $V_{I-1}$;

wherein $V_{I-1}$ is a partially saturated, fully saturated or fully unsaturated three to six membered ring optionally having one to two heteroatoms selected independently from oxygen, sulfur and nitrogen;

wherein said $V_{I-1}$ substituent is optionally mono-, di-, tri-, or tetra-substituted independently with halo, $(C_1\text{-}C_6)$alkyl, $(C_1\text{-}C_6)$alkoxy, amino, nitro, cyano, $(C_1\text{-}C_6)$alkyloxycarbonyl, mono-N— or di-N,N—$(C_2\text{-}C_6)$alkylamino wherein said $(C_1\text{-}C_6)$alkyl substituent is optionally mono-substituted with oxo, said $(C_1\text{-}C_6)$alkyl substituent is also optionally substituted with from one to nine fluorines;

wherein either $R_{I-3}$ must contain $V_I$ or $R_{I-4}$ must contain $V_{I-1}$; and $R_{I-5}$, $R_{I-6}$, $R_{I-7}$ and $R_{I-8}$ are each independently hydrogen, hydroxy or oxy wherein said oxy is substituted with $T_I$ or a partially saturated, fully saturated or fully unsaturated one to twelve membered straight or branched carbon chain wherein the carbons, other than the connecting carbon, may optionally be replaced with one or two heteroatoms selected independently from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono- or di-substituted with oxo, and said carbon chain is optionally mono-substituted with $T_I$;

wherein $T_I$ is a partially saturated, fully saturated or fully unsaturated three to eight membered ring optionally having one to four heteroatoms selected independently from oxygen, sulfur and nitrogen, or a bicyclic ring consisting of two fused partially saturated, fully saturated or fully unsaturated three to six membered rings, taken independently, optionally having one to four heteroatoms selected independently from nitrogen, sulfur and oxygen;

wherein said $T_I$ substituent is optionally mono-, di- or tri-substituted independently with halo, $(C_1\text{-}C_6)$alkyl, $(C_2\text{-}C_6)$alkenyl, hydroxy, $(C_1\text{-}C_6)$alkoxy, $(C_1\text{-}C_4)$alkylthio, amino, nitro, cyano, oxo, carboxy, $(C_1\text{-}C_6)$alkyloxycarbonyl, mono-N— or di-N,N—$(C_1\text{-}C_6)$alkylamino wherein said $(C_1\text{-}C_6)$alkyl substituent is optionally mono-, di- or tri-substituted independently with hydroxy, $(C_1\text{-}C_6)$alkoxy, $(C_1\text{-}C_4)$alkylthio, amino, nitro, cyano, oxo, carboxy, $(C_1\text{-}C_6)$alkyloxycarbonyl, mono-N— or di-N,N—$(C_1\text{-}C_6)$alkylamino, said $(C_1\text{-}C_6)$alkyl substituent is also optionally substituted with from one to nine fluorines.

Compounds of Formula I are disclosed in commonly assigned pending U.S. patent application Ser. No. 09/390, 731, the complete disclosure of which is herein incorporated by reference.

In a preferred embodiment, the CETP inhibitor is selected from one of the following compounds of Formula I:

[2R,4S]4-[(3,5-dichloro-benzyl)-methoxycarbonyl-amino]-6,7-dimethoxy-2-methyl-3,4-dihydro-2H-quinoline-1-carboxylic acid ethyl ester;

[2R,4S]4-[(3,5-dinitro-benzyl)-methoxycarbonyl-amino]-6,7-dimethoxy-2-methyl-3,4-dihydro-2H-quinoline-1-carboxylic acid ethyl ester;

[2R,4S]4-[(2,6-dichloro-pyridin-4-ylmethyl)-methoxycarbonyl-amino]-6,7-dimethoxy-2-methyl-3,4-dihydro-2H-quinoline-1-carboxylic acid ethyl ester;

[2R,4S]4-[(3,5-bis-trifluoromethyl-benzyl)-methoxycarbonyl-amino]-6,7-dimethoxy-2-methyl-3,4-dihydro-2H-quinoline-1-carboxylic acid ethyl ester;

[2R,4S]4-[(3,5-bis-trifluoromethyl-benzyl)-methoxycarbonyl-amino]-6-methoxy-2-methyl-3,4-dihydro-2H-quinoline-1-carboxylic acid ethyl ester;

[2R,4S]4-[(3,5-bis-trifluoromethyl-benzyl)-methoxycarbonyl-amino]-7-methoxy-2-methyl-3,4-dihydro-2H-quinoline-1-carboxylic acid ethyl ester,

[2R,4S]4-[(3,5-bis-trifluoromethyl-benzyl)-methoxycarbonyl-amino]-6,7-dimethoxy-2-methyl-3,4-dihydro-2H-quinoline-1-carboxylic acid isopropyl ester;

[2R,4S]4-[(3,5-bis-trifluoromethyl-benzyl)-ethoxycarbonyl-amino]-6,7-dimethoxy-2-methyl-3,4-dihydro-2H-quinoline-1-carboxylic acid ethyl ester;

[2R,4S]4-[(3,5-bis-trifluoromethyl-benzyl)-methoxycarbonyl-amino]-6,7-dimethoxy-2-methyl-3,4-dihydro-2H-quinoline-1-carboxylic acid 2,2,2-trifluoro-ethylester;

[2R,4S]4-[(3,5-bis-trifluoromethyl-benzyl)-methoxycarbonyl-amino]-6,7 dimethoxy-2-methyl-3,4-dihydro-2H-quinoline-1-carboxylic acid propyl ester;

[2R,4S]4-[(3,5-bis-trifluoromethyl-benzyl)-methoxycarbonyl-amino]-6,7-dimethoxy-2-methyl-3,4-dihydro-2H-quinoline-1-carboxylic acid tert-butyl ester;

[2R,4S]4-[(3,5-bis-trifluoromethyl-benzyl)-methoxycarbonyl-amino]-2-methyl-6-trifluoromethoxy-3,4-dihydro-2H-quinoline-1-carboxylic acid ethyl ester,

[2R,4S](3,5-bis-trifluoromethyl-benzyl)-(1-butyryl-6,7-dimethoxy-2-methyl-1,2,3,4-tetrahydro-quinolin-4-yl)-carbamic acid methyl ester;

[2R,4S](3,5-bis-trifluoromethyl-benzyl)-(1-butyl-6,7-dimethoxy-2-methyl-1,2,3,4-tetrahydro-quinolin-4-yl)-carbamic acid methyl ester;

[2R,4S](3,5-bis-trifluoromethyl-benzyl)-[1-(2-ethyl-butyl)-6,7-dimethoxy-2-methyl-1,2,3,4-tetrahydro-quinolin-4-yl]-carbamic acid methyl ester, hydrochloride.

Another class of CETP inhibitors that finds utility with the present invention consists of 4-carboxyamino-2-methyl-1,2, 3,4,-tetrahydroquinolines, having the Formula II

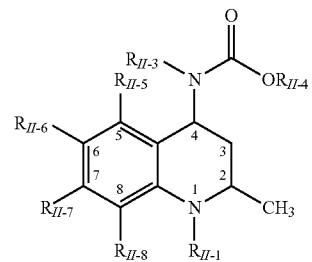

Formula II and pharmaceutically acceptable salts, enantiomers, or stereoisomers of said compounds;

wherein $R_{II-1}$ is hydrogen, $Y_{II}$, $W_{II}$—$X_{II}$, $W_{II}$—$Y_{II}$;

wherein $W_{II}$ is a carbonyl, thiocarbonyl, sulfinyl or sulfonyl;

$X_{II}$ is —O—$Y_{II}$, —S—$Y_{II}$, —N(H)—$Y_{II}$ or —N—$(Y_{II})_2$;

wherein $Y_{II}$ for each occurrence is independently $Z_{II}$ or a fully saturated, partially unsaturated or fully unsaturated one to ten membered straight or branched carbon chain wherein the carbons, other than the connecting carbon, may optionally be replaced with one or two heteroatoms selected independently from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono-, or di-substituted with oxo, and said carbon chain is optionally mono-substituted with $Z_{II}$;

$Z_{II}$ is a partially saturated, fully saturated or fully unsaturated three to twelve membered ring optionally having one to four heteroatoms selected independently from oxygen, sulfur and nitrogen, or a bicyclic ring consisting of two fused partially saturated, fully saturated or fully unsaturated three to six membered rings, taken independently, optionally having one to four heteroatoms selected independently from nitrogen, sulfur and oxygen;

wherein said $Z_{II}$ substituent is optionally mono-, di- or tri-substituted independently with halo, $(C_2$-$C_6)$alkenyl, $(C_1$-$C_6)$ alkyl, hydroxy, $(C_1$-$C_6)$alkoxy, $(C_1$-$C_4)$alkylthio, amino, nitro, cyano, oxo, carboxy, $(C_1$-$C_6)$alkyloxycarbonyl, mono-N— or di-N,N—$(C_1$-$C_6)$alkylamino wherein said $(C_1$-$C_6)$ alkyl substituent is optionally mono-, di- or tri-substituted independently with halo, hydroxy, $(C_1$-$C_6)$alkoxy, $(C_1$-$C_4)$alkylthio, amino, nitro, cyano, oxo, carboxy, $(C_1$-$C_6)$alkyloxycarbonyl, mono-N— or di-N,N—$(C_1$-$C_6)$alkylamino, said $(C_1$-$C_6)$alkyl is also optionally substituted with from one to nine fluorines;

$R_{II-3}$ is hydrogen or $Q_{II}$;

wherein $Q_{II}$ is a fully saturated, partially unsaturated or fully unsaturated one to six membered straight or branched carbon chain wherein the carbons, other than the connecting carbon, may optionally be replaced with one heteroatom selected from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono- or di-substituted with oxo, and said carbon chain is optionally mono-substituted with $V_{II}$;

wherein $V_{II}$ is a partially saturated, fully saturated or fully unsaturated three to twelve membered ring optionally having one to four heteroatoms selected independently from oxygen, sulfur and nitrogen, or, a bicyclic ring consisting of two fused partially saturated, fully saturated or fully unsaturated three to six membered rings, taken independently, optionally having one to four heteroatoms selected independently from nitrogen, sulfur and oxygen;

wherein said $V_{II}$ substituent is optionally mono-, di-, tri-, or tetra-substituted independently with halo, $(C_1$-$C_6)$alkyl, $(C_2$-$C_6)$alkenyl, hydroxy, $(C_1$-$C_6)$alkoxy, $(C_1$-$C_4)$alkylthio, amino, nitro, cyano, oxo, carboxamoyl, mono-N— or di-N,N—$(C_1$-$C_6)$ alkylcarboxamoyl, carboxy, $(C_1$-$C_6)$alkyloxycarbonyl, mono-N— or di-N,N—$(C_1$-$C_6)$alkylamino wherein said $(C_1$-$C_6)$alkyl or $(C_2$-$C_6)$alkenyl substituent is optionally mono-, di- or tri-substituted independently with hydroxy, $(C_1$-$C_6)$alkoxy, $(C_1$-$C_4)$alkylthio, amino, nitro, cyano, oxo, carboxy, $(C_1$-$C_6)$alkyloxycarbonyl, mono-N— or di-N,N—$(C_1$-$C_6)$alkylamino or said $(C_1$-$C_6)$alkyl or $(C_2$-$C_6)$alkenyl substituents are optionally substituted with from one to nine fluorines;

$R_{II-4}$ is $Q_{II-1}$ or $V_{II-1}$ wherein $Q_{II-1}$ a fully saturated, partially unsaturated or fully unsaturated one to six membered straight or branched carbon chain wherein the carbons, other than the connecting carbon, may optionally be replaced with one heteroatom selected from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono- or di-substituted with oxo, and said carbon chain is optionally mono-substituted with $V_{II-1}$;

wherein $V_{II-1}$ is a partially saturated, fully saturated or fully unsaturated three to six membered ring optionally having one to two heteroatoms selected independently from oxygen, sulfur and nitrogen;

wherein said $V_{II-1}$ substituent is optionally mono-, di-, tri-, or tetra-substituted independently with halo, $(C_1$-$C_6)$alkyl, $(C_1$-$C_6)$alkoxy, amino, nitro, cyano, $(C_1$-$C_6)$alkyloxycarbonyl, mono-N— or di-N,N—$(C_1$-$C_6)$alkylamino wherein said $(C_1$-$C_6)$alkyl substituent is optionally mono-substituted with oxo, said $(C_1$-$C_6)$alkyl substituent is optionally substituted with from one to nine fluorines;

wherein either $R_{II-3}$ must contain $V_{II}$ or $R_{II-4}$ must contain $V_{II-1}$; and $R_{II-5}$, $R_{II-6}$, $R_{II-7}$ and $R_{II-8}$ are each independently hydrogen, a bond, nitro or halo wherein said bond is substituted with $T_{II}$ or a partially saturated, fully saturated or fully unsaturated $(C_1$-$C_{12})$ straight or branched carbon chain wherein carbon may optionally be replaced with one or two heteroatoms selected independently from oxygen, sulfur and nitrogen wherein said carbon atoms are optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono- or di-substituted with oxo, and said carbon is optionally mono-substituted with $T_{II}$;

wherein $T_{II}$ is a partially saturated, fully saturated or fully unsaturated three to twelve membered ring optionally having one to four heteroatoms selected independently from oxygen, sulfur and nitrogen, or, a bicyclic ring consisting of two fused partially saturated, fully saturated or fully unsaturated three to six membered rings, taken independently, optionally having one to four heteroatoms selected independently from nitrogen, sulfur and oxygen;

wherein said $T_{II}$ substituent is optionally mono-, di- or tri-substituted independently with halo, $(C_1$-$C_6)$alkyl, $(C_2$-$C_6)$alkenyl, hydroxy, $(C_1$-$C_6)$alkoxy, $(C_1$-$C_6)$alkylthio, amino, nitro, cyano, oxo, carboxy, $(C_1$-$C_6)$alkyloxycarbonyl, mono-N— or di-N,N—$(C_1$-$C_6)$alkylamine wherein said $(C_1$-$C_6)$alkyl substituent is optionally mono-, di- or tri-substituted independently with hydroxy, $(C_1$-$C_6)$alkoxy, $(C_1$-$C_6)$alkylthio, amino, nitro, cyano, oxo, carboxy, $(C_1$-$C_6)$alkyloxycarbonyl, mono-N— or di-N,N—$(C_1$-$C_6)$alkylamino, said $(C_1$-$C_6)$alkyl substituent is also optionally substituted with from one to nine fluorines; provided that at least one of substituents $R_{II-5}$, $R_{II-6}$, $R_{II-7}$ and $R_{II-8}$ is not hydrogen and is not linked to the quinoline moiety through oxy.

Compounds of Formula II are disclosed in commonly assigned pending U.S. patent application Ser. No. 09/391,273 the complete disclosure of which is herein incorporated by reference.

In a preferred embodiment, the CETP inhibitor is selected from one of the following compounds of Formula II:

[2R,4S]4-[(3,5-Bis-trifluoromethyl-benzyl)-methoxycarbonyl-amino]-2-methyl-7-trifluoromethyl 3,4-dihydro-2H-quinoline-1-carboxylic acid ethyl ester;

[2R,4S]4-[(3,5-Bis-trifluoromethyl-benzyl)-methoxycarbonyl-amino]-7-chloro-2-methyl-3,4-dihydro-2H-quinoline-1-carboxylic acid ethyl ester;

[2R,4S]4-[(3,5-Bis-trifluoromethyl-benzyl)-methoxycarbonyl-amino]-6-chloro-2-methyl-3,4-dihydro-2H-quinoline-1-carboxylic acid ethyl ester;

[2R,4S]4-[(3,5-Bis-trifluoromethyl-benzyl)-methoxycarbonyl-amino]-2,6,7-trimethyl-3,4-dihydro-2H-quinoline-1-carboxylic acid ethyl ester

[2R,4S]4-[(3,5-Bis-trifluoromethyl-benzyl)-methoxycarbonyl-amino]-6,7-diethyl-2-methyl-3,4-dihydro-2H-quinoline-1-carboxylic acid ethyl ester;

[2R,4S]4-[(3,5-Bis-trifluoromethyl-benzyl)-methoxycarbonyl-amino]-6-ethyl-2-methyl-3,4-dihydro-2H-quinoline-1-carboxylic acid ethyl ester;

[2R,4S]4-[(3,5-Bis-trifluoromethyl-benzyl)-methoxycarbonyl-amino]-2-methyl-6-trifluoromethyl-3,4-dihydro-2H-quinoline-1-carboxylic acid ethyl ester.

[2R,4S]4-[(3,5-bis-trifluoromethyl-benzyl)-methoxycarbonyl-amino]-2-methyl-6-trifluoromethyl-3,4-dihydro-2H-quinoline-1-carboxylic acid isopropyl ester.

Another class of CETP inhibitors that finds utility with the present invention consists of annulated 4-carboxyamino-2-methyl-1,2,3,4,-tetrahydroquinolines, having the Formula III

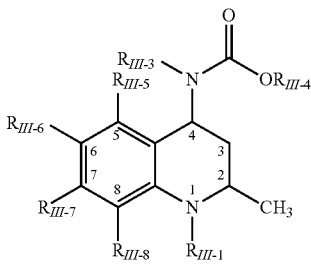

Formula III and pharmaceutically acceptable salts, enantiomers, or stereoisomers of said compounds;
wherein $R_{III\text{-}1}$ is hydrogen, $Y_{III}$, $W_{III}$—$X_{III}$, $W_{III}$—$Y_{III}$;
wherein $W_{III}$ is a carbonyl, thiocarbonyl, sulfinyl or sulfonyl;
$X_{III}$ is —O—$Y_{III}$, —S—$Y_{III}$, —N(H)—$Y_{III}$ or —N—$(Y_{III})_2$;
$Y_{III}$ for each occurrence is independently $Z_{III}$ or a fully saturated, partially unsaturated or fully unsaturated one to ten membered straight or branched carbon chain wherein the carbons, other than the connecting carbon, may optionally be replaced with one or two heteroatoms selected independently from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono-, or di-substituted with oxo; and said carbon chain is optionally mono-substituted with $Z_{III}$;

wherein $Z_{III}$ is a partially saturated, fully saturated or fully unsaturated three to twelve membered ring optionally having one to four heteroatoms selected independently from oxygen, sulfur and nitrogen, or a bicyclic ring consisting of two fused partially saturated, fully saturated or fully unsaturated three to six membered rings, taken independently, optionally having one to four heteroatoms selected independently from nitrogen, sulfur and oxygen;

wherein said $Z_{III}$ substituent is optionally mono-, di- or tri-substituted independently with halo, $(C_2\text{-}C_6)$alkenyl, $(C_1\text{-}C_6)$ alkyl, hydroxy, $(C_1\text{-}C_6)$alkoxy, $(C_1\text{-}C_4)$alkylthio, amino, nitro, cyano, oxo, carboxy, $C_1\text{-}C_6$)alkyloxycarbonyl, mono-N— or di-N,N—$(C_3\text{-}C_6)$alkylamino wherein said $(C_1\text{-}C_6)$ alkyl substituent is optionally mono-, di- or tri-substituted independently with halo, hydroxy, $(C_1\text{-}C_6)$alkoxy, $(C_1\text{-}C_4)$ alkylthio, amino, nitro, cyano, oxo, carboxy, $(C_1\text{-}C_6)$alkyloxycarbonyl, mono-N— or di-N,N—$(C_1\text{-}C_6)$alkylamino, said $(C_1\text{-}C_6)$alkyl optionally substituted with from one to nine fluorines;

$R_{III\text{-}3}$ is hydrogen or $Q_{III}$;
wherein $Q_{III}$ is a fully saturated, partially unsaturated or fully unsaturated one to six membered straight or branched carbon chain wherein the carbons, other than the connecting carbon, may optionally be replaced with one heteroatom selected from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono- or di-substituted with oxo, and said carbon chain is optionally mono-substituted with $V_{III}$;

wherein $V_{III}$ is a partially saturated, fully saturated or fully unsaturated three to twelve membered ring optionally having one to four heteroatoms selected independently from oxygen, sulfur and nitrogen, or a bicyclic ring consisting of two fused partially saturated, fully saturated or fully unsaturated three to six membered rings, taken independently, optionally having one to four heteroatoms selected independently from nitrogen, sulfur and oxygen;

wherein said $V_{III}$ substituent is optionally mono-, di-, tri-, or tetra-substituted independently with halo, $(C_1\text{-}C_6)$alkyl, $(C_2\text{-}C_6)$alkenyl, hydroxy, $(C_1\text{-}C_6)$alkoxy, $(C_1\text{-}C_4)$alkylthio, amino, nitro, cyano, oxo, carboxamoyl, mono-N— or di-N, N—$(C_1\text{-}C_6)$ alkylcarboxamoyl, carboxy, $(C_1\text{-}C_6)$alkyloxycarbonyl, mono-N— or di-N,N—$(C_1\text{-}C_6)$alkylamino wherein said $(C_1\text{-}C_6)$alkyl or $(C_2\text{-}C_6)$alkenyl substituent is optionally mono-, di- or tri-substituted independently with hydroxy, $(C_1\text{-}C_6)$alkoxy, $(C_1\text{-}C_6)$alkylthio, amino, nitro, cyano, oxo, carboxy, $(C_1\text{-}C_6)$alkyloxycarbonyl, mono-N— or di-N,N—$(C_1\text{-}C_6)$alkylamino or said $(C_1\text{-}C_6)$alkyl or $(C_2\text{-}C_6)$alkenyl are optionally substituted with from one to nine fluorines;

$R_{III\text{-}4}$ is $Q_{III\text{-}1}$ or $V_{III\text{-}1}$;
wherein $Q_{III\text{-}1}$ a fully saturated, partially unsaturated or fully unsaturated one to six membered straight or branched carbon chain wherein the carbons, other than the connecting carbon, may optionally be replaced with one heteroatom selected from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono- or di-substituted with oxo, and said carbon chain is optionally mono-substituted with $V_{III\text{-}1}$;

wherein $V_{III\text{-}1}$ is a partially saturated, fully saturated or fully unsaturated three to six membered ring optionally having one to two heteroatoms selected independently from oxygen, sulfur and nitrogen;

wherein said $V_{III\text{-}1}$ substituent is optionally mono-, di-, tri-, or tetra-substituted independently with halo, $(C_1\text{-}C_6)$alkyl, $(C_1\text{-}C_6)$alkoxy, amino, nitro, cyano, $(C_1\text{-}C_6)$ alkyloxycarbonyl, mono-N— or di-N,N—$(C_1\text{-}C_6)$ alkylamino wherein said $(C_1\text{-}C_6)$alkyl substituent is optionally mono-substituted with oxo, said $(C_1\text{-}C_6)$alkyl substituent optionally having from one to nine fluorines;

wherein either $R_{III\text{-}3}$ must contain $V_{III}$ or $R_{III\text{-}4}$ must contain $V_{III\text{-}1}$; and $R_{III\text{-}5}$ and $R_{III\text{-}6}$, or $R_{III\text{-}6}$ and $R_{III\text{-}7}$, and/or $R_{III\text{-}7}$ and $R_{III\text{-}8}$ are taken together and form at least one four to eight membered ring that is partially saturated or fully unsaturated optionally having one to three heteroatoms independently selected from nitrogen, sulfur and oxygen;
wherein said ring or rings formed by $R_{III-5}$ and $R_{III-6}$, or $R_{III-6}$ and $R_{III-7}$, and/or $R_{III-7}$ and $R_{III-8}$ are optionally mono-, di- or tri-substituted independently with halo, $(C_1-C_6)$alkyl, $(C_1-C_4)$alkylsulfonyl, $(C_2-C_6)$alkenyl, hydroxy, $(C_1-C_6)$alkoxy, $(C_1-C_4)$alkylthio, amino, nitro, cyano, oxo, carboxy, $(C_1-C_6)$alkyloxycarbonyl, mono-N— or di-N,N—$(C_1-C_6)$alkylamino wherein said $(C_1-C_6)$alkyl substituent is optionally mono-, di- or tri-substituted independently with hydroxy, $(C_1-C_6)$alkoxy, $(C_1-C_4)$alkylthio, amino, nitro, cyano, oxo, carboxy, $(C_1-C_6)$alkyloxycarbonyl, mono-N— or di-N,N—$(C_1-C_6)$alkylamino, said $(C_1-C_6)$alkyl substituent optionally having from one to nine fluorines;

provided that the $R_{III-5}$, $R_{III-6}$, $R_{III-7}$ and/or $R_{III-8}$, as the case may be, that do not form at least one ring are each independently hydrogen, halo, $(C_1-C_6)$alkoxy or $(C_1-C_6)$alkyl, said $(C_1-C_6)$alkyl optionally having from one to nine fluorines.

Compounds of Formula III are disclosed in commonly assigned pending U.S. patent application Ser. No. 09/390,738 the complete disclosure of which is herein incorporated by reference.

In a preferred embodiment, the CETP inhibitor is selected from one of the following compounds of Formula III:
[2R,4S]4-[(3,5-bis-trifluoromethyl-benzyl)-methoxycarbonyl-amino]-2-methyl-2,3,4,6,7,8-hexahydro-cyclopenta[g]quinoline-1-carboxylic acid ethyl ester;
[6R, 8S]8-[(3,5-bis-trifluoromethyl-benzyl)-methoxycarbonyl-amino]-6-methyl-3,6,7,8-tetrahydro-1H-2-thia-5-aza-cyclopenta[b]naphthalene-5-carboxylic acid ethylester;
[6R, 8S]8-[(3,5-bis-trifluoromethyl-benzyl)-methoxycarbonyl-amino]-6-methyl-3,6,7,8-tetrahydro-2H-furo[2,3-g]quinoline-5-carboxylic acid ethyl ester;
[2R,4S]4-[(3,5-bis-trifluoromethyl-benzyl)-methoxycarbonyl-amino]-2-methyl-3,4,6,8-tetrahydro-2H-furo[3,4-g]quinoline-1-carboxylic acid ethyl ester;
[2R,4S]4-[(3,5-bis-trifluoromethyl-benzyl)-methoxycarbonyl-amino]-2-methyl-3,4,6,7,8,9-hexahydro-2H-benzo[g]quinoline-1-carboxylic acid propyl ester;
[7R,9S]9-[(3,5-bis-trifluoromethyl-benzyl)-methoxycarbonyl-amino]-7-methyl-1,2,3,7,8,9-hexahydro-6-aza-cyclopenta[a]naphthalene-6-carboxylic acid ethyl ester; and
[6S,8R]6-[(3,5-bis-trifluoromethyl-benzyl)-methoxycarbonyl-amino]-8-methyl-1,2,3,6,7,8-hexahydro-9-aza-cyclopenta[a]naphthalene-9-carboxylic acid ethyl ester.

Another class of CETP inhibitors that finds utility with the present invention consists of 4-carboxyamino-2-substituted-1,2,3,4,-tetrahydroquinolines, having the Formula IV

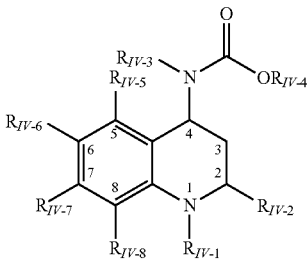

Formula IV and pharmaceutically acceptable salts, enantiomers, or stereoisomers of said compounds;
wherein $R_{IV-1}$ is hydrogen, $Y_{IV}$, $W_{IV}$—$X_{IV}$ or $W_{IV}$—$Y_{IV}$;
wherein $W_{IV}$ is a carbonyl, thiocarbonyl, sulfinyl or sulfonyl;
$X_{IV}$ is —O—$Y_{IV}$, —S—$Y_{IV}$, —N(H)—$Y_{IV}$ or —N—$(Y_{IV})_2$;
wherein $Y_{IV}$ for each occurrence is independently $Z_{IV}$ or a fully saturated, partially unsaturated or fully unsaturated one to ten membered straight or branched carbon chain wherein the carbons, other than the connecting carbon, may optionally be replaced with one or two heteroatoms selected independently from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono-, or di-substituted with oxo, and said carbon chain is optionally mono-substituted with $Z_{IV}$;

wherein $Z_{IV}$ is a partially saturated, fully saturated or fully unsaturated three to eight membered ring optionally having one to four heteroatoms selected independently from oxygen, sulfur and nitrogen, or a bicyclic ring consisting of two fused partially saturated, fully saturated or fully unsaturated three to six membered rings, taken independently, optionally having one to four heteroatoms selected independently from nitrogen, sulfur and oxygen;

wherein said $Z_{IV}$ substituent is optionally mono-, di- or tri-substituted independently with halo, $(C_2-C_6)$alkenyl, $(C_1-C_6)$ alkyl, hydroxy, $(C_1-C_6)$alkoxy, $(C_1-C_4)$alkylthio, amino, nitro, cyano, oxo, carboxy, $(C_1-C_6)$alkyloxycarbonyl, mono-N— or di-N,N—$(C_1-C_6)$alkylamino wherein said $(C_1-C_6)$alkyl substituent is optionally mono-, di- or tri-substituted independently with halo, hydroxy, $(C_1-C_6)$alkoxy, $(C_1-C_6)$alkylthio, amino, nitro, cyano, oxo, carboxy, $(C_1-C_6)$alkyloxycarbonyl, mono-N— or di-N,N—$(C_1-C_6)$alkylamino, said $(C_1-C_6)$alkyl substituent is also optionally substituted with from one to nine fluorines;

$R_{IV-2}$ is a partially saturated, fully saturated or fully unsaturated one to six membered straight or branched carbon chain wherein the carbons, other than the connecting carbon, may optionally be replaced with one or two heteroatoms selected independently from oxygen, sulfur and nitrogen wherein said carbon atoms are optionally mono-, di- or tri-substituted independently with halo, said carbon is optionally mono-substituted with oxo, said carbon is optionally mono-substituted with hydroxy, said sulfur is optionally mono- or di-substituted with oxo, said nitrogen is optionally mono- or di-substituted with oxo; or said $R_{IV-2}$ is a partially saturated, fully saturated or fully unsaturated three to seven membered ring optionally having one to two heteroatoms selected independently from oxygen, sulfur and nitrogen, wherein said $R_{IV-2}$ ring is optionally attached through $(C_1-C_6)$alkyl;

wherein said $R_{IV-2}$ ring is optionally mono-, di- or tri-substituted independently with halo, $(C_2-C_6)$alkenyl, $(C_1-C_6)$ alkyl, hydroxy, $(C_1-C_6)$alkoxy, $(C_1-C_4)$alkylthio, amino, nitro, cyano, oxo, carboxy, $(C_1-C_6)$alkyloxycarbonyl, mono-N— or di-N,N—$(C_1-C_6)$alkylamino wherein said $(C_1-C_6)$alkyl substituent is optionally mono-, di- or tri-substituted independently with halo, hydroxy, $(C_1-C_6)$alkoxy, $(C_1-C_4)$alkylthio, oxo or $(C_1-C_6)$ alkyloxycarbonyl;

with the proviso that $R_{IV-2}$ is not methyl; $R_{IV-3}$ is hydrogen or $Q_{IV}$;

wherein $Q_{IV}$ is a fully saturated, partially unsaturated or fully unsaturated one to six membered straight or branched carbon chain wherein the carbons other than the connecting carbon, may optionally be replaced with one heteroatom selected from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono- or di-substituted with oxo, and said carbon chain is optionally mono-substituted with $V_{IV}$;

wherein $V_{IV}$ is a partially saturated, fully saturated or fully unsaturated three to eight membered ring optionally having one to four heteroatoms selected independently from oxygen, sulfur and nitrogen, or a bicyclic ring consisting of two fused partially saturated, fully saturated or fully unsaturated three to six membered rings, taken independently, optionally having one to four heteroatoms selected independently from nitrogen, sulfur and oxygen;

wherein said $V_{IV}$ substituent is optionally mono-, di-, tri-, or tetra-substituted independently with halo, $(C_1-C_6)$alkyl, $(C_2-C_6)$alkenyl, hydroxy, $(C_1-C_6)$alkoxy, $(C_1-C_4)$alkylthio, amino, nitro, cyano, oxo, carboxamoyl, mono-N— or di-N, N—$(C_1-C_6)$ alkylcarboxamoyl, carboxy, $(C_1-C_6)$alkyloxycarbonyl, mono-N— or di-N,N—$(C_1-C_6)$alkylamino wherein said $(C_1-C_6)$alkyl or $(C_2-C_6)$alkenyl substituent is optionally mono-, di- or tri-substituted independently with hydroxy, $(C_1-C_6)$alkoxy, $(C_1-C_4)$alkylthio, amino, nitro, cyano, oxo, carboxy, $(C_1-C_6)$alkyloxycarbonyl, mono-N— or di-N,N—$(C_1-C_6)$alkylamino, said $(C_1-C_6)$alkyl or $(C_2-C_6)$ alkenyl substituents are also optionally substituted with from one to nine fluorines;

$R_{IV-4}$ is $Q_{IV-1}$ or $V_{IV-1}$;

wherein $Q_{IV-1}$ a fully saturated, partially unsaturated or fully unsaturated one to six membered straight or branched carbon chain wherein the carbons, other than the connecting carbon, may optionally be replaced with one heteroatom selected from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono- or di-substituted with oxo, and said carbon chain is optionally mono-substituted with $V_{IV-1}$;

wherein $V_{IV-1}$ is a partially saturated, fully saturated or fully unsaturated three to six membered ring optionally having one to two heteroatoms selected independently from oxygen, sulfur and nitrogen;

wherein said $V_{IV-1}$ substituent is optionally mono-; di-, tri-, or tetra-substituted independently with halo, $(C_1-C_6)$alkyl, $(C_1-C_6)$alkoxy, amino, nitro, cyano, $(C_1-C_6)$alkyloxycarbonyl, mono-N— or di-N,N—$(C_1-C_6)$alkylamino wherein said $(C_1-C_6)$alkyl substituent is optionally mono-substituted with oxo, said $(C_1-C_6)$alkyl substituent is also optionally substituted with from one to nine fluorines;

wherein either $R_{IV-3}$ must contain $V_{IV}$ or $R_{IV-4}$ must contain $V_{IV-1}$;

$R_{IV-5}$, $R_{IV-6}$, $R_{IV-7}$ and $R_{IV-8}$ are each independently hydrogen, a bond, nitro or halo wherein said bond is substituted with $T_{IV}$ or a partially saturated, fully saturated or fully unsaturated $(C_1-C_{12})$ straight or branched carbon chain wherein carbon, may optionally be replaced with one or two heteroatoms selected independently from oxygen, sulfur and nitrogen wherein said carbon atoms are optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono- or di-substituted with oxo, and said carbon is optionally mono-substituted with $T_{IV}$;

wherein $T_{IV}$ is a partially saturated, fully saturated or fully unsaturated three to eight membered ring optionally having one to four heteroatoms selected independently from oxygen, sulfur and nitrogen, or, a bicyclic ring consisting of two fused partially saturated, fully saturated or fully unsaturated three to six membered rings, taken independently, optionally having one to four heteroatoms selected independently from nitrogen, sulfur and oxygen;

wherein said $T_{IV}$ substituent is optionally mono-, di- or tri-substituted independently with halo, $(C_1-C_6)$alkyl, $(C_2-C_6)$alkenyl, hydroxy, $(C_1-C_6)$alkoxy, $(C_1-C_4)$alkylthio, amino, nitro, cyano, oxo, carboxy, $(C_1-C_6)$alkyloxycarbonyl, mono-N— or di-N,N—$(C_1-C_6)$alkylamino wherein said $(C_1-C_6)$alkyl substituent is optionally mono-, di- or tri-substituted independently with hydroxy, $(C_1-C_6)$alkoxy, $(C_1-C_4)$alkylthio, amino, nitro, cyano, oxo, carboxy, $(C_1-C_6)$alkyloxycarbonyl, mono-N— or di-N,N—$(C_1-C_6)$alkylamino, said $(C_1-C_6)$alkyl substituent is also optionally substituted with from one to nine fluorines; and wherein $R_{IV-5}$ and $R_{IV-6}$, or $R_{IV-6}$ and $R_{IV-7}$, and/or $R_{IV-7}$ and $R_{IV-8}$ may also be taken together and can form at least one four to eight membered ring that is partially saturated or fully unsaturated optionally having one to three heteroatoms independently selected from nitrogen, sulfur and oxygen;

wherein said ring or rings formed by $R_{II-5}$ and $R_{IV-6}$, or $R_{IV-6}$ and $R_{IV-7}$, and/or $R_{IV-7}$ and $R_{IV-8}$ are optionally mono-, di- or tri-substituted independently with halo, $(C_1-C_6)$alkyl, $(C_1-C_4)$ alkylsulfonyl, $(C_2-C_6)$alkenyl, hydroxy, $(C_1-C_6)$alkoxy, $(C_1-C_4)$alkylthio, amino, nitro, cyano, oxo, carboxy, $(C_1-C_6)$alkyloxycarbonyl, mono-N— or di-N,N—$(C_1-C_6)$ alkylamino wherein said $(C_1-C_6)$alkyl substituent is optionally mono-, di- or tri-substituted independently with hydroxy, $(C_1-C_6)$alkoxy, $(C_1-C_4)$alkylthio, amino, nitro, cyano, oxo, carboxy, $(C_1-C_6)$alkyloxycarbonyl, mono-N— or di-N,N— $(C_1-C_6)$alkylamino, said $(C_1-C_6)$alkyl substituent is also optionally substituted with from one to nine fluorines;

with the proviso that when $R_{IV-2}$ is carboxyl or $(C_1-C_4)$alkylcarboxyl, then $R_{IV-1}$ is not hydrogen.

Compounds of Formula IV are disclosed in commonly assigned pending U.S. patent application Ser. No. 09/391,152 the complete disclosure of which is herein incorporated by reference.

In a preferred embodiment, the CETP inhibitor is selected from one of the following compounds of Formula IV:

[2S,4S]4-[(3,5-bis-trifluoromethyl-benzyl)-methoxycarbonyl-amino]-2-isopropyl-6-trifluoromethyl-3,4-dihydro-2H-quinoline-1-carboxylic acid isopropyl ester;

[2S,4S]4-[(3,5-bis-trifluoromethyl-benzyl)-methoxycarbonyl-amino]-6-chloro-2-cyclopropyl-3,4-dihydro-2H-quinoline-1-carboxylic acid isopropyl ester;

[2S,4S]2-cyclopropyl-4-[(3,5-dichloro-benzyl)-methoxycarbonyl-amino]-6-trifluoromethyl-3,4-dihydro-2H-quinoline-1-carboxylic acid isopropyl ester;

[2S,4S]4-[(3,5-bis-trifluoromethyl-benzyl)-methoxycarbonyl-amino]-2-cyclopropyl-6-trifluoromethyl-3,4-dihydro-2H-quinoline-1-carboxylic acid tert-butyl ester;

[2R,4R]4-[(3,5-bis-trifluoromethyl-benzyl)-methoxycarbonyl-amino]-2-cyclopropyl-6-trifluoromethyl-3,4-dihydro-2H-quinoline-1-carboxylic acid isopropyl ester;

[2S,4S]4-[(3,5-bis-trifluoromethyl-benzyl)-methoxycarbonyl-amino]-2-cyclopropyl-6-trifluoromethyl-3,4-dihydro-2H-quinoline-1-carboxylic acid isopropyl ester;

[2S,4S]4-[(3,5-bis-trifluoromethyl-benzyl)-methoxycarbonyl-amino]-2-cyclobutyl-6-trifluoromethyl-3,4-dihydro-2H-quinoline-1-carboxylic acid isopropyl ester;

[2R,4S]4-[(3,5-bis-trifluoromethyl-benzyl)-methoxycarbonyl-amino]-2-ethyl-6-trifluoromethyl-3,4-dihydro-2H-quinoline-1-carboxylic acid isopropyl ester;

[2S,4S]4-[(3,5-bis-trifluoromethyl-benzyl)-methoxycarbo-nyl-amino]-2-methoxymethyl-6-trifluoromethyl-3,4-dihydro-2H-quinoline 1-carboxylic acid isopropyl ester;

[2R,4S]4-[(3,5-bis-trifluoromethyl-benzyl)-methoxycarbo-nyl-amino]-2-ethyl-6-trifluoromethyl-3,4-dihydro-2H-quinoline-1-carboxylic acid 2-hydroxy-ethyl ester;

[2S,4S]4-[(3,5-bis-trifluoromethyl-benzyl)-methoxycarbo-nyl-amino]-2-cyclopropyl-6-trifluoromethyl-3,4-dihydro-2H-quinoline-1-carboxylic acid ethyl ester;

[2R,4S]4-[(3,5-bis-trifluoromethyl-benzyl)-methoxycarbo-nyl-amino]-2-ethyl-6-trifluoromethyl-3,4-dihydro-2H-quinoline-1-carboxylic acid ethyl ester;

[2S,4S]4-[(3,5-bis-trifluoromethyl-benzyl)-methoxycarbo-nyl-amino]-2-cyclopropyl-6-trifluoromethyl-3,4-dihydro-2H-quinoline-1-carboxylic acid propyl ester; and

[2R,4S]4-[(3,5-bis-trifluoromethyl-benzyl)-methoxycarbo-nyl-amino]-2-ethyl-6-trifluoromethyl-3,4-dihydro-2H-quinoline-1-carboxylic acid propyl ester.

Another class of CETP inhibitors that finds utility with the present invention consists of 4-amino substituted-2-substi-tuted-1,2,3,4,-tetrahydroquinolines, having the Formula V

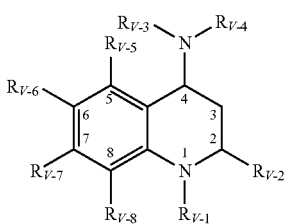

Formula V and pharmaceutically acceptable salts, enantiomers, or stereoisomers of said compounds;

wherein $R_{V-1}$ is $Y_V$, $W_V-X_V$ or $W_V-Y_V$;

wherein $W_V$ is a carbonyl, thiocarbonyl, sulfinyl or sulfonyl;

$X_V$ is —O—$Y_V$, —S—$Y_V$, —N(H)—$Y_V$ or —N—$(Y)_2$;

wherein $Y_V$ for each occurrence is independently Z, or a fully saturated, partially unsaturated or fully unsaturated one to ten membered straight or branched carbon chain wherein the carbons, other than the connecting carbon, may optionally be replaced with one or more heteroatoms selected independently from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono-, or di-substituted with oxo, and said carbon chain is optionally mono-substituted with $Z_V$;

wherein $Z_V$ is a partially saturated, fully saturated or fully unsaturated three to eight membered ring optionally having one to four heteroatoms selected independently from oxygen, sulfur and nitrogen, or a bicyclic ring consisting of two fused partially saturated, fully saturated or fully unsaturated three to six membered rings, taken independently, optionally having one to four heteroatoms selected independently from nitrogen, sulfur and oxygen;

wherein said $Z_V$ substituent is optionally mono-, di- or tri-substituted independently with halo, $(C_2-C_6)$alkenyl, $(C_1-C_6)$ alkyl, hydroxy, $(C_1-C_6)$alkoxy, $(C_1-C_4)$alkylthio, amino, nitro, cyano, oxo, carboxy, $(C_1-C_6)$alkyloxycarbonyl, mono-N— or di-N,N—$(C_1-C_6)$alkylamino wherein said $(C_1-C_6)$ alkyl substituent is optionally mono-, di- or tri-substituted independently with halo, hydroxy, $(C_1-C_6)$alkoxy, $(C_1-C_4)$ alkylthio, amino, nitro, cyano, oxo, carboxy, $(C_1-C_6)$alkyloxycarbonyl, mono-N— or di-N,N—$(C_1-C_6)$alkylamino, said $(C_1-C_6)$alkyl substituent is also optionally substituted with from one to nine fluorines;

$R_{V-2}$ is a partially saturated, fully saturated or fully unsaturated one to six membered straight or branched carbon chain wherein the carbons, other than the connecting carbon, may optionally be replaced with one or two heteroatoms selected independently from oxygen, sulfur and nitrogen wherein said carbon atoms are optionally mono-, di- or tri-substituted independently with halo, said carbon is optionally mono-substituted with oxo, said carbon is optionally mono-substituted with hydroxy, said sulfur is optionally mono- or di-substituted with oxo, said nitrogen is optionally mono- or di-substituted with oxo; or said $R_{V-2}$ is a partially saturated, fully saturated or fully unsaturated three to seven membered ring optionally having one to two heteroatoms selected independently from oxygen, sulfur and nitrogen, wherein said $R_{V-2}$ ring is optionally attached through $(C_1-C_4)$alkyl;

wherein said $R_{V-2}$ ring is optionally mono-, di- or tri-substituted independently with halo, $(C_2-C_6)$alkenyl, $(C_1-C_6)$ alkyl, hydroxy, $(C_1-C_6)$alkoxy, $(C_1-C_4)$alkylthio, amino, nitro, cyano, oxo, carboxy, $(C_1-C_6)$alkyloxycarbonyl, mono-N— or di-N,N—$(C_1-C_6)$alkylamino wherein said $(C_1-C_6)$ alkyl substituent is optionally mono-, di- or tri-substituted independently with halo, hydroxy, $(C_1-C_6)$alkoxy, $(C_1-C_4)$ alkylthio, oxo or $(C_1-C_6)$ alkyloxycarbonyl;

$R_{V-3}$ is hydrogen or $Q_V$;

wherein $Q_V$ is a fully saturated, partially unsaturated or fully unsaturated one to six membered straight or branched carbon chain wherein the carbons, other than the connecting carbon, may optionally be replaced with one heteroatom selected from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono-, or di-substituted with oxo, and said carbon chain is optionally mono-substituted with $V_V$;

wherein $V_V$ is a partially saturated, fully saturated or fully unsaturated three to eight membered ring optionally having one to four heteroatoms selected independently from oxygen, sulfur and nitrogen, or a bicyclic ring consisting of two fused partially saturated, fully saturated or fully unsaturated three to six membered rings, taken independently, optionally having one to four heteroatoms selected independently from nitrogen, sulfur and oxygen;

wherein said $V_V$ substituent is optionally mono-, di-, tri-, or tetra-substituted independently with halo, $(C_1-C_6)$alkyl, $(C_2-C_6)$alkenyl, hydroxy, $(C_1-C_6)$alkoxy, $(C_1-C_4)$alkylthio, amino, nitro, cyano, oxo, carboxamoyl, mono-N— or di-N,N—$(C_1-C_6)$ alkylcarboxamoyl, carboxy, $(C_1-C_6)$alkyloxycarbonyl, mono-N— or di-N,N—$(C_1-C_6)$alkylamino wherein said $(C_1-C_6)$alkyl or $(C_2-C_6)$alkenyl substituent is optionally mono-, di- or tri-substituted independently with hydroxy, $(C_1-C_6)$alkoxy, $(C_1-C_4)$alkylthio, amino, nitro, cyano, oxo, carboxy, $(C_1-C_6)$alkyloxycarbonyl, mono-N— or di-N,N—$(C_1-C_6)$alkylamino, said $(C_1-C_6)$alkyl or $(C_2-C_6)$ alkenyl substituents are also optionally substituted with from one to nine fluorines;

$R_{V-4}$ is cyano, formyl, $W_{V-1}Q_{V-1}$, $W_{V-1}V_{V-1}$, $(C_1-C_4)$alkylene $V_{V-1}$ or $V_{V-2}$;

wherein $W_{V-1}$ is carbonyl, thiocarbonyl, SO or $SO_2$, wherein $Q_{V-1}$ a fully saturated, partially unsaturated or fully unsaturated one to six membered straight or branched carbon chain wherein the carbons may optionally be replaced with one heteroatom selected from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono-, or di-substituted with oxo, and said carbon chain is optionally mono-substituted with $V_{V-1}$;

wherein $V_{V-1}$ is a partially saturated, fully saturated or fully unsaturated three to six membered ring optionally having one to two heteroatoms selected independently from oxygen, sulfur and nitrogen, or a bicyclic ring consisting of two fused partially saturated, fully saturated or fully unsaturated three to six membered rings, taken independently, optionally having one to four heteroatoms selected independently from nitrogen, sulfur and oxygen;

wherein said $V_{V-1}$ substituent is optionally mono-, di-, tri-, or tetra-substituted independently with halo, $(C_1-C_6)$alkyl, $(C_1-C_6)$alkoxy, hydroxy, oxo, amino, nitro, cyano, $(C_1-C_6)$alkyloxycarbonyl, mono-N— or di-N,N—$(C_1-C_6)$alkylamino wherein said $(C_1-C_6)$alkyl substituent is optionally mono-substituted with oxo, said $(C_1-C_6)$alkyl substituent is also optionally substituted with from one to nine fluorines;

wherein $V_{V-2}$ is a partially saturated, fully saturated or fully unsaturated five to seven membered ring containing one to four heteroatoms selected independently from oxygen, sulfur and nitrogen;

wherein said $V_{V-2}$ substituent is optionally mono-, di- or tri-substituted independently with halo, $(C_1-C_2)$alkyl, $(C_1-C_2)$alkoxy, hydroxy, or oxo wherein said $(C_1-C_2)$alkyl optionally has from one to five fluorines; and wherein $R_{V-4}$ does not include oxycarbonyl linked directly to the $C^4$ nitrogen;

wherein either $R_{V-3}$ must contain $V_V$ or $R_{V-4}$ must contain $V_{V-1}$;

$R_{V-5}$, $R_{V-6}$, $R_{V-7}$ and $R_{V-8}$ are independently hydrogen, a bond, nitro or halo wherein said bond is substituted with $T_V$ or a partially saturated, fully saturated or fully unsaturated $(C_1-C_{12})$ straight or branched carbon chain wherein carbon may optionally be replaced with one or two heteroatoms selected independently from oxygen, sulfur and nitrogen, wherein said carbon atoms are optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono- or di-substituted with oxo, and said carbon chain is optionally mono-substituted with $T_V$;

wherein $T_V$ is a partially saturated, fully saturated or fully unsaturated three to twelve membered ring optionally having one to four heteroatoms selected independently from oxygen, sulfur and nitrogen, or a bicyclic ring consisting of two fused partially saturated, fully saturated or fully unsaturated three to six membered rings, taken independently, optionally having one to four heteroatoms selected independently from nitrogen, sulfur and oxygen;

wherein said $T_V$ substituent is optionally mono-, di- or tri-substituted independently with halo, $(C_1-C_6)$alkyl, $(C_2-C_6)$alkenyl, hydroxy, $(C_1-C_6)$alkoxy, $(C_1-C_6)$alkylthio, amino, nitro, cyano, oxo, carboxy, $(C_1-C_6)$alkyloxycarbonyl, mono-N— or di-N,N—$(C_1-C_6)$alkylamino wherein said $(C_1-C_6)$alkyl substituent is optionally mono-, di- or tri-substituted independently with hydroxy, $(C_1-C_6)$alkoxy, $(C_1-C_4)$alkylthio, amino, nitro, cyano, oxo, carboxy, $(C_1-C_6)$alkyloxycarbonyl, mono-N— or di-N,N—$(C_1-C_6)$alkylamino, said $(C_1-C_6)$alkyl substituent also optionally has from one to nine fluorines;

wherein $R_{V-5}$ and $R_{V-6}$, or $R_{V-6}$ and $R_{V-7}$ and/or $R_{V-7}$ and $R_{V-8}$ may also be taken together and can form at least one ring that is a partially saturated or fully unsaturated four to eight membered ring optionally having one to three heteroatoms independently selected from nitrogen, sulfur and oxygen;

wherein said rings formed by $R_{V-5}$ and $R_{V-6}$, or $R_{V-6}$ and $R_{V-7}$ and/or $R_{V-7}$ and $R_{V-8}$ are optionally mono-, di- or tri-substituted independently with halo, $(C_1-C_6)$alkyl, $(C_1-C_4)$alkylsulfonyl, $(C_2-C_6)$alkenyl, hydroxy, $(C_1-C_6)$alkoxy, $(C_1-C_4)$alkylthio, amino, nitro, cyano, oxo, carboxy, $(C_1-C_6)$alkyloxycarbonyl, mono-N— or di-N,N—$(C_1-C_6)$alkylamino wherein said $(C_1-C_6)$alkyl substituent is optionally mono-, di- or tri-substituted independently with hydroxy, $(C_1-C_6)$alkoxy, $(C_1-C_4)$alkylthio, amino, nitro, cyano, oxo, carboxy, $(C_1-C_6)$alkyloxycarbonyl, mono-N— or di-N,N—$(C_1-C_6)$alkylamino, said $(C_1-C_6)$alkyl substituent also optionally has from one to nine fluorines.

Compounds of Formula V are disclosed in commonly assigned pending U.S. patent application Ser. No. 09/391,313 the complete disclosure of which is herein incorporated by reference.

In a preferred embodiment, the CETP inhibitor is selected from one of the following compounds of Formula V:

[2S,4S]4-[(3,5-bis-trifluoromethyl-benzyl)-formyl-amino]-2-cyclopropyl-6-trifluoromethyl-3,4-dihydro-2H-quinoline-1-carboxylic acid isopropyl ester;

[2S,4S]4-[(3,5-bis-trifluoromethyl-benzyl)-formyl-amino]-2-cyclopropyl-6-trifluoromethyl-3,4-dihydro-2H-quinoline-1-carboxylic acid propyl ester;

[2S,4S]4-[acetyl-(3,5-bis-trifluoromethyl-benzyl)-amino]-2-cyclopropyl-6-trifluoromethyl-3,4-dihydro-2H-quinoline-1-carboxylic acid tert-butyl ester;

[2R,4S]4-[acetyl-(3,5-bis-trifluoromethyl-benzyl)-amino]-2-ethyl-6-trifluoromethyl-3,4-dihydro-2H-quinoline-1-carboxylic acid isopropyl ester;

[2R,4S]4-[acetyl-(3,5-bis-trifluoromethyl-benzyl)-amino]-2-methyl-6-trifluoromethyl-3,4-dihydro-2H-quinoline-1-carboxylic acid ethyl ester,

[2S,4S]4-[1-(3,5-bis-trifluoromethyl-benzyl)-ureido]-2-cyclopropyl-6-trifluoromethyl-3,4-dihydro-2H-quinoline-1-carboxylic acid isopropyl ester;

[2R,4S]4-[acetyl-(3,5-bis-trifluoromethyl-benzyl)-amino]-2-ethyl-6-trifluoromethyl-3,4-dihydro-2H-quinoline-1-carboxylic acid ethyl ester;

[2S,4S]4-[acetyl-(3,5-bis-trifluoromethyl-benzyl)-amino]-2-methoxymethyl-6-trifluoromethyl 3,4-dihydro-2H-quinoline-1-carboxylic acid isopropyl ester;

[2S,4S]4-[acetyl-(3,5-bis-trifluoromethyl-benzyl)-amino]-2-cyclopropyl-6-trifluoromethyl-3,4-dihydro-2H-quinoline-1-carboxylic acid propyl ester;

[2S,4S]4-[acetyl-(3,5-bis-trifluoromethyl-benzyl)-amino]-2-cyclopropyl-6-trifluoromethyl-3,4-dihydro-2H-quinoline-1-carboxylic acid ethyl ester;

[2R,4S]4-[(3,5-bis-trifluoromethyl-benzyl)-formyl-amino]-2-ethyl-6-trifluoromethyl-3,4-dihydro-2H-quinoline-1-carboxylic acid isopropyl ester,

[2R,4S]4-[(3,5-bis-trifluoromethyl-benzyl)-formyl-amino]-2-methyl-6-trifluoromethyl-3,4-dihydro-2H-quinoline-1-carboxylic acid ethyl ester;

[2S,4S]4-[acetyl-(3,5-bis-trifluoromethyl-benzyl)-amino]-2-cyclopropyl-6-trifluoromethyl-3,4-dihydro-2H-quinoline-1-carboxylic acid isopropyl ester;

[2R,4S]4-[(3,5-bis-trifluoromethyl-benzyl)-formyl-amino]-2-ethyl-6-trifluoromethyl-3,4-dihydro-2H-quinoline-1-carboxylic acid ethyl ester;

[2S,4S]4-[(3,5-bis-trifluoromethyl-benzyl)-formyl-amino]-2-cyclopropyl-6-trifluoromethyl-3,4-dihydro-2H-quinoline-1-carboxylic acid ethyl ester;

[2R,4S]4-[(3,5-bis-trifluoromethyl-benzyl)-formyl-amino]-2-methyl-6-trifluoromethyl-3,4-dihydro-2H-quinoline-1-carboxylic acid isopropyl ester; and

[2R,4S]4-[acetyl-(3,5-bis-trifluoromethyl-benzyl)-amino]-2-methyl-6-trifluoromethyl-3,4-dihydro-2H-quinoline-1-carboxylic acid isopropyl ester.

Another class of CETP inhibitors that finds utility with the present invention consists of cycloalkano-pyridines having the Formula VI

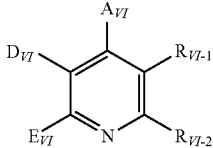

Formula VI and pharmaceutically acceptable salts, enantiomers, or stereoisomers of said compounds;

in which $A_{VI}$ denotes an aryl containing 6 to 10 carbon atoms, which is optionally substituted with up to five identical or different substituents in the form of a halogen, nitro, hydroxyl, trifluoromethyl, trifluoromethoxy or a straight-chain or branched alkyl, acyl, hydroxyalkyl or alkoxy containing up to 7 carbon atoms each, or in the form of a group according to the formula —$NR_{VI-3}R_{VI-4}$, wherein $R_{VI-3}$ and $R_{VI-4}$ are identical or different and denote a hydrogen, phenyl or a straight-chain or branched alkyl containing up to 6 carbon atoms, $D_{VI}$ denotes an aryl containing 6 to 10 carbon atoms, which is optionally substituted with a phenyl, nitro, halogen, trifluoromethyl or trifluoromethoxy, or a radical according to the formula $R_{VI-5}$-$L_{VI}$-,

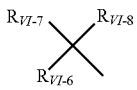

or $R_{VI-9}$-$T_{VI}$-$V_{VI}$—$X_{VI}$, wherein $R_{VI-5}$, $R_{VI-6}$ and $R_{VI-9}$ denote, independently from one another, a cycloalkyl containing 3 to 6 carbon atoms, or an aryl containing 6 to 10 carbon atom or a 5- to 7-membered, optionally benzo-condensed, saturated or unsaturated, mono-, bi- or tricyclic heterocycle containing up to 4 heteroatoms from the series of S, N and/or O, wherein the rings are optionally substituted, in the case of the nitrogen-containing rings also via the N function, with up to five identical or different substituents in the form of a halogen, trifluoromethyl, nitro, hydroxyl, cyano, carboxyl, trifluoromethoxy, a straight-chain or branched acyl, alkyl, alkylthio, alkylalkoxy, alkoxy or alkoxycarbonyl containing up to 6 carbon atoms each, an aryl or trifluoromethyl-substituted aryl containing 6 to 10 carbon atoms each, or an optionally benzo-condensed, aromatic 5- to 7-membered heterocycle containing up to 3 heteroatoms from the series of S, N and/or O, and/or in the form of a group according to the formula —$OR_{VI-10}$, —$SR_{VI-11}$, —$SO_2R_{VI-12}$ or —$NR_{VI-13}R_{VI-14}$, wherein $R_{VI-10}$, $R_{VI-11}$ and $R_{VI-12}$ denote, independently from one another, an aryl containing 6 to 10 carbon atoms, which is in turn substituted with up to two identical or different substituents in the form of a phenyl, halogen or a straight-chain or branched alkyl containing up to 6 carbon atoms, $R_{VI-13}$ and $R_{VI-14}$ are identical or different and have the meaning of $R_{VI-3}$ and $R_{IV-4}$ given above, or $R_{VI-5}$ and/or $R_{VI-6}$ denote a radical according to the formula

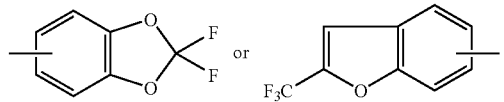

$R_{VI-7}$ denotes a hydrogen or halogen, and $R_{VI-8}$ denotes a hydrogen, halogen, azido, trifluoromethyl, hydroxyl, trifluoromethoxy, a straight-chain or branched alkoxy or alkyl containing up to 6 carbon atoms each, or a radical according to the formula

—$NR_{VI-15}R_{VI-16}$, wherein $R_{VI-15}$ and $R_{VI-16}$ are identical or different and have the meaning of $R_{VI-3}$ and $R_{VI-4}$ given above, or $R_{VI-7}$ and $R_{VI-8}$ together form a radical according to the formula =O or =$NR_{VI-7}$, wherein $R_{VI-17}$ denotes a hydrogen or a straight-chain or branched alkyl, alkoxy or acyl containing up to 6 carbon atoms each, $L_{VI}$ denotes a straight-chain or branched alkylene or alkenylene chain containing up to 8 carbon atoms each, which are optionally substituted with up to two hydroxyl groups, $T_{VI}$ and $X_{VI}$ are identical or different and denote a straight-chain or branched alkylene chain containing up to 8 carbon atoms, or $T_{VI}$ or $X_{VI}$ denotes a bond, $V_{VI}$ denotes an oxygen or sulfur atom or an —$NR_{VI-18}$ group, wherein $R_{VI-18}$ denotes a hydrogen or a straight-chain or branched alkyl containing up to 6 carbon atoms or a phenyl, $E_{VI}$ denotes a cycloalkyl containing 3 to 8 carbon atoms, or a straight-chain or branched alkyl containing up to 8 carbon atoms, which is optionally substituted with a cycloalkyl containing 3 to 8 carbon atoms or a hydroxyl, or a phenyl, which is optionally substituted with a halogen or trifluoromethyl, $R_{VI-1}$ and $R_{VI-2}$ together form a straight-chain or branched alkylene chain containing up to 7 carbon atoms, which must be substituted with a carbonyl group and/or a radical according to the formula

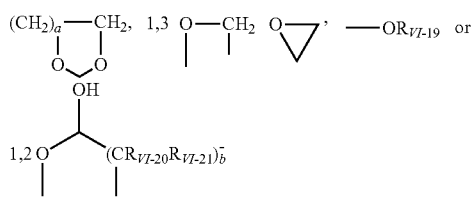

wherein a and b are identical or different and denote a number equaling 1, 2 or 3, $R_{VI-19}$ denotes a hydrogen atom, a cycloalkyl containing 3 to 7 carbon atoms, a straight-chain or branched silylalkyl containing up to 8 carbon atoms, or a straight-chain or branched alkyl containing up to 8 carbon atoms, which is optionally substituted with a hydroxyl, a straight-chain or a branched alkoxy containing up to 6 carbon atoms or a phenyl, which may in turn be substituted with a halogen, nitro, trifluoromethyl, trifluoromethoxy or phenyl or tetrazole-substituted phenyl, and an alkyl that is optionally substituted with a group according to the formula —$OR_{VI-22}$, wherein $R_{VI-22}$ denotes a straight-chain or branched acyl containing up to 4 carbon atoms or benzyl, or $R_{VI-19}$ denotes a straight-chain or branched acyl containing up to 20 carbon atoms or benzoyl, which is optionally substituted with a halogen, trifluoromethyl, nitro or trifluoromethoxy, or a straight-chain or branched fluoroacyl containing up to 8 carbon atoms, $R_{VI-20}$ and $R_{VI-21}$ are identical or different and denote a hydrogen, phenyl or a straight-chain or branched alkyl containing up to 6 carbon atoms, or $R_{VI-20}$ and $R_{VI-21}$ together form a 3- to 6-membered carbocyclic ring, and a the carbocyclic rings formed are optionally substituted, optionally also geminally, with up to six identical or different substituents in the form of trifluoromethyl, hydroxyl, nitrile, halogen, carboxyl, nitro, azido, cyano, cycloalkyl or cycloalkyloxy containing 3 to 7 carbon atoms each, a straight-chain or branched alkoxycarbonyl, alkoxy or alkylthio containing up to 6 carbon atoms each, or a straight-chain or branched alkyl containing up to 6 carbon atoms, which is in turn substituted with up to two identical or different substituents in the form of a hydroxyl, benzyloxy, trifluoromethyl, benzoyl, a straight-chain or branched alkoxy, oxyacyl or carboxyl containing up to 4 carbon atoms each and/or a phenyl, which may in turn be substituted with a halogen, trifluoromethyl or trifluoromethoxy, and/or the carbocyclic rings formed are optionally substituted, also geminally, with up to five identical or different substituents in the form of a phenyl, benzoyl, thiophenyl or sulfonylbenzyl, which in turn are optionally substituted with a halogen, trifluoromethyl, trifluoromethoxy or nitro, and/or optionally in the form of a radical according to the formula

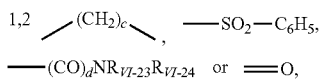

wherein c is a number equaling 1, 2, 3 or 4, d is a number equaling 0 or 1, $R_{VI-23}$ and $R_{VI-24}$ are identical or different and denote a hydrogen, cycloalkyl containing 3 to 6 carbon atoms, a straight-chain or branched alkyl containing up to 6 carbon atoms, benzyl or phenyl, which is optionally substituted with up to two identical or different substituents in the form of halogen, trifluoromethyl, cyano, phenyl or nitro, and/or the carbocyclic rings formed are optionally substituted with a spiro-linked radical according to the formula

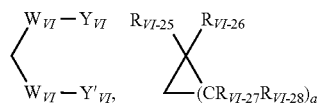

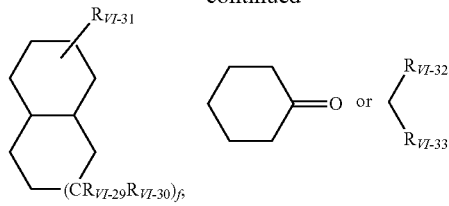

wherein $W_{VI}$ denotes either an oxygen atom or a sulfur atom, $Y_{VI}$ and $Y'_{VI}$ together form a 2- to 6-membered straight-chain or branched alkylene chain, e is a number equaling 1, 2, 3, 4, 5, 6 or 7, f is a number equaling 1 or 2, $R_{VI-25}$, $R_{VI-26}$, $R_{VI-27}$, $R_{VI-28}$, $R_{VI-29}$, $R_{VI-30}$ and $R_{VI-31}$ are identical or different and denote a hydrogen, trifluoromethyl, phenyl, halogen or a straight-chain or branched alkyl or alkoxy containing up to 6 carbon atoms each, or $R_{VI-25}$ and $R_{VI-26}$ or $R_{VI-27}$ and $R_{VI-28}$ each together denote a straight-chain or branched alkyl chain containing up to 6 carbon atoms or $R_{VI-25}$ and $R_{VI-26}$ or $R_{VI-27}$ and $R_{VI-28}$ each together form a radical according to the formula

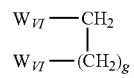

wherein $W_{VI}$ has the meaning given above, g is a number equaling 1, 2, 3, 4, 5, 6 or 7, $R_{VI-32}$ and $R_{VI-33}$ together form a 3- to 7-membered heterocycle, which contains an oxygen or sulfur atom or a group according to the formula SO, $SO_2$ or —$NR_{VI-34}$, wherein $R_{VI-34}$ denotes a hydrogen atom, a phenyl, benzyl, or a straight-chain or branched alkyl containing up to 4 carbon atoms, and salts and N oxides thereof, with the exception of 5(6H)-quinolones, 3-benzoyl-7,8-dihydro-2,7,7-trimethyl-4-phenyl.

Compounds of Formula VI are disclosed in European Patent Application No. EP 818448 A1, the complete disclosure of which is herein incorporated by reference.

In a preferred embodiment, the CETP inhibitor is selected from one of the following compounds of Formula VI:

2-cyclopentyl-4-(4-fluorophenyl)-7,7-dimethyl-3-(4-trifluoromethylbenzoyl)-4,6,7,8-tetrahydro-1H-quinolin-5-one;

2-cyclopentyl-4-(4-fluorophenyl)-7,7-dimethyl-3-(4-trifluoromethylbenzoyl)-7,8-dihydro-6H-quinolin-5-one;

[2-cyclopentyl-4-(4-fluorophenyl)-5-hydroxy-7,7-dimethyl-5,6,7,8-tetrahydroquinolin-3-yl]-(4-trifluoromethylphenyl)-methanone;

[5-(t-butyldimethylsilanyloxy)-2-cyclopentyl-4-(4-fluorophenyl)-7,7-dimethyl-5,6,7,8-tetrahydroquinolin-3-yl]-(4-trifluoromethylphenyl)-methanone;

[5-(t-butyldimethylsilanyloxy)-2-cyclopentyl-4-(4-fluorophenyl)-7,7-dimethyl-5,6,7,8-tetrahydroquinolin-3-yl]-(4-trifluoromethylphenyl)-methanol;

5-(t-butyldimethylsilanyloxy)-2-cyclopentyl-4-(4-fluorophenyl)-3-[fluoro-(4-trifluoromethylphenyl)-methyl]-7,7-dimethyl-5,6,7,8-tetrahydroquinoline;

2-cyclopentyl-4-(4-fluorophenyl)-3-[fluoro-(4-trifluoromethylphenyl)-methyl]-7,7-dimethyl-5,6,7,8-tetrahydroquinolin-5-ol.

Another class of CETP inhibitors that finds utility with the present invention consists of substituted-pyridines having the Formula VII

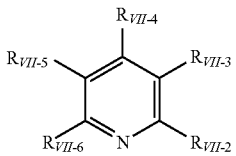

Formula VII or a pharmaceutically acceptable salt or tautomer thereof, wherein $R_{VII-2}$ and $R_{VII-6}$ are independently selected from the group consisting of hydrogen, hydroxy, alkyl, fluorinated alkyl, fluorinated aralkyl, chlorofluorinated alkyl, cycloalkyl, heterocyclyl, aryl, heteroaryl, alkoxy, alkoxyalkyl, and alkoxycarbonyl; provided that at least one of $RV_{II-2}$ and $R_{VII-6}$ is fluorinated alkyl, chlorofluorinated alkyl or alkoxyalkyl;

$R_{VII-3}$ is selected from the group consisting of hydroxy, amido, arylcarbonyl, heteroarylcarbonyl, hydroxymethyl —CHO, —$CO_2R_{VII-7}$, wherein $R_{III-7}$ is selected from the group consisting of hydrogen, alkyl and cyanoalkyl; and

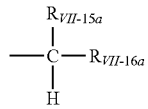

wherein $R_{VII-15a}$ is selected from the group consisting of hydroxy, hydrogen, halogen, alkylthio, alkenylthio, alkynylthio, arylthio, heteroarylthio, heterocyclylthio, alkoxy, alkenoxy, alkynoxy, aryloxy, heteroaryloxy and heterocyclyloxy, and $R_{VII-16a}$ is selected from the group consisting of alkyl, haloalkyl, alkenyl, haloalkenyl, alkynyl, haloalkynyl, aryl, heteroaryl, and heterocyclyl, arylalkoxy, trialkylsilyloxy;

$R_{VII-4}$ is selected from the group consisting of hydrogen, hydroxy, halogen, alkyl, alkenyl, alkynyl, cycloalkyl, cycloalkenyl, haloalkyl, haloalkenyl, haloalkynyl, aryl, heteroaryl, heterocyclyl, cycloalkylalkyl, cycloalkenylalkyl, aralkyl, heteroarylalkyl, heterocyclylalkyl, cycloalkylalkenyl, cycloalkenylalkenyl, aralkenyl, hetereoarylalkenyl, heterocyclylalkenyl, alkoxy, alkenoxy, alkynoxy, aryloxy, heteroaryloxy, heterocyclyloxy, alkanoyloxy, alkenoyloxy, alkynoyloxy, aryloyloxy, heteroaroyloxy, heterocyclyloyloxy, alkoxycarbonyl, alkenoxycarbonyl, alkynoxycarbonyl, aryloxycarbonyl, heteroaryloxycarbonyl, heterocyclyloxycarbonyl, thio, alkylthio, alkenylthio, alkynylthio, arylthio, heteroarylthio, heterocyclylthio, cycloalkylthio, cycloalkenylthio, alkylthioalkyl, alkenylthioalkyl, alkynylthioalkyl, arylthioalkyl, heteroarylthioalkyl, heterocyclylthioalkyl, alkylthioalkenyl, alkenylthioalkenyl, alkynylthioalkenyl, arylthioalkenyl, heteroarylthioalkenyl, heterocyclythioalkenyl, alkylamino, alkenylamino, alkynylamino, arylamino, heteroarylamino, heterocyclylamino, aryldialkylamino, diarylamino, diheteroarylamino, alkylarylamino, alkylheteroarylamino, arylheteroarylamino, trialkylsilyl, trialkenylsilyl, triarylsilyl, —CO(O)N($RV_{II-8a}R_{VII-8b}$) wherein $R_{VII-8a}$ and $R_{VII-8b}$ are independently selected from the group consisting of alkyl, alkenyl, alkynyl, aryl, heteroaryl and heterocyclyl, —$SO_2R_{VII-9}$, wherein $R_{VII-9}$ is selected from the group consisting of hydroxy, alkyl, alkenyl, alkynyl, aryl, heteroaryl and heterocyclyl, —OP(O)(O$R_{VII-10a}$) (O$R_{VII-10b}$), wherein $R_{VII-10a}$ and $R_{VII-10b}$ are independently selected from the group consisting of hydrogen, hydroxy, alkyl, alkenyl, alkynyl, aryl, heteroaryl and heterocyclyl, and —OP(S) (O$R_{VII-11a}$) (O$R_{VII-11b}$), wherein $R_{VII-11a}$ and $R_{VII-11b}$ are independently selected from the group consisting of alkyl, alkenyl, alkynyl, aryl, heteroaryl and heterocyclyl;

$R_{VII-5}$ is selected from the group consisting of hydrogen, hydroxy, halogen, alkyl, alkenyl, alkynyl, cycloalkyl, cycloalkenyl, haloalkyl, haloalkenyl, haloalkynyl, aryl, heteroaryl, heterocyclyl, alkoxy, alkenoxy, alkynoxy, aryloxy, heteroaryloxy, heterocyclyloxy, alkylcarbonyloxyalkyl, alkenylcarbonyloxyalkyl, alkynylcarbonyloxyalkyl, arylcarbonyloxyalkyl, heteroarylcarbonyloxyalkyl, heterocyclylcarbonyloxyalkyl, cyclcalkylalkyl, cycloalkenylalkyl, aralkyl, heteroarylalkyl, heterocyclylalkyl, cycloalkylalkenyl, cycloalkenylalkenyl, aralkenyl, heteroarylalkenyl, heterocyclylalkenyl, alkylthioalkyl, cycloalkylthioalkyl, alkenylthioalkyl, alkynylthioalkyl, arylthioalkyl, heteroarylthioalkyl, heterocyclylthioalkyl, alkylthioalkenyl, alkenylthioalkenyl, alkynylthioalkenyl, arylthioalkenyl, heteroarylthioalkenyl, heterocyclylthioalkenyl, alkoxyalkyl, alkenoxyalkyl, alkynoxylalkyl, aryloxyalkyl, heteroaryloxyalkyl, heterocyclyloxyalkyl, alkoxyalkenyl, alkenoxyalkenyl, alkynoxyalkenyl, aryloxyalkenyl, heteroaryloxyalkenyl, heterocyclyloxyalkenyl, cyano, hydroxymethyl, —$CO_2R_{VII-14}$, wherein $R_{VII-14}$ is selected from the group consisting of alkyl, alkenyl, alkynyl, aryl, heteroaryl and heterocyclyl;

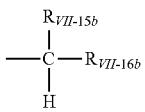

wherein $R_{VII-15b}$ is selected from the group consisting of hydroxy, hydrogen, halogen, alkylthio, alkenylthio, alkynylthio, arylthio, heteroarylthio, heterocyclylthio, alkoxy, alkenoxy, alkynoxy, aryloxy, heteroaryloxy, heterocyclyloxy, aroyloxy, and alkylsulfonyloxy, and $R_{VII-16b}$ is selected form the group consisting of alkyl, alkenyl, alkynyl, aryl, heteroaryl, heterocyclyl, arylalkoxy, and trialkylsilyloxy;

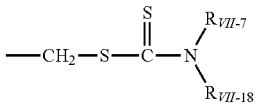

wherein $R_{VII-17}$ and $R_{VII-18}$ are independently selected from the group consisting of alkyl, cycloalkyl, alkenyl, alkynyl, aryl, heteroaryl and heterocyclyl;

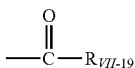

wherein $R_{VII-19}$ is selected from the group consisting of alkyl, cycloalkyl, alkenyl, alkynyl, aryl, heteroaryl, heterocyclyl, —$SR_{VII-20}$, —$OR_{VII-21}$, and —$R_{VII-22}CO_2R_{VII-23}$, wherein $R_{VII-20}$ is selected from the group consisting of alkyl, alkenyl, alkynyl, aryl, heteroaryl, heterocyclyl, aminoalkyl, aminoalkenyl, aminoalkynyl, aminoaryl, aminoheteroaryl, aminoheterocyclyl, alkylheteroarylamino, arylheteroarylamino, $R_{VII-21}$ is selected from the group consisting of alkyl, alkenyl, alkynyl, aryl, heteroaryl, and heterocyclyl, $R_{VII-22}$ is selected from the group consisting of alkylene or arylene, and $R_{VII-23}$ is selected from the group consisting of alkyl, alkenyl, alkynyl, aryl, heteroaryl, and heterocyclyl;

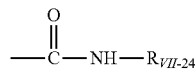

wherein $R_{VII-24}$ is selected from the group consisting of hydrogen, alkyl, cycloalkyl, alkenyl, alkynyl, aryl, heteroaryl, heterocyclyl, aralkyl, aralkenyl, and aralkynyl;

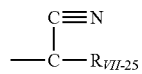

wherein $R_{VII-25}$ is heterocyclylidenyl;

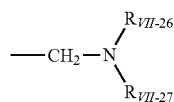

wherein $R_{VII-26}$ and $R_{VII-27}$ are independently selected from the group consisting of hydrogen, alkyl, cycloalkyl, alkenyl, alkynyl, aryl, heteroaryl, and heterocyclyl;

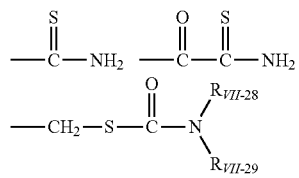

wherein $R_{VII-28}$ and $R_{VII-29}$ are independently selected from the group consisting of hydrogen, alkyl, cycloalkyl, alkenyl, alkynyl, aryl, heteroaryl, and heterocyclyl;

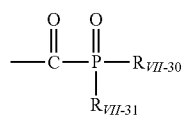

wherein $R_{VII-30}$ and $R_{VII-31}$ are independently alkoxy, alkenoxy, alkynoxy, aryloxy, heteroaryloxy, and heterocyclyloxy; and

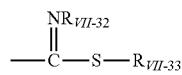

wherein $R_{VII-32}$ and $R_{VII-33}$ are independently selected from the group consisting of hydrogen, alkyl, cycloalkyl, alkenyl, alkynyl, aryl, heteroaryl, and heterocyclyl;

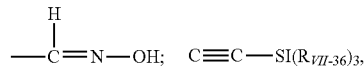

wherein $R_{VII-36}$ is selected from the group consisting of alkyl, alkenyl, aryl, heteroaryl and heterocyclyl;

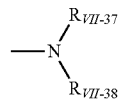

wherein $R_{VII-3}$ and $R_{VII-38}$ are independently selected from the group consisting of hydrogen, alkyl, cycloalkyl, alkenyl, alkynyl, aryl, heteroaryl, and heterocyclyl;

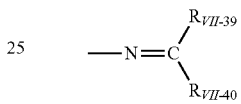

wherein $R_{VII-39}$ is selected from the group consisting of hydrogen, alkoxy, alkenoxy, alkynoxy, aryloxy, heteroaryloxy, heterocyclyloxy, alkylthio, alkenylthio, alkynylthio, arylthio, heteroarylthio and heterocyclylthio, and $R_{VII-40}$ is selected from the group consisting of haloalkyl, haloalkenyl, haloalkynyl, haloaryl, haloheteroaryl, haloheterocyclyl, cycloalkyl, cycloalkenyl, heterocyclylalkoxy, heterocyclylalkenoxy, heterocyclylalkynoxy, alkylthio, alkenylthio, alkynylthio, arylthio, heteroarylthio and heterocyclylthio;

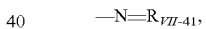

wherein $R_{VII-41}$ is heterocyclylidenyl;

wherein $R_{VII-42}$ is selected from the group consisting of hydrogen, alkyl, alkenyl, alkynyl, aryl, heteroaryl, and heterocyclyl, and $R_{VII-43}$ is selected from the group consisting of hydrogen, alkyl, alkenyl, alkynyl, aryl, heteroaryl, heterocyclyl, cycloalkyl, cycloalkenyl, haloalkyl, haloalkenyl, haloalkynyl, haloaryl, haloheteroaryl, and haloheterocyclyl;

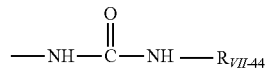

wherein $R_{VI-44}$ is selected from the group consisting of hydrogen, alkyl, cycloalkyl, alkenyl, alkynyl, aryl, heteroaryl and heterocyclyl;

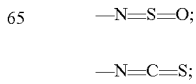

—N=C=O;

—N₃;

—SR$_{VII\text{-}45}$ wherein R$_{VII\text{-}45}$ is selected from the group consisting of hydrogen, alkyl, alkenyl, alkynyl, aryl, heteroaryl, heterocyclyl, haloalkyl, haloalkenyl, haloalkynyl, haloaryl, haloheteroaryl, haloheterocyclyl, heterocyclyl, cycloalkylalkyl, cycloalkenylalkyl, aralkyl, heteroarylalkyl, heterocyclylalkyl, cycloalkylalkenyl, cycloalkenylalkenyl, aralkenyl, heteroarylalkenyl, heterocyclylalkenyl, alkylthioalkyl, alkenylthioalkyl, alkynylthioalkyl, arylthioalkyl, heteroarylthioalkyl, heterocyclylthioalkyl, alkylthioalkenyl, alkenylthioalkenyl, alkynylthioalkenyl, arylthioalkenyl, heteroarylthioalkenyl, heterocyclylthioalkenyl, aminocarbonylalkyl, aminocarbonylalkenyl, aminocarbonylalkynyl, aminocarbonylaryl, aminocarbonylheteroaryl, and aminocarbonylheterocyclyl, —SR$_{VII\text{-}46}$, and —CH$_2$R$_{VII\text{-}47}$, wherein R$_{VII\text{-}46}$ is selected from the group consisting of alkyl, alkenyl, alkynyl, aryl, heteroaryl and heterocyclyl, and R$_{VII\text{-}47}$ is selected from the group consisting of hydrogen, alkyl, alkenyl, alkynyl, aryl, heteroaryl and heterocyclyl; and

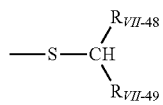

wherein R$_{VII\text{-}48}$ is selected from the group consisting of hydrogen, alkyl, cycloalkyl, alkenyl, alkynyl, aryl, heteroaryl and heterocyclyl, and
R$_{VII\text{-}49}$ is selected from the group consisting of alkoxy, alkenoxy, alkynoxy, aryloxy, heteroaryloxy, heterocyclyloxy, haloalkyl, haloalkenyl, haloalkynyl, haloaryl, haloheteroaryl and haloheterocyclyl;

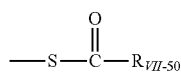

wherein R$_{VII\text{-}50}$ is selected from the group consisting of hydrogen, alkyl, cycloalkyl, alkenyl, alkynyl, aryl, heteroaryl, heterocyclyl, alkoxy, alkenoxy, alkynoxy, aryloxy, heteroaryloxy and heterocyclyloxy;

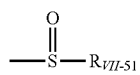

wherein R$_{VII\text{-}51}$ is selected from the group consisting of alkyl, alkenyl, alkynyl, aryl, heteroaryl, heterocyclyl, haloalkyl, haloalkenyl, haloalkynyl, haloaryl, haloheteroaryl and haloheterocyclyl; and

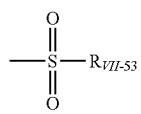

wherein R$_{VII\text{-}53}$ is selected from the group consisting of alkyl, alkenyl, alkynyl, aryl, heteroaryl and heterocyclyl;

provided that when R$_{VII\text{-}5}$ is selected from the group consisting of heterocyclylalkyl and heterocyclylalkenyl, the heterocyclyl radical of the corresponding heterocyclylalkyl or heterocyclylalkenyl is other than δ-lactone; and provided that when R$_{VII\text{-}4}$ is aryl, heteroaryl or heterocyclyl, and one of R$_{VII\text{-}2}$ and R$_{VII\text{-}6}$ is trifluoromethyl, then the other of R$_{VII\text{-}2}$ and R$_{VII\text{-}6}$ is difluoromethyl.

Compounds of Formula V$_{II}$ are disclosed in WO 9941237-A1, the complete disclosure of which is incorporated by reference.

In a preferred embodiment, the CETP inhibitor is selected from the following compounds of Formula VII: Dimethyl 5,5'-dithiobis[2-difluoromethyl-4-(2-methylpropyl)-6-(trifluoromethyl)-3-pyridine-carboxylate].

Another class of CETP inhibitors that finds utility with the present invention consists of substituted pyridines and biphenyls having the Formula VIII

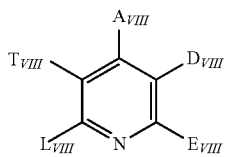

Formula VIII or a pharmaceutically acceptable salt, enantiomers, or stereoisomers thereof, in which A$_{VIII}$ stands for aryl with 6 to 10 carbon atoms, which is optionally substituted up to 3 times in an identical manner or differently by halogen, hydroxy, trifluoromethyl, trifluoromethoxy, or by straight-chain or branched alkyl, acyl, or alkoxy with up to 7 carbon atoms each, or by a group of the formula —NR$_{VIII\text{-}1}$R$_{VIII\text{-}2}$, wherein R$_{VIII\text{-}1}$ and R$_{VIII\text{-}2}$ are identical or different and denote hydrogen, phenyl, or straight-chain or branched alkyl with up to 6 carbon atoms, D$_{VIII}$ stands for straight-chain or branched alkyl with up to 8 carbon atoms, which is substituted by hydroxy, E$_{VIII}$ and L$_{VIII}$ are either identical or different and stand for straight-chain or branched alkyl with up to 8 carbon atoms, which is optionally substituted by cycloalkyl with 3 to 8 carbon atoms, or stands for cycloalkyl with 3 to 8 carbon atoms, or E$_{VIII}$ has the above-mentioned meaning and L$_{VIII}$ in this case stands for aryl with 6 to 10 carbon atoms, which is optionally substituted up to 3 times in an identical manner or differently by halogen, hydroxy, trifluoromethyl, trifluoromethoxy, or by straight-chain or branched alkyl, acyl, or alkoxy with up to 7 carbon atoms each, or by a group of the formula —NR$_{VIII\text{-}3}$R$_{VIII\text{-}4}$, wherein R$_{VIII\text{-}3}$ and R$_{VIII\text{-}4}$ are identical or different and have the meaning given above for R$_{VIII\text{-}1}$ and R$_{VIII\text{-}2}$, or E$_{VIII}$ stands for straight-chain or branched alkyl with up to 8 carbon atoms, or stands for aryl with 6 to 10 carbon atoms, which is optionally substituted up to 3 times in an identical manner or differently by halogen, hydroxy, trifluoromethyl, trifluoromethoxy, or by straight-chain or branched alkyl, acyl, or alkoxy with up to 7 carbon atoms each, or by a group of the formula —NR$_{VIII-5}$R$_{VIII-6}$, wherein R$_{VIII-5}$ and R$_{VIII-6}$ are identical or different and have the meaning given above for R$_{VIII-1}$ and R$_{VIII-2}$, and L$_{VIII}$ in this case stands for straight-chain or branched alkoxy with up to 8 carbon atoms or for cycloalkyloxy with 3 to 8 carbon atoms, T$_{VIII}$ stands for a radical of the formula

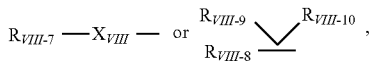

wherein

R$_{VIII-7}$ and R$_{VIII-8}$ are identical or different and denote cycloalkyl with 3 to 8 carbon atoms, or aryl with 6 to 10 carbon atoms, or denote a 5- to 7-member aromatic, optionally benzo-condensed, heterocyclic compound with up to 3 heteroatoms from the series S, N and/or O, which are optionally substituted up to 3 times in an identical manner or differently by trifluoromethyl, trifluoromethoxy, halogen, hydroxy, carboxyl, by straight-chain or branched alkyl, acyl, alkoxy, or alkoxycarbonyl with up to 6 carbon atoms each, or by phenyl, phenoxy, or thiophenyl, which can in turn be substituted by halogen, trifluoromethyl, or trifluoromethoxy, and/or the rings are substituted by a group of the formula —NR$_{VIII-11}$R$_{VIII-12}$, wherein R$_{VIII-11}$ and R$_{VIII-12}$ are identical or different and have the meaning given above for R$_{VIII-1}$ and R$_{VIII-2}$, X$_{VIII}$ denotes a straight or branched alkyl chain or alkenyl chain with 2 to 10 carbon atoms each, which are optionally substituted up to 2 times by hydroxy, R$_{VIII-9}$ denotes hydrogen, and R$_{VIII-10}$ denotes hydrogen, halogen, azido, trifluoromethyl, hydroxy, mercapto, trifluoromethoxy, straight-chain or branched alkoxy with up to 5 carbon atoms, or a radical of the formula —NR$_{VIII-13}$R$_{VIII-14}$, wherein R$_{VIII-13}$ and R$_{VIII-14}$ are identical or different and have the meaning given above for R$_{VIII-1}$ and R$_{VIII-2}$, or R$_{VIII-9}$ and R$_{VIII-10}$ form a carbonyl group together with the carbon atom.

Compounds of Formula V$_{III}$ are disclosed in WO 9804528, the complete disclosure of which is incorporated by reference.

Another class of CETP inhibitors that finds utility with the present invention consists of substituted 1,2,4-triazoles having the Formula IX

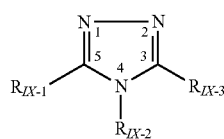

Formula IX or a pharmaceutically acceptable salt or tautomer thereof;

wherein R$_{IX-1}$ is selected from higher alkyl, higher alkenyl, higher alkynyl, aryl, aralkyl, aryloxyalkyl, alkoxyalkyl, alkylthioalkyl, arylthioalkyl, and cycloalkylalkyl;

wherein R$_{IX-2}$ is selected from aryl, heteroaryl, cycloalkyl, and cycloalkenyl, wherein R$_{IX-2}$ is optionally substituted at a substitutable position with one or more radicals independently selected from alkyl, haloalkyl, alkylthio, alkylsulfinyl, alkylsulfonyl, alkoxy, halo, aryloxy, aralkyloxy, aryl, aralkyl, aminosulfonyl, amino, monoalkylamino and dialkylamino; and wherein R$_{IX-3}$ is selected from hydrido, —SH and halo; provided R$_{IX-2}$ cannot be phenyl or 4-methylphenyl when R$_{IX-1}$ is higher alkyl and when R$_{IX-3}$ is —SH.

Compounds of Formula IX are disclosed in WO 9914204, the complete disclosure of which is incorporated by reference.

In a preferred embodiment, the CETP inhibitor is selected from the following compounds of Formula IX:

2,4-dihydro-4-(3-methoxyphenyl)-5-tridecyl-3H-1,2,4-triazole-3-thione;
2,4-dihydro-4-(2-fluorophenyl)-5-tridecyl-3H-1,2,4-triazole-3-thione;
2,4-dihydro-4-(2-methylphenyl)-5-tridecyl-3H-1,2,4-triazole-3-thione;
2,4-dihydro-4-(3-chlorophenyl)-5-tridecyl-3H-1,2,4-triazole-3-thione;
2,4-dihydro-4-(2-methoxyphenyl)-5-tridecyl-3H-1,2,4-triazole-3-thione;
2,4-dihydro-4-(3-methylphenyl)-5-tridecyl-3H-1,2,4-triazole-3-thione;
4-cyclohexyl-2,4-dihydro-5-tridecyl-3H-1,2,4-triazole-3-thione;
2,4-dihydro-4-(3-pyridyl)-5-tridecyl-3H-1,2,4-triazole-3-thione;
2,4-dihydro-4-(2-ethoxyphenyl)-5-tridecyl-3H-1,2,4-triazole-3-thione;
2,4-dihydro-4-(2,6-dimethylphenyl)-5-tridecyl-3H-1,2,4-triazole-3-thione;
2,4-dihydro-4-(4-phenoxyphenyl)-5-tridecyl-3H-1,2,4-triazole-3-thione;
4-(1,3-benzodioxol-5-yl)-2,4-dihydro-5-tridecyl-3H-1,2,4-triazole-3-thione;
4-(2-chlorophenyl)-2,4-dihydro-5-tridecyl-3H-1,2,4-triazole-3-thione;
2,4-dihydro-4-(4-methoxyphenyl)-5-tridecyl-3H-1,2,4-triazole-3-thione;
2,4-dihydro-5-tridecyl-4-(3-trifluoromethylphenyl)-3H-1,2,4-triazole-3-thione;
2,4-dihydro-q-tridecyl-4-(3-fluorophenyl)-3H-1,2,4-triazole-3-thione;
4-(3-chloro-4-methylphenyl)-2.4-dihydro-5-tridecyl-3H-1,2,4-triazole-3-thione;
2,4-dihydro-4-(2-methylthiophenyl)-5-tridecyl-3H-1,2,4-triazole-3-thione;
4-(4-benzyloxyphenyl)-2,4-dihydro-5-tridecyl-3H-1,2,4-triazole-3-thione;
2,4-dihydro-4-(2-naphthyl)-5-tridecyl-3H-1,2,4-triazole-3-thione;
2,4-dihydro-5-tridecyl-4-(4-trifluoromethylphenyl)-3H-1,2,4-triazole-3-thione;
2,4-dihydro-4-(1-naphthyl)-5-tridecyl-3H-1,2,4-triazole-3-thione;
2,4-dihydro-4-(3-methylthiophenyl)-5-tridecyl-3H-1,2,4-triazole-3-thione;
2,4-dihydro-4-(4-methylthiophenyl)-S-tridecyl-3H-1,2,4-triazole-3-thione;
2,4-dihydro-4-(3,4-dimethoxyphenyl)-5-tridecyl-3H-1,2,4-triazole-3-thione;
2,4-dihydro-4-(2,5-dimethoxyphenyl)-5-tridecyl-3H-1,2,4-triazole-3-thione;

2,4-dihydro-4-(2-methoxy-5-chlorophenyl)-5-tridecyl-3H-1,2,4-triazole-3-thione;

4-(4-aminosulfonylphenyl)-2,4-dihydro-5-tridecyl-3H-1,2,4-triazole-3-thione;

2,4-dihydro-5-dodecyl-4-(3-methoxyphenyl)-3H-1,2,4-triazole-3-thione;

2,4-dihydro-4-(3-methoxyphenyl)-5-tetradecyl-3H-1,2,4-triazole-3-thione;

2,4-dihydro-4-(3-methoxyphenyl)-5-undecyl-3H-1,2,4-triazole-3-thione; and 2,4-dihydro-(4-methoxyphenyl)-5-pentadecyl-3H-1,2,4-triazole-3-thione.

Another class of CETP inhibitors that finds utility with the present invention consists of hetero-tetrahydroquinolines having the Formula X

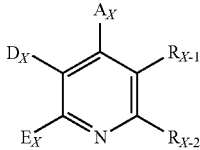

Formula X and pharmaceutically acceptable salts, enantiomers, or stereoisomers or N-oxides of said compounds;

in which $A_X$ represents cycloalkyl with 3 to 8 carbon atoms or a 5 to 7-membered, saturated, partially saturated or unsaturated, optionally benzo-condensed heterocyclic ring containing up to 3 heteroatoms from the series comprising S, N and/or O, that in case of a saturated heterocyclic ring is bonded to a nitrogen function, optionally bridged over it, and in which the aromatic systems mentioned above are optionally substituted up to 5-times in an identical or different substituents in the form of halogen, nitro, hydroxy, trifluoromethyl, trifluoromethoxy or by a straight-chain or branched alkyl, acyl, hydroxyalkyl or alkoxy each having up to 7 carbon atoms or by a group of the formula $-NR_{X-3}R_{X-4}$, in which $R_{X-3}$ and $R_{X-4}$ are identical or different and denote hydrogen, phenyl or straight-chain or branched alkyl having up to 6 carbon atoms, or $A_X$ represents a radical of the formula

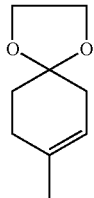

$D_X$ represents an aryl having 6 to 10 carbon atoms, that is optionally substituted by phenyl, nitro, halogen, trifluormethyl or trifluormethoxy, or it represents a radical of the formula

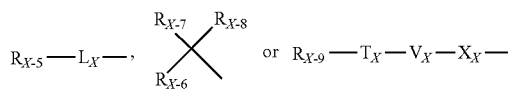

in which $R_{X-5}$, $R_{X-6}$ and $R_{X-9}$ independently of one another denote cycloalkyl having 3 to 6 carbon atoms, or an aryl having 6 to 10 carbon atoms or a 5- to 7-membered aromatic, optionally benzo-condensed saturated or unsaturated, mono-, bi-, or tricyclic heterocyclic ring from the series consisting of S, N and/or O, in which the rings are substituted, optionally, in case of the nitrogen containing aromatic rings via the N function, with up to 5 identical or different substituents in the form of halogen, trifluoromethyl, nitro, hydroxy, cyano, carbonyl, trifluoromethoxy, straight straight-chain or branched acyl, alkyl, alkylthio, alkylalkoxy, alkoxy, or alkoxycarbonyl each having up to 6 carbon atoms, by aryl or trifluoromethyl-substituted aryl each having 6 to 10 carbon atoms or by an, optionally benzo-condensed, aromatic 5- to 7-membered heterocyclic ring having up to 3 heteroatoms from the series consisting of S, N, and/or O, and/or substituted by a group of the formula $-OR_{X-10}$, $-SR_{X-11}$, $SO_2R_{X-12}$ or $-NR_{X-13}R_{X-14}$, in which $R_{X-10}$, $R_{X-11}$ and $R_{X-12}$ independently from each other denote aryl having 6 to 10 carbon atoms, which is in turn substituted with up to 2 identical or different substituents in the form of phenyl, halogen or a straight-chain or branched alkyl having up to 6 carbon atoms, $R_{X-13}$ and $R_{X-14}$ are identical or different and have the meaning of $R_{X-3}$ and $R_{X-4}$ indicated above, or $R_{X-5}$ and/or $R_{X-6}$ denote a radical of the formula

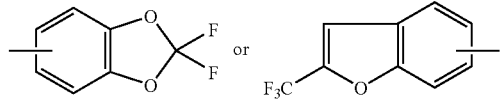

$R_{X-7}$ denotes hydrogen or halogen, and $R_{X-8}$ denotes hydrogen, halogen, azido, trifluoromethyl, hydroxy, trifluoromethoxy, straight-chain or branched alkoxy or alkyl having up to 6 carbon atoms or a radical of the formula $-NR_{X-15}R_{X-16}$, in which $R_{X-15}$ and $R_{X-16}$ are identical or different and have the meaning of $R_{X-3}$ and $R_{X-4}$ indicated above, or $R_{X-7}$ and $R_{X-8}$ together form a radical of the formula $=O$ or $=NR_{X-17}$, in which $R_{X-17}$ denotes hydrogen or straight chain or branched alkyl, alkoxy or acyl having up to 6 carbon atoms, $L_X$ denotes a straight chain or branched alkylene or alkenylene chain having up to 8 carbon atoms, that are optionally substituted with up to 2 hydroxy groups, $T_X$ and $X_X$ are identical or different and denote a straight chain or branched alkylene chain with up to 8 carbon atoms or $T_X$ or $X_X$ denotes a bond, $V_X$ represents an oxygen or sulfur atom or an $-NR_{X-18}-$ group, in which $R_{X-18}$ denotes hydrogen or straight chain or branched alkyl with up to 6 carbon atoms or phenyl, $E_X$ represents cycloalkyl with 3 to 8 carbon atoms, or straight chain or branched alkyl with up to 8 carbon atoms, that is optionally substituted by cycloalkyl with 3 to 8 carbon atoms or hydroxy, or represents a phenyl, that is optionally substituted by halogen or trifluoromethyl, $R_{X-1}$ and $R_{X-2}$ together form a straight-chain or branched alkylene chain with up to 7 carbon atoms, that must be substituted by carbonyl group and/or by a radical with the formula

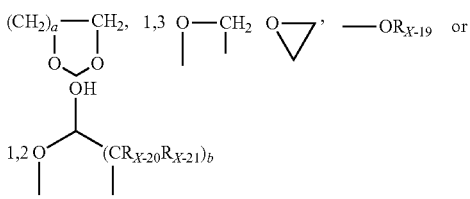

in which a and b are identical or different and denote a number equaling 1, 2, or 3, $R_{X-19}$ denotes hydrogen, cycloalkyl with 3 up to 7 carbon atoms, straight chain or branched silylalkyl with up to 8 carbon atoms or straight chain or branched alkyl with up to 8 carbon atoms, that are optionally substituted by hydroxyl, straight chain or branched alkoxy with up to 6 carbon atoms or by phenyl, which in turn might be substituted by halogen, nitro, trifluormethyl, trifluoromethoxy or by phenyl or by tetrazole-substituted phenyl, and alkyl, optionally be substituted by a group with the formula $-OR_{X-22}$, in which $R_{X-22}$ denotes a straight chain or branched acyl with up to 4 carbon atoms or benzyl, or $R_{X-19}$ denotes straight chain or branched acyl with up to 20 carbon atoms or benzoyl, that is optionally substituted by halogen, trifluoromethyl, nitro or trifluoromethoxy, or it denotes straight chain or branched fluoroacyl with up to 8 carbon atoms and 9 fluorine atoms, $R_{X-20}$ and $R_{X-21}$ are identical or different and denote hydrogen, phenyl or straight chain or branched alkyl with up to 6 carbon atoms, or $R_{X-20}$ and $R_{X-21}$ together form a 3- to 6-membered carbocyclic ring, and the carbocyclic rings formed are optionally substituted, optionally also geminally, with up to six identical or different substituents in the form of triflouromethyl, hydroxy, nitrile, halogen, carboxyl, nitro, azido, cyano, cycloalkyl or cycloalkyloxy with 3 to 7 carbon atoms each, by straight chain or branched alkoxycarbonyl, alkoxy or alkylthio with up to 6 carbon atoms each or by straight chain or branched alkyl with up to 6 carbon atoms, which in turn is substituted with up to 2 identically or differently by hydroxyl, benzyloxy, trifluoromethyl, benzoyl, straight chain or branched alkoxy, oxyacyl or carbonyl with up to 4 carbon atoms each and/or phenyl, which may in turn be substituted with a halogen, trifuoromethyl or trifluoromethoxy, and/or the formed carbocyclic rings are optionally substituted, also geminally, with up to 5 identical or different substituents in the form of phenyl, benzoyl, thiophenyl or sulfonylbenzyl, which in turn are optionally substituted by halogen, trifluoromethyl, trifluoromethoxy or nitro, and/or optionally are substituted by a radical with the formula

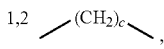

$-SO_2-C_6H_5, -(CO)_d NR_{X-23}R_{X-24}$ or $=O$, in which
c denotes a number equaling 1, 2, 3, or 4,
d denotes a number equaling 0 or 1,
$R_{X-23}$ and $R_{X-24}$ are identical or different and denote hydrogen, cycloalkyl with 3 to 6 carbon atoms, straight chain or branched alkyl with up to 6 carbon atoms, benzyl or phenyl, that is optionally substituted with up to 2 identically or differently by halogen, trifluoromethyl, cyano, phenyl or nitro, and/or the formed carbocyclic rings are substituted optionally by a spiro-linked radical with the formula

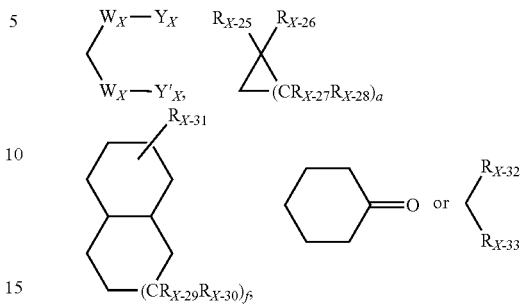

in which
$W_X$ denotes either an oxygen or a sulfur atom
$Y_X$ and $Y'_X$ together form a 2 to 6 membered straight chain or branched alkylene chain,
e denotes a number equaling 1, 2, 3, 4, 5, 6, or 7,
f denotes a number equaling 1 or 2,
$R_{X-25}, R_{X-26}, R_{X-27}, R_{X-28}, R_{X-29}, R_{X-30}$ and $R_{X-31}$ are identical or different and denote hydrogen, trifluoromethyl, phenyl, halogen or straight chain or branched alkyl or alkoxy with up to 6 carbon atoms each, or $R_{X-25}$ and $R_{X-26}$ or $R_{X-27}$ and $R_{X-28}$ respectively form together a straight chain or branched alkyl chain with up to 6 carbon atoms, or $R_{X-25}$ and $R_{X-26}$ or $R_{X-27}$ and $R_{X-28}$ each together form a radical with the formula

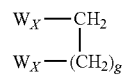

in which
$W_X$ has the meaning given above,
g denotes a number equaling 1, 2, 3, 4, 5, 6, or 7,
$R_{X-32}$ and $R_{X-33}$ form together a 3- to 7-membered heterocycle, which contains an oxygen or sulfur atom or a group with the formula SO, $SO_2$ or $-NR_{X-34}$,
in which
$R_{X-34}$ denotes hydrogen, phenyl, benzyl or straight or branched alkyl with up to 4 carbon atoms.

Compounds of Formula X are disclosed in WO 9914215, the complete disclosure of which is incorporated by reference.

In a preferred embodiment, the CETP inhibitor is selected from the following compounds of Formula X:
2-cyclopentyl-5-hydroxy-7,7-dimethyl-4-(3-thienyl)-3-(4-trifluoromethylbenxoyl)-5,6,7,8-tetrahydroquinoline;
2-cyclopentyl-3-[fluoro-(4-trifluoromethylphenyl)methyl]-5-hydroxy-7,7-dimethyl-4-(3-thienyl)-5,6,7,8-tetrahydroquinoline; and
2-cyclopentyl-5-hydroxy-7,7-dimethyl-4-(3-thienyl)-3-(trifluoromethylbenxyl)-5,6,7,8-tetrahydroquinoline.

Another class of CETP inhibitors that finds utility with the present invention consists of substituted tetrahydro naphthalines and analogous compounds having the Formula XI

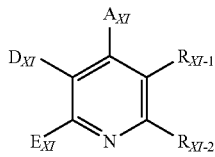

Formula XI and stereoisomers, stereoisomer mixtures, and salts thereof, in which $A_{XI}$ stands for cycloalkyl with 3 to 8 carbon atoms, or stands for aryl with 6 to 10 carbon atoms, or stands for a 5- to 7-membered, saturated, partially unsaturated or unsaturated, possibly benzocondensated, heterocycle with up to 4 heteroatoms from the series S, N and/or O, where aryl and the heterocyclic ring systems mentioned above are substituted up to 5-fold, identical or different, by cyano, halogen, nitro, carboxyl, hydroxy, trifluoromethyl, trifluoro-methoxy, or by straight-chain or branched alkyl, acyl, hydroxyalkyl, alkylthio, alkoxycarbonyl, oxyalkoxycarbonyl or alkoxy each with up to 7 carbon atoms, or by a group of the formula

—$NR_{XI-3}R_{XI-4}$, in which $R_{XI-3}$ and $R_{XI-4}$ are identical or different and denote hydrogen, phenyl, or straight-chain or branched alkyl with up to 6 carbon atoms $D_{XI}$ stands for a radical of the formula

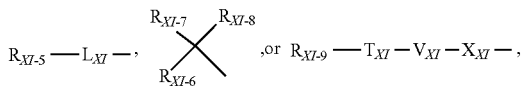

in which $R_{XI-5}$, $R_{XI-6}$ and $R_{XI-9}$, independent of each other, denote cycloalkyl with 3 to 6 carbon atoms, or denote aryl with 6 to 10 carbon atoms, or denote a 5- to 7-membered, possibly benzocondensated, saturated or unsaturated, mono-, bi- or tricyclic heterocycle with up to 4 heteroatoms of the series S, N and/or O, where the cycles are possibly substituted-in the case of the nitrogen-containing rings also via the N-function-up to 5-fold, identical or different, by halogen, trifluoromethyl. nitro, hydroxy, cyano, carboxyl, trifluoromethoxy, straight-chain or branched acyl, alkyl, alkylthio, alkylalkoxy, alkoxy or alkoxycarbonyl with up to 6 carbon atoms each. by aryl or trifluoromethyl substituted aryl with 6 to 10 carbon atoms each, or by a possibly benzocondensated aromatic 5- to 7-membered heterocycle with up to 3 heteroatoms of the series S, N and/or O, and/or are substituted by a group of the formula —$OR_{XI-10}$, —$SR_{XI-11}$, —$SO_2R_{XI-12}$ or —$NR_{XI-13}R_{XI-14}$, in which $R_{XI-10}$, $R_{XI-11}$ and $R_{XI-12}$, independent of each other, denote aryl with 6 to 10 carbon atoms, which itself is substituted up to 2-fold, identical or different, by phenyl, halogen. or by straight-chain or branched alkyl with up to 6 carbon atoms, $R_{XI-13}$ and $R_{XI-14}$ are identical or different and have the meaning given above for $R_{XI-3}$ and $R_{XI-4}$, or $R_{XI-5}$ and/or $R_{XI-6}$ denote a radical of the formula

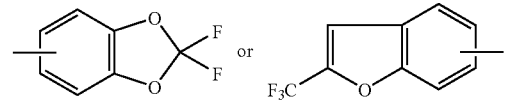

$R_{XI-7}$ denotes hydrogen, halogen or methyl, and $R_{XI-8}$ denotes hydrogen, halogen, azido, trifluoromethyl, hydroxy, trifluoromethoxy, straight-chain or branched alkoxy or alkyl with up to 6 carbon atoms each, or a radical of the formula —$NR_{XI-15}R_{XI-16}$, in which $R_{XI-15}$ and $R_{XI-16}$ are identical or different and have the meaning given above for $R_{XI-3}$ and $R_{XI-4}$, or $R_{XI-7}$ and $R_{XI-8}$ together form a radical of the formula =O or =$NR_{XI-17}$, in which $R_{XI-17}$ denotes hydrogen or straight-chain or branched alkyl, alkoxy or acyl with up to 6 carbon atoms each, $L_{XI}$ denotes a straight-chain or branched alkylene or alkenylene chain with up to 8 carbon atoms each, which is possibly substituted up to 2-fold by hydroxy, $T_{XI}$ and $X_{XI}$ are identical or different and denote a straight-chain or branched alkylene chain with up to 8 carbon atoms, or $T_{XI}$ and $X_{XI}$ denotes a bond, $V_{XI}$ stands for an oxygen- or sulfur atom or for an —$NR_{XI-18}$ group, in which $R_{XI-18}$ denotes hydrogen or straight-chain or branched alkyl with up to 6 carbon atoms, or phenyl, $E_{XI}$ stands for cycloalkyl with 3 to 8 carbon atoms, or stands for straight-chain or branched alkyl with up to 8 carbon atoms, which is possibly substituted by cycloalkyl with 3 to 8 carbon atoms or hydroxy, or stands for phenyl, which is possibly substituted by halogen or trifluoromethyl, $R_{XI-1}$ and $R_{XI-2}$ together form a straight-chain or branched alkylene chain with up to 7 carbon atoms, which must be substituted by a carbonyl group and/or by a radical of the formula

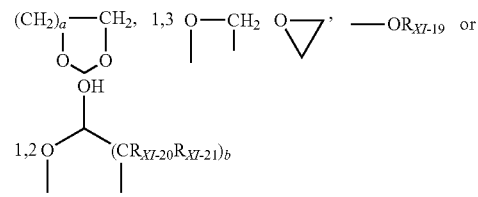

in which a and b are identical or different and denote a number 1, 2 or 3

$R_{XI-19}$ denotes hydrogen, cycloalkyl with 3 to 7 carbon atoms, straight-chain or branched silylalkyl with up to 8 carbon atoms, or straight-chain or branched alkyl with up to 8 carbon atoms, which is possibly substituted by hydroxy, straight-chain or branched alkoxy with up to 6 carbon atoms, or by phenyl, which itself can be substituted by halogen, nitro, trifluoromethyl, trifluoromethoxy or by phenyl substituted by phenyl or tetrazol, and alkyl is possibly substituted by a group of the formula —$OR_{XI-22}$, in which $R_{XI-22}$ denotes straight-chain or branched acyl with up to 4 carbon atoms, or benzyl, or $R_{XI-19}$ denotes straight-chain or branched acyl with up to 20 carbon atoms or benzoyl, which is possibly substituted by halogen, trifluoromethyl, nitro or trifluoromethoxy, or denotes straight-chain or branched fluoroacyl with up to 8 carbon atoms and 9 fluorine atoms, $R_{XI-20}$ and $R_{XI-21}$ are identical or different, denoting hydrogen, phenyl or straight-chain or branched alkyl with up to 6 carbon atoms, or $R_{XI-20}$ and $R_{XI-21}$ together form a 3- to 6-membered carbocycle, and, possibly also geminally, the alkylene chain formed by $R_{XI-1}$ and $R_{XI-2}$, is possibly substituted up to 6-fold, identical or different, by trifluoromethyl, hydroxy, nitrile, halogen, carboxyl, nitro, azido, cyano, cycloalkyl or cycloalkyloxy with 3 to 7 carbon atoms each, by straight-chain or branched alkoxycarbonyl, alkoxy or alkoxythio with up to 6 carbon atoms each, or by straight-chain or branched alkyl with up to 6 carbon atoms, which itself is substituted up to 2-fold, identical or different. by hydroxyl, benzyloxy, trifluoromethyl, benzoyl, straight-chain or branched alkoxy, oxyacyl or carboxyl with up to 4 carbon atoms each, and/or phenyl—which itself can be substituted by halogen, trifluoromethyl or trifluoromethoxy, and/or the alkylene chain formed by $R_{XI-1}$ and $R_{XI-2}$ is substituted, also geminally, possibly up to 5-fold, identical or different, by phenyl, benzoyl, thiophenyl or sulfobenzyl—which themselves are possibly substituted by halogen, trifluoromethyl, trifluoromethoxy or nitro, and/or the alkylene chain formed by $R_{XI-1}$ and $R_{XI-2}$ is possibly substituted by a radical of the formula

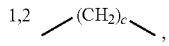

$-SO_2-C_6H_5, -(CO)_d NR_{XI-23}R_{XI-24}$ or $=O$, in which c denotes a number 1, 2, 3 or 4, d denotes a number 0 or 1, $R_{XI-23}$ and $R_{XI-24}$ are identical or different and denote hydrogen, cycloalkyl with 3 to 6 carbon atoms, straight-chain or branched alkyl with up to 6 carbon atoms, benzyl or phenyl, which is possibly substituted up to 2-fold. identical or different, by halogen, trifluoromethyl, cyano, phenyl or nitro, and/or the alkylene chain formed by $R_{XI-1}$ and $R_{XI-2}$ is possibly substituted by a spiro-jointed radical of the formula

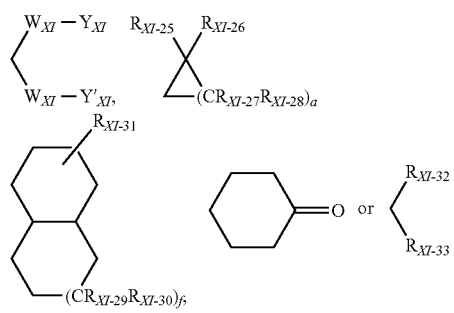

in which $W_{XI}$ denotes either an oxygen or a sulfur atom, $Y_{XI}$ and $Y'_{XI}$ together form a 2- to 6-membered straight-chain or branched alkylene chain, e is a number 1, 2, 3, 4, 5, 6 or 7, f denotes a number 1 or 2, $R'_{XI-25}, R_{XI-26}, R_{XI-27}, R_{XI-28}, R_{XI-29}, R_{XI-30}$, and $R_{XI-31}$ are identical or different and denote hydrogen, trifluoromethyl, phenyl, halogen, or straight-chain or branched alkyl or alkoxy with up to 6 carbon atoms each, or $R_{XI-25}$ and $R_{XI-26}$ or $R_{XI-27}$ and $R_{XI-28}$ together form a straight-chain or branched alkyl chain with up to 6 carbon atoms, or $R_{XI-25}$ and $R_{XI-26}$ or $R_{XI-27}$ and $R_{XI-28}$ together form a radical of the formula

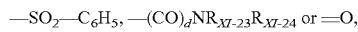

in which $W_{XI}$ has the meaning given above, g is a number 1, 2, 3, 4, 5, 6 or 7, $R_{XI-32}$ and $R_{XI-33}$ together form a 3- to 7-membered heterocycle that contains an oxygen- or sulfur atom or a group of the formula SO, $SO_2$ or $-NR_{XI-34}$, in which $R_{XI-34}$ denotes hydrogen, phenyl, benzyl, or straight-chain or branched alkyl with up to 4 carbon atoms.

Compounds of Formula XI are disclosed in WO 9914174, the complete disclosure of which is incorporated by reference.

Another class of CETP inhibitors that finds utility with the present invention consists of 2-aryl-substituted pyridines having the Formula (XII)

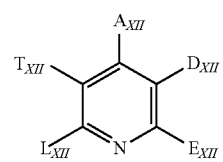

Formula XII or pharmaceutically acceptable salts, enantiomers, or stereoisomers of said compounds, in which $A_{XII}$ and $E_{XII}$ are identical or different and stand for aryl with 6 to 10 carbon atoms which is possibly substituted, up to 5-fold identical or different, by halogen, hydroxy, trifluoromethyl, trifluoromethoxy, nitro or by straight-chain or branched alkyl, acyl, hydroxy alkyl or alkoxy with up to 7 carbon atoms each, or by a group of the formula $-NR_{XII-1}R_{XII-2}$, where $R_{XII-1}$ and $R_{XII-2}$ are identical or different and are meant to be hydrogen, phenyl or straight-chain or branched alkyl with up to 6 carbon atoms, $D_{XII}$ stands for straight-chain or branched alkyl with up to 8 carbon atoms, which is substituted by hydroxy, $L_{XII}$ stands for cycloalkyl with 3 to 8 carbon atoms or for straight-chain or branched alkyl with up to 8 carbon atoms, which is possibly substituted by cycloalkyl with 3 to 8 carbon atoms, or by hydroxy, $T_{XII}$ stands for a radical of the formula $R_{XII-3}$—$X_{XII}$— or

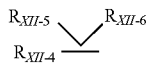

where $R_{XII-3}$ and $R_{XII-4}$ are identical or different and are meant to be cycloalkyl with 3 to 8 carbon atoms, or aryl with 6 to 10 carbon atoms, or a 5- to 7-membered aromatic, possibly benzocondensated heterocycle with up to 3 heteroatoms from the series S, N and/or O, which are possibly substituted. up to 3-fold identical or different, by trifluoromethyl, trifluoromethoxy, halogen, hydroxy, carboxyl, nitro, by straight-chain or branched alkyl, acyl, alkoxy or alkoxycarbonyl with up to 6 carbon atoms each. or by phenyl, phenoxy or phenylthic which in turn can be substituted by halogen. trifluoromethyl or trifluoromethoxy, and/or where the cycles are possibly substituted by a group of the formula —$NR_{XII-7}R_{XII-8}$, where $R_{XII-7}$ and $R_{XII-8}$ are identical or different and have the meaning of $R_{XII-1}$ and $R_{XII-2}$ given above, $X_{XII}$ is a straight-chain or branched alkyl or alkenyl with 2 to 10 carbon atoms each, possibly substituted up to 2-fold by hydroxy or halogen, $R_{XII-5}$ stands for hydrogen, and $R_{XII-6}$ means to be hydrogen, halogen, mercapto, azido, trifluoromethyl, hydroxy, trifluoromethoxy, straight-chain or branched alkoxy with up to 5 carbon atoms, or a radical of the formula —$NR_{II-9}R_{XII-10}$, where $R_{XII-9}$ and $R_{XII-10}$ are identical or different and have the meaning of $R_{XII-1}$ and $R_{XII-2}$ given above, or $R_{XII-5}$ and $R_{XII-6}$, together with the carbon atom, form a carbonyl group.

Compounds of Formula XII are disclosed in EP 796846-A1, the complete disclosure of which is incorporated by reference.

In a preferred embodiment, the CETP inhibitor is selected from the following compounds of Formula XII:
4,6-bis-(p-fluorophenyl)-2-isopropyl-3-[(p-trifluoromethylphenyl)-(fluoro)-methyl]-5-(1-hydroxyethyl)pyridine;
2,4-bis-(4-fluorophenyl)-6-isopropyl-5-[4-(trifluoromethylphenyl)-fluoromethyl]3-hydroxymethyl)pyridine; and
2,4-bis-(4-fluorophenyl)-6-isopropyl-5-[2-(3-trifluoromethylphenyl)vinyl]-3-hydroxymethyl)pyridine.

Another class of CETP inhibitors that finds utility with the present invention consists of compounds having the Formula (XIII)

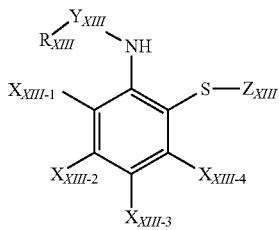

Formula XIII or pharmaceutically acceptable salts, enantiomers, stereoisomers, hydrates, or solvates of said compounds, in which $R_{XIII}$ is a straight chain or branched $C_{1-10}$ alkyl; straight chain or branched $C_{2-10}$ alkenyl; halogenated $C_{1-4}$ lower alkyl; $C_{3-10}$ cycloalkyl that may be substituted; $C_{5-8}$ cycloalkenyl that may be substituted; $C_{3-10}$ cycloalkyl $C_{1-10}$ alkyl that may be substituted; aryl that may be substituted; aralkyl that may be substituted; or a 5- or 6-membered heterocyclic group having 1 to 3 nitrogen atoms, oxygen atoms or sulfur atoms that may be substituted, $X_{XIII-1}$, $X_{XIII-2}$, $X_{XIII-3}$, $X_{XIII-4}$ may be the same or different and are a hydrogen atom; halogen atom; $C_{1-4}$ lower alkyl; halogenated $C_{1-4}$ lower alkyl; $C_{1-4}$ lower alkoxy; cyano group; nitro group; acyl; or aryl, respectively;

$Y_{XIII}$ is —CO—; or —$SO_2$—; and $Z_{XIII}$ is a hydrogen atom; or mercapto protective group.

Compounds of Formula XIII are disclosed in WO 98/35937, the complete disclosure of which is incorporated by reference.

In a preferred embodiment, the CETP inhibitor is selected from the following compounds of Formula XIII:
N,N'-(dithiodi-2,1-phenylene)bis[2,2-dimethyl-propanamide];
N,N'-(dithiodi-2,1-phenylene)bis[1-methyl-cyclohexanecarboxamide];
N,N'-(dithiodi-2,1-phenylene)bis[1-(3-methylbutyl)-cyclopentanecarboxamide];
N,N'-(dithiodi-2,1-phenylene)bis[1-(3-methylbutyl)-cyclohexanecarboxamide];
N,N'-(dithiodi-2,1-phenylene)bis[1-(2-ethylbutyl)-cyclohexanecarboxamide];
N,N'-(dithiodi-2,1-phenylene)bis-tricyclo[3.3.1.1$^{3,7}$]decane-1-carboxamide;
propanethioic acid, 2-methyl-,S-[2-[[[1-(2-ethylbutyl)cyclohexyl]carbonyl]amino]phenyl]ester;
propanethioic acid, 2,2-dimethyl-,S-[2-[[[1-(2-ethylbutyl)cyclohexyl]carbonyl]amino]phenyl]ester; and
ethanethioic acid, S-[2-[[[1-(2-ethylbutyl)cyclohexyl]carbonyl]amino]phenyl]ester.

Concentration-Enhancing Polymers

Concentration-enhancing polymers suitable for use in the compositions of the present invention should be inert, in the sense that they do not chemically react with the CETP inhibitor in an adverse manner, are pharmaceutically acceptable, and have at least some solubility in aqueous solution at physiologically relevant pHs (e.g. 1-8). The polymer can be neutral or ionizable, and should have an aqueous-solubility of at least 0.1 mg/mL over at least a portion of the pH range of 1-8.

The polymer is a "concentration-enhancing polymer," meaning that it meets at least one, and more preferably both, of the following conditions. The first condition is that the concentration enhancing polymer increases the MDC of the CETP inhibitor in the environment of use relative to a control composition consisting of an equivalent amount of the CETP inhibitor but no polymer. That is, once the composition is introduced into an environment of use, the polymer increases the aqueous concentration of CETP inhibitor relative to the control composition. Preferably, the polymer increases the MDC of the CETP inhibitor in aqueous solution by at least 10-fold relative to a control composition, preferably by at least 50-fold, and more preferably by at least 200-fold. Even more preferably, the polymer increases the MDC of the CETP inhibitor in aqueous solution by at least 500-fold, and most preferably by at least 1000-fold. Such large enhancements may be necessary in order for some extremely water insoluble CETP inhibitors to achieve effective blood levels through oral dosing. The second condition is that the concentration-enhancing polymer increases the AUC of the CETP inhibitor in the environment of use relative to a control composition consisting of CETP inhibitor but no polymer as described above. That is, in the environment of use, the composition comprising the CETP inhibitor and the concentration-enhancing polymer provides an area under the concentration versus time curve (AUC) for any period of 90 minutes between the time of introduction into the use environment and about 270 minutes following introduction to the use environment that is at least 5-fold that of a control composition comprising an equivalent quantity of CETP inhibitor but no polymer. Preferably, the AUC provided by the composition is at least 25-fold, more preferably at least 100-fold, and even more preferably at least 250-fold that of the control composition.

Concentration-enhancing polymers suitable for use with the present invention may be cellulosic or non-cellulosic. The polymers may be neutral or ionizable in aqueous solution. Of these, ionizable and cellulosic polymers are preferred, with ionizable cellulosic polymers being more preferred.

A preferred class of polymers comprises polymers that are "amphiphilic" in nature, meaning that the polymer has hydrophobic and hydrophilic portions. The hydrophobic portion may comprise groups such as aliphatic or aromatic hydrocarbon groups. The hydrophilic portion may comprise either ionizable or non-ionizable groups that are capable of hydrogen bonding such as hydroxyls, carboxylic acids, esters, amines or amides.

Amphiphilic and/or ionizable polymers are preferred because it is believed that such polymers may tend to have relatively strong interactions with the CETP inhibitor and may promote the formation of the various types of polymer/drug assemblies in the use environment as described previously. In addition, the repulsion of the like charges of the ionized groups of such polymers may serve to limit the size of the polymer/drug assemblies to the nanometer or submicron scale. For example, while not wishing to be bound by a particular theory, such polymer/drug assemblies may comprise hydrophobic CETP inhibitor clusters surrounded by the polymer with the polymer's hydrophobic regions turned inward towards the CETP inhibitor and the hydrophilic regions of the polymer turned outward toward the aqueous environment. Alternatively, depending on the specific chemical nature of the CETP inhibitor, the ionized functional groups of the polymer may associate, for example, via ion pairing or hydrogen bonds, with ionic or polar groups of the CETP inhibitor. In the case of ionizable polymers, the hydrophilic regions of the polymer would include the ionized functional groups. Such polymer/drug assemblies in solution may well resemble charged polymeric micellar-like structures. In any case, regardless of the mechanism of action, the inventors have observed that such amphiphilic polymers, particularly ionizable cellulosic polymers, have been shown to improve the MDC and/or AUC of CETP inhibitor in aqueous solution relative to control compositions free from such polymers.

Surprisingly, such amphiphilic polymers can greatly enhance the maximum concentration of CETP inhibitor obtained when CETP inhibitor is dosed to a use environment. In addition, such amphiphilic polymers interact with the CETP inhibitor to prevent the precipitation or crystallization of the CETP inhibitor from solution despite its concentration being substantially above its equilibrium concentration. In particular, when the preferred compositions are solid amorphous dispersions of the CETP inhibitor and the concentration-enhancing polymer, the compositions provide a greatly enhanced drug concentration, particularly when the dispersions are substantially homogeneous. The maximum drug concentration may be 10-fold and often more than 50-fold the equilibrium concentration of the crystalline CETP inhibitor. Indeed, for some extremely water insoluble CETP inhibitors, the maximum drug concentration may be 200-fold to 500-fold and often more than 1000-fold the equilibrium concentration of the crystalline CETP inhibitor. Such enhanced CETP inhibitor concentrations in turn lead to substantially enhanced relative bioavailability for the CETP inhibitor.

One class of polymers suitable for use with the present invention comprises neutral non-cellulosic polymers. Exemplary polymers include: vinyl polymers and copolymers having substituents of hydroxyl, alkylacyloxy, and cyclicamido polyvinyl alcohols that have at least a portion of their repeat units in the unhydrolyzed (vinyl acetate) form; polyvinyl alcohol polyvinyl acetate copolymers; polyvinyl pyrrolidone; and polyethylene polyvinyl alcohol copolymers Another class of polymers suitable for use with the present invention comprises ionizable non-cellulosic polymers. Exemplary polymers include: carboxylic acid-functionalized vinyl polymers, such as the carboxylic acid functionalized polymethacrylates and carboxylic acid functionalized polyacrylates such as the EUDRAGITS® manufactured by Rohm Tech Inc., of Malden, Mass.; amine-functionalized polyacrylates and polymethacrylates; proteins; and carboxylic acid functionalized starches such as starch glycolate.

Non-cellulosic polymers that are amphiphilic are copolymers of a relatively hydrophilic and a relatively hydrophobic monomer. Examples include acrylate and methacrylate copolymers. Exemplary commercial grades of such copolymers include the BUDRAGITS, which are copolymers of methacrylates and acrylates.

A preferred class of polymers comprises ionizable and neutral cellulosic polymers with at least one ester- and/or ether-linked substituent in which the polymer has a degree of substitution of at least 0.1 for each substituent. It should be noted that in the polymer nomenclature used herein, ether-linked substituents are recited prior to "cellulose" as the moiety attached to the ether group; for example, "ethylbenzoic acid cellulose" has ethoxybenzoic acid substituents. Analogously, ester-linked substituents are recited after "cellulose" as the carboxylate; for example, "cellulose phthalate" has one carboxylic acid of each phthalate moiety ester-linked to the polymer and the other carboxylic acid unreacted.

It should also be noted that a polymer name such as "cellulose acetate phthalate" (CAP) refers to any of the family of cellulosic polymers that have acetate and phthalate groups attached via ester linkages to a significant fraction of the cellulosic polymer's hydroxyl groups. Generally, the degree of substitution of each substituent group can range from 0.1 to 2.9 as long as the other criteria of the polymer are met. "Degree of substitution" refers to the average number of the three hydroxyls per saccharide repeat unit on the cellulose chain that have been substituted. For example, if all of the hydroxyls on the cellulose chain have been phthalate substituted, the phthalate degree of substitution is 3. Also included within each polymer family type are cellulosic polymers that have additional substituents added in relatively small amounts that do not substantially alter the performance of the polymer.

Amphiphilic cellulosics may be prepared by substituting the cellulose at any or all of the 3 hydroxyl substituents present on each saccharide repeat unit with at least one relatively hydrophobic substituent. Hydrophobic substituents may be essentially any substituent that, if substituted to a high enough level or degree of substitution, can render the cellulosic polymer essentially aqueous insoluble. Hydrophilic regions of the polymer can be either those portions that are relatively unsubstituted, since the unsubstituted hydroxyls are themselves relatively hydrophilic, or those regions that are substituted with hydrophilic substituents. Examples of hydrophobic substitutents include ether-linked alkyl groups such as methyl, ethyl, propyl, butyl, etc.; or ester-linked alkyl groups such as acetate, propionate, butyrate, etc.; and ether- and/or ester-linked aryl groups such as phenyl, benzoate, or phenylate. Hydrophilic groups include ether- or ester-linked nonionizable groups such as the hydroxy alkyl substituents hydroxyethyl, hydroxypropyl, and the alkyl ether groups such as ethoxyethoxy or methoxyethoxy. Particularly preferred hydrophilic substituents are those that are ether- or ester-linked ionizable groups such as carboxylic acids, thiocarboxylic acids, substituted phenoxy groups, amines, phosphates or sulfonates.

One class of cellulosic polymers comprises neutral polymers, meaning that the polymers are substantially non-ionizable in aqueous solution. Such polymers contain non-ionizable substituents, which may be either ether-linked or ester-linked. Exemplary ether-linked non-ionizable substituents include: alkyl groups, such as methyl, ethyl, propyl, butyl, etc.; hydroxy alkyl groups such as hydroxymethyl, hydroxyethyl, hydroxypropyl, etc.; and aryl groups such as phenyl. Exemplary ester-linked non-ionizable groups include: alkyl groups, such as acetate, propionate, butyrate, etc.; and aryl groups such as phenylate. However, when aryl groups are included, the polymer may need to include a sufficient amount of a hydrophilic substituent so that the polymer has at least some water solubility at any physiologically relevant pH of from 1 to 8.

Exemplary non-ionizable polymers that may be used as the polymer include: hydroxypropyl methyl cellulose acetate, hydroxypropyl methyl cellulose, hydroxypropyl cellulose, methyl cellulose, hydroxyethyl methyl cellulose, hydroxyethyl cellulose acetate, and hydroxyethyl ethyl cellulose.

A preferred set of neutral cellulosic polymers are those that are amphiphilic. Exemplary polymers include hydroxypropyl methyl cellulose and hydroxypropyl cellulose acetate, where cellulosic repeat units that have relatively high numbers of methyl or acetate substituents relative to the unsubstituted hydroxyl or hydroxypropyl substituents constitute hydrophobic regions relative to other repeat units on the polymer.

A preferred class of cellulosic polymers comprises polymers that are at least partially ionizable at physiologically relevant pH and include at least one ionizable substituent, which may be either ether-linked or ester-linked. Exemplary ether-linked ionizable substituents include: carboxylic acids, such as acetic acid, propionic acid, benzoic acid, salicylic acid, alkoxybenzoic acids such as ethoxybenzoic acid or propoxybenzoic acid, the various isomers of alkoxyphthalic acid such as ethoxyphthalic acid and ethoxyisophthalic acid, the various isomers of alkoxynicotinic acid such as ethoxynicotinic acid, and the various isomers of picolinic acid such as ethoxypicolinic acid, etc.; thiocarboxylic acids, such as thioacetic acid; substituted phenoxy groups, such as hydroxyphenoxy, etc.; amines, such as aminoethoxy, diethylaminoethoxy, trimethylaminoethoxy, etc.; phosphates, such as phosphate ethoxy; and sulfonates, such as sulphonate ethoxy. Exemplary ester linked ionizable substituents include: carboxylic acids, such as succinate, citrate, phthalate, terephthalate, isophthalate, trimellitate, and the various isomers of pyridinedicarboxylic acid, etc.; thiocarboxylic acids, such as thiosuccinate; substituted phenoxy groups, such as amino salicylic acid; amines, such as natural or synthetic amino acids, such as alanine or phenylalanine; phosphates, such as acetyl phosphate; and sulfonates, such as acetyl sulfonate.

For aromatic-substituted polymers to also have the requisite aqueous solubility, it is also desirable that sufficient hydrophilic groups such as hydroxypropyl or carboxylic acid functional groups be attached to the polymer to render the polymer aqueous soluble at least at pH values where any ionizable groups are ionized. In some cases, the aromatic group may itself be ionizable, such as phthalate or trimellitate substituents.

Exemplary cellulosic polymers that are at least partially ionized at physiologically relevant pHs include: hydroxypropyl methyl cellulose acetate succinate, hydroxypropyl methyl cellulose succinate, hydroxypropyl cellulose acetate succinate, hydroxyethyl methyl cellulose succinate, hydroxyethyl cellulose acetate succinate, hydroxypropyl methyl cellulose phthalate, hydroxyethyl methyl cellulose acetate succinate, hydroxyethyl methyl cellulose acetate phthalate, carboxyethyl cellulose, carboxymethyl cellulose, cellulose acetate phthalate, methyl cellulose acetate phthalate, ethyl cellulose acetate phthalate, hydroxypropyl cellulose acetate phthalate, hydroxypropyl methyl cellulose acetate phthalate, hydroxypropyl cellulose acetate phthalate succinate, hydroxypropyl methyl cellulose acetate succinate phthalate, hydroxypropyl methyl cellulose succinate phthalate, cellulose propionate phthalate, hydroxypropyl cellulose butyrate phthalate, cellulose acetate trimellitate, methyl cellulose acetate trimellitate, ethyl cellulose acetate trimellitate, hydroxypropyl cellulose acetate trimellitate, hydroxypropyl methyl cellulose acetate trimellitate, hydroxypropyl cellulose acetate trimellitate succinate, cellulose propionate trimellitate, cellulose butyrate trimellitate, cellulose acetate terephthalate, cellulose acetate isophthalate, cellulose acetate pyridinedicarboxylate, salicylic acid cellulose acetate, hydroxypropyl salicylic acid cellulose acetate, ethylbenzoic acid cellulose acetate, hydroxypropyl ethylbenzoic acid cellulose acetate, ethyl phthalic acid cellulose acetate, ethyl nicotinic acid cellulose acetate, and ethyl picolinic acid cellulose acetate.

Exemplary cellulosic polymers that meet the definition of amphiphilic, having hydrophilic and hydrophobic regions include polymers such as cellulose acetate phthalate and cellulose acetate trimellitate where the cellulosic repeat units that have one or more acetate substituents are hydrophobic relative to those that have no acetate substituents or have one or more ionized phthalate or trimellitate substituents.

A particularly desirable subset of cellulosic ionizable polymers are those that possess both a carboxylic acid functional aromatic substituent and an alkylate substituent and thus are amphiphilic. Exemplary polymers include cellulose acetate phthalate, methyl cellulose acetate phthalate, ethyl cellulose acetate phthalate, hydroxypropyl cellulose acetate phthalate, hydroxylpropyl methyl cellulose phthalate, hydroxypropyl methyl cellulose acetate phthalate, hydroxypropyl cellulose acetate phthalate succinate, cellulose propionate phthalate, hydroxypropyl cellulose butyrate phthalate, cellulose acetate trimellitate, methyl cellulose acetate trimellitate, ethyl cellulose acetate trimellitate, hydroxypropyl cellulose acetate trimellitate, hydroxypropyl methyl cellulose acetate trimellitate, hydroxypropyl cellulose acetate trimellitate succinate, cellulose propionate trimellitate, cellulose butyrate trimellitate, cellulose acetate terephthalate, cellulose acetate isophthalate, cellulose acetate pyridinedicarboxylate, salicylic acid cellulose acetate, hydroxypropyl salicylic acid cellulose acetate, ethylbenzoic acid cellulose acetate, hydroxypropyl ethylbenzoic acid cellulose acetate, ethyl phthalic acid cellulose acetate, ethyl nicotinic acid cellulose acetate, and ethyl picolinic acid cellulose acetate.

Another particularly desirable subset of cellulosic ionizable polymers are those that possess a non-aromatic carboxylate substituent. Exemplary polymers include hydroxypropyl methyl cellulose acetate succinate, hydroxypropyl methyl cellulose succinate, hydroxypropyl cellulose acetate succinate, hydroxyethyl methyl cellulose acetate succinate, hydroxyethyl methyl cellulose succinate, and hydroxyethyl cellulose acetate succinate.

While, as listed above, a wide range of polymers may be used to form dispersions of CETP inhibitors, the inventors have found that relatively hydrophobic polymers have shown the best performance as demonstrated by high MDC and AUC values. In particular, cellulosic polymers that are aqueous insoluble in their nonionized state but are aqueous soluble in their ionized state perform particularly well. A particular subclass of such polymers are the so-called "enteric" polymers which include, for example, certain grades of hydroxypropyl methyl cellulose acetate phthalate and cellulose acetate trimellitate. Dispersions formed from such polymers generally show very large enhancements, on the order of 50-fold to over 1000-fold, in the maximum drug concentration achieved in dissolution tests relative to that for a crystalline drug control. In addition, non-enteric grades of such polymers as well as closely related cellulosic polymers are expected to perform well due to the similarities in physical properties within the CETP inhibitor class.

Thus, especially preferred polymers are hydroxypropyl methyl cellulose acetate succinate (HPMCAS), hydroxypropyl methyl cellulose phthalate (HPMCP), cellulose acetate phthalate (CAP), cellulose acetate trimellitate (CAT), methyl cellulose acetate phthalate, hydroxypropyl cellulose acetate phthalate, cellulose acetate terephthalate and cellulose acetate isophthalate. The most preferred polymers are hydroxypropyl methyl cellulose acetate succinate, hydroxypropyl methyl cellulose phthalate, cellulose acetate phthalate, and cellulose acetate trimellitate.

While specific polymers have been discussed as being suitable for use in the compositions of the present invention, blends of such polymers may also be suitable. Thus the term "polymer" is intended to include blends of polymers in addition to a single species of polymer.

To obtain the best performance, particularly upon storage for long times prior to use, it is preferred that the CETP inhibitor remain, to the extent possible, in the amorphous state. The inventors have found that this is best achieved when the glass-transition temperature, $T_g$, of the amorphous CETP inhibitor material is substantially above the storage temperature of the composition. In particular, it is preferable that the $T_g$ of the amorphous state of the CETP inhibitor be at least 40° C. and preferably at least 60° C. For those aspects of the invention in which the composition is a solid, substantially amorphous dispersion of CETP inhibitor in the concentration-enhancing polymer and in which the CETP inhibitor itself has a relatively low $T_g$ (about 70° C. or less) it is preferred that the concentration-enhancing polymer have a $T_g$ of at least 40° C., preferably at least 70° C. and more preferably greater than 100° C. Exemplary high $T_g$ polymers include HPMCAS, HPMCP, CAP, CAT and other cellulosics that have alkylate or aromatic substituents or both alkylate and aromatic substituents.

In addition, the preferred polymers listed above, that is amphiphilic cellulosic polymers, tend to have greater concentration-enhancing properties relative to the other polymers of the present invention. For any particular CETP inhibitor, the amphiphilic cellulosic with the best concentration-enhancing properties may vary. However, the inventors have found that generally those that have ionizable substituents tend to perform best. In vitro tests of compositions with such polymers tend to have higher MDC and AUC values than compositions with other polymers of the invention.

Preparation of Compositions

Dispersions of the CETP inhibitor and concentration-enhancing polymer may be made according to any known process which results in at least a major portion (at least 60%) of the CETP inhibitor being in the amorphous state. Exemplary mechanical processes include milling and extrusion; melt processes include high temperature fusion, solvent modified fusion and melt-congeal processes; and solvent processes include non-solvent precipitation, spray coating and spray-drying. Although the dispersions of the present invention may be made by any of these processes, the dispersions generally have their maximum bioavailability and stability when the CETP inhibitor is dispersed in the polymer such that it is substantially amorphous and substantially homogeneously distributed throughout the polymer.

In general, as the degree of homogeneity of the dispersion increases, the enhancement in the aqueous concentration of the CETP inhibitor and relative bioavailability increases as well. Given the extremely low aqueous solubility and bioavailability of many CETP inhibitors, it is often highly preferred for the dispersions to be as homogeneous as possible to achieve therapeutically effective levels of CETP inhibitors. Thus, most preferred are dispersions having a single glass transition temperature, which indicates a high degree of homogeneity.

Although in some cases substantially amorphous and substantially homogeneous dispersions may be made by any of the methods described above, it has been found that such dispersions are preferably formed by "solvent processing," which consists of dissolution of the CETP inhibitor and one or more polymers in a common solvent. "Common" here means that the solvent, which can be a mixture of compounds, will simultaneously dissolve the drug and the polymer(s). After both the CETP inhibitor and the polymer have been dissolved, the solvent is rapidly removed by evaporation or by mixing with a non-solvent. Exemplary processes are spray-drying, spray-coating (pan-coating, fluidized bed coating, etc.), and precipitation by rapid mixing of the polymer and drug solution with $CO_2$, water, or some other non-solvent. Preferably, removal of the solvent results in a solid dispersion which is substantially homogeneous. As described previously, in such substantially homogeneous dispersions, the CETP inhibitor is dispersed as homogeneously as possible throughout the polymer and can be thought of as a solid solution of CETP inhibitor dispersed in the polymer(s). When the resulting dispersion constitutes a solid solution of CETP inhibitor in polymer, the dispersion may be thermodynamically stable, meaning that the concentration of CETP inhibitor in the polymer is at or below its equilibrium value, or it may be considered a supersaturated solid solution where the CETP inhibitor concentration in the dispersion polymer(s) is above its equilibrium value.

The solvent may be removed through the process of spray-drying. The term spray-drying is used conventionally and broadly refers to processes involving breaking up liquid mixtures into small droplets (atomization) and rapidly removing solvent from the mixture in a container (spray-drying apparatus) where there is a strong driving force for evaporation of solvent from the droplets. The strong driving force for solvent evaporation is generally provided by maintaining the partial pressure of solvent in the spray-drying apparatus well below the vapor pressure of the solvent at the temperature of the drying droplets. This is accomplished by either (1) maintaining the pressure in the spray-drying apparatus at a partial vacuum (e.g., 0.01 to 0.50 atm); (2) mixing the liquid droplets with a warm drying gas; or (3) both. In addition, at least a portion of the heat required for evaporation of solvent may be provided by heating the spray solution.

Solvents suitable for spray-drying can be any organic compound in which the CETP inhibitor and polymer are mutually soluble. Preferably, the solvent is also volatile with a boiling point of 150° C. or less. In addition, the solvent should have relatively low toxicity and be removed from the dispersion to a level that is acceptable according to The International Committee on Harmonization (ICH) guidelines. Removal of solvent to this level may require a processing step such as tray-drying subsequent to the spray-drying or spray-coating process. Preferred solvents include alcohols such as methanol, ethanol, n-propanol, iso-propanol, and butanol; ketones such as acetone, methyl ethyl ketone and methyl iso-butyl ketone; esters such as ethyl acetate and propylacetate; and various other solvents such as acetonitrile, methylene chloride, toluene, and 1,1,1-trichloroethane. Lower volatility solvents such as dimethyl acetamide or dimethylsulfoxide can also be used. Mixtures of solvents, such as 50% methanol and 50% acetone, can also be used, as can mixtures with water as long as the polymer and CETP inhibitor are sufficiently soluble to make the spray-drying process practicable. Generally, due to the hydrophobic nature of CETP inhibitors, non-aqueous solvents are preferred meaning that the solvent comprises less than about 10 wt % water, and preferably less than 1 wt % water.

Generally, the temperature and flow rate of the drying gas is chosen so that the polymer/drug-solution droplets are dry enough by the time they reach the wall of the apparatus that they are essentially solid, and so that they form a fine powder and do not stick to the apparatus wall. The actual length of time to achieve this level of dryness depends on the size of the droplets. Droplet sizes generally range from 1 µm to 500 µm in diameter, with 5 to 100 µm being more typical. The large surface-to-volume ratio of the droplets and the large driving force for evaporation of solvent leads to actual drying times of a few seconds or less, and more typically less than 0.1 second. This rapid drying is often critical to the particles maintaining a uniform, homogeneous dispersion instead of separating into drug-rich and polymer-rich phases. As above, to get large enhancements in concentration and bioavailability it is often necessary to obtain as homogeneous of a dispersion as possible. Solidification times should be less than 100 seconds, preferably less than a few seconds, and more preferably less than 1 second. In general, to achieve this rapid solidification of the CETP inhibitor/polymer solution, it is preferred that the size of droplets formed during the spray-drying process are less than about 100 µm in diameter. The resultant solid particles thus formed are generally less than about 100 µm in diameter.

Following solidification, the solid powder typically stays in the spray-drying chamber for about 5 to 60 seconds, further evaporating solvent from the solid powder. The final solvent content of the solid dispersion as it exits the dryer should be low, since this reduces the mobility of CETP inhibitor molecules in the dispersion, thereby improving its stability. Generally, the solvent content of the dispersion as it leaves the spray-drying chamber should be less than 10 wt % and preferably less than 2 wt %. In some cases, it may be preferable to spray a solvent or a solution of a polymer or other excipient into the spray-drying chamber to form granules, so long as the dispersion is not adversely affected.

Spray-drying processes and spray-drying equipment are described generally in Perry's *Chemical Engineers' Handbook*, Sixth Edition (R. H. Perry, D. W. Green, J. O. Maloney, eds.) McGraw-Hill Book Co. 1984, pages 20-54 to 20-57. More details on spray-drying processes and equipment are reviewed by Marshall "Atomization and Spray-Drying," 50 *Chem. Eng. Prog. Monogr. Series* 2 (1954).

The amount of concentration-enhancing polymer relative to the amount of CETP inhibitor present in the dispersions of the present invention depends on the CETP inhibitor and polymer and may vary widely from a CETP inhibitor-to-polymer weight ratio of from 0.01 to about 4 (e.g., 1 wt % CETP inhibitor to 80 wt % CETP inhibitor) However, in most cases it is preferred that the CETP inhibitor-to-polymer ratio is greater than about 0.05 (4.8 wt % CETP inhibitor) and less than about 2.5 (71 wt % CETP inhibitor). Often the enhancement in CETP inhibitor concentration or relative bioavailability that is observed increases as the CETP inhibitor-to-polymer ratio decreases from a value of about 1 (50 wt % CETP inhibitor) to a value of about 0.11 (10 wt % CETP inhibitor). In some cases it has been found that the bioavailability of dispersions with a CETP-inhibitor-to-polymer ratio of about 0.33 (25 wt % CETP inhibitor) have higher bioavailability when dosed orally than dispersions with a CETP-inhibitor-to-polymer ratio of 0.11 (10 wt % CETP inhibitor). The CETP inhibitor:polymer ratio that yields optimum results varies from CETP inhibitor to CETP inhibitor and is best determined in in vitro dissolution tests and/or in vivo bioavailability tests.

In addition, the amount of concentration-enhancing polymer that can be used in a dosage form is often limited by the total mass requirements of the dosage form. For example, when oral dosing to a human is desired, at low CETP inhibitor-to-polymer ratios the total mass of drug and polymer may be unacceptably large for delivery of the desired dose in a single tablet or capsule. Thus, it is often necessary to use CETP inhibitor-to-polymer ratios that are less than optimum in specific dosage forms to provide a sufficient CETP inhibitor dose in a dosage form that is small enough to be easily delivered to a use environment.

Excipients and Dosage Forms

Although the key ingredients present in the compositions of the present invention are simply the CETP inhibitor to be delivered and the concentration-enhancing polymer(s), the inclusion of other excipients in the composition may be useful. These excipients may be utilized with the CETP inhibitor and polymer composition in order to formulate the composition into tablets, capsules, suspensions, powders for suspension, creams, transdermal patches, depots, and the like. The composition of CETP inhibitor and polymer can be added to other dosage form ingredients in essentially any manner that does not substantially alter the CETP inhibitor. The excipients may be either physically mixed with the dispersion and/or included within the dispersion.

One very useful class of excipients is surfactants. Suitable surfactants include fatty acid and alkyl sulfonates; commercial surfactants such as benzalkonium chloride (HYAMINE® 1622, available from Lonza, Inc., Fairlawn, N.J.); dioctyl sodium sulfosuccinate, DOCUSATE SODIUM™ (available from Mallinckrodt Spec. Chem., St. Louis, Mo.); polyoxyethylene sorbitan fatty acid esters (TWEEN®, available from ICI Americas Inc., Wilmington, Del.; LIPOSORB® P-20 available from Lipochem Inc., Patterson N.J.; CAPMUL® POE-0 available from Abitec Corp., Janesville, Wis.), and natural surfactants such as sodium taurocholic acid, 1-palmitoyl-2-oleoyl-sn-glycero-3-phosphocholine, lecithin, and other phospholipids and mono- and diglycerides. Such materials can advantageously be employed to increase the rate of dissolution by facilitating wetting, thereby increasing the maximum dissolved concentration, and also to inhibit crystallization or precipitation of drug by interacting with the dissolved drug by mechanisms such as complexation, formation of inclusion complexes, formation of micelles or adsorbing to the surface of solid drug, crystalline or amorphous. These surfactants may comprise up to 5 wt % of the composition.

The addition of pH modifiers such as acids, bases, or buffers may also be beneficial, retarding the dissolution of the composition (e.g., acids such as citric acid or succinic acid when the concentration-enhancing polymer is anionic) or, alternatively, enhancing the rate of dissolution of the composition (e.g., bases such as sodium acetate or amines when the polymer is anionic).

Conventional matrix materials, complexing agents, solubilizers, fillers, disintegrating agents (disintegrants), or binders may also be added as part of the composition itself or added by granulation via wet or mechanical or other means. These materials may comprise up to 90 wt % of the composition.

Examples of matrix materials, fillers, or diluents include lactose, mannitol, xylitol, microcrystalline cellulose, calcium diphosphate, and starch.

Examples of disintegrants include sodium starch glycolate, sodium alginate, carboxy methyl cellulose sodium, methyl cellulose, and croscarmellose sodium.

Examples of binders include methyl cellulose, microcrystalline cellulose, starch, and gums such as guar gum, and tragacanth.

Examples of lubricants include magnesium stearate and calcium stearate.

Other conventional excipients may be employed in the compositions of this invention, including those excipients well-known in the art. Generally, excipients such as pigments, lubricants, flavorants, and so forth may be used for customary purposes and in typical amounts without adversely affecting the properties of the compositions. These excipients may be utilized in order to formulate the composition into tablets, capsules, suspensions, powders for suspension, creams, transdermal patches, and the like.

The compositions of the present invention may be delivered by a wide variety of routes, including, but not limited to, oral, nasal, rectal, and pulmonary. Generally, the oral route is preferred.

Compositions of this invention may also be used in a wide variety of dosage forms for administration of CETP inhibitors. Exemplary dosage forms are powders or granules that may be taken orally either dry or reconstituted by addition of water or other liquids to form a paste, slurry, suspension or solution; tablets; capsules; multiparticulates; and pills. Various additives may be mixed, ground, or granulated with the compositions of this invention to form a material suitable for the above dosage forms.

The compositions of the present invention may be formulated in various forms such that they are delivered as a suspension of particles in a liquid vehicle. Such suspensions may be formulated as a liquid or paste at the time of manufacture, or they may be formulated as a dry powder with a liquid, typically water, added at a later time but prior to oral administration. Such powders that are constituted into a suspension are often termed sachets or oral powder for constitution (OPC) formulations. Such dosage forms can be formulated and reconstituted via any known procedure. The simplest approach is to formulate the dosage form as a dry powder that is reconstituted by simply adding water and agitating. Alternatively, the dosage form may be formulated as a liquid and a dry powder that are combined and agitated to form the oral suspension. In yet another embodiment, the dosage form can be formulated as two powders which are reconstituted by first adding water to one powder to form a solution to which the second powder is combined with agitation to form the suspension.

Generally, it is preferred that the dispersion of CETP inhibitor be formulated for long-term storage in the dry state as this promotes the chemical and physical stability of the CETP inhibitor. Various excipients and additives are combined with the compositions of the present invention to form the dosage form. For example, it may be desirable to add some or all of the following: preservatives such as sulfites (an antioxidant), benzalkonium chloride, methyl paraben, propyl paraben, benzyl alcohol or sodium benzoate; suspending agents or thickeners such as xanthan gum, starch, guar gum, sodium alginate, carboxymethyl cellulose, sodium carboxymethyl cellulose, methyl cellulose, hydroxypropyl methyl cellulose, polyacrylic acid, silica gel, aluminum silicate, magnesium silicate, or titanium dioxide; anticaking agents or fillers such as silicon oxide, or lactose; flavorants such as natural or artificial flavors; sweeteners such as sugars such as sucrose, lactose, or sorbitol as well as artificial sweeteners such as aspartame or saccharin; wetting agents or surfactants such as various grades of polysorbate, docusate sodium, or sodium lauryl sulfate; solubilizers such as ethanol propylene glycol or polyethylene glycol; coloring agents such as FD and C Red No. 3 or FD and C Blue No. 1; and pH modifiers or buffers such as carboxylic acids (including citric acid, ascorbic acid, lactic acid, and succinic acid), various salts of carboxylic acids, amino acids such as glycine or alanine, various phosphate, sulfate and carbonate salts such as trisodium phosphate, sodium bicarbonate or potassium bisulfate, and bases such as amino glucose or triethanol amine.

A preferred additive to such formulations is additional concentration-enhancing polymer which may act as a thickener or suspending agent as well as to enhance the concentration of CETP inhibitor in the environment of use and may also act to prevent or retard precipitation or crystallization of CETP inhibitor from solution. Such preferred additives are hydroxyethyl cellulose, hydroxypropyl cellulose, and hydroxypropyl methyl cellulose. In particular, the salts of carboxylic acid functional polymers such as cellulose acetate phthalate, hydroxypropyl methyl cellulose acetate succinate, and carboxymethyl cellulose are useful in this regard. Such polymers may be added in their salt forms or the salt form may be formed in situ during reconstitution by adding a base such as trisodium phosphate and the acid form of such polymers.

In some cases, the overall dosage form or particles, granules or beads that make up the dosage form may have superior performance if coated with an enteric polymer to prevent or retard dissolution until the dosage form leaves the stomach. Exemplary enteric coating materials include hydroxypropyl methyl cellulose acetate succinate, hydroxypropyl methyl cellulose phthalate, cellulose acetate phthalate, cellulose acetate trimellitate, carboxylic acid-functionalized polymethacrylates, and carboxylic acid-functionalized polyacrylate.

Compositions of this invention may be administered in a controlled release dosage form. In one such dosage form, the composition of the CETP inhibitor and polymer is incorporated into an erodible polymeric matrix device. By an erodible matrix is meant aqueous-erodible or water-swellable or aqueous-soluble in the sense of being either erodible or swellable or dissolvable in pure water or requiring the presence of an acid or base to ionize the polymeric matrix sufficiently to cause erosion or dissolution. When contacted with the aqueous environment of use, the erodible polymeric matrix imbibes water and forms an aqueous-swollen gel or "matrix" that entraps the dispersion of CETP inhibitor and polymer. The aqueous-swollen matrix gradually erodes, swells, disintegrates or dissolves in the environment of use, thereby controlling the release of the dispersion to the environment of use. Examples of such dosage forms are disclosed more fully in commonly assigned pending U.S. patent application Ser. No. 09/495,059 filed Jan. 31, 2000 which claimed the benefit of priority of provisional patent application Ser. No. 60/119,400 filed Feb. 10, 1999, the relevant disclosure of which is herein incorporated by reference.

Alternatively, the compositions of the present invention may be administered by or incorporated into a non-erodible matrix device.

Alternatively, the compositions of the invention may be delivered using a coated osmotic controlled release dosage form. This dosage form has two components: (a) the core which contains an osmotic agent and the dispersion of CETP inhibitor and concentration-enhancing polymer; and (b) a non-dissolving and non-eroding coating surrounding the core, the coating controlling the influx of water to the core from an aqueous environment of use so as to cause drug release by extrusion of some or all of the core to the environment of use. The osmotic agent contained in the core of this device may be an aqueous-swellable hydrophilic polymer, osmogen, or osmagent. The coating is preferably polymeric, aqueous-permeable, and has at least one delivery port. Examples of such dosage forms are disclosed more fully in commonly assigned pending U.S. patent application Ser. No. 09/495,061 filed Jan. 31, 2000 which claimed the benefit of priority of provisional Patent Application Ser. No. 60/119, 406 filed Feb. 10, 1999, the relevant disclosure of which is herein incorporated by reference.

Alternatively, the compositions may be delivered via a coated hydrogel controlled release form having at least two components: (a) a core comprising the dispersion of the present invention and a hydrogel, and (b) a coating through which the dispersion has passage when the dosage form is exposed to a use environment. Examples of such dosage forms are more fully disclosed in commonly assigned European Patent EP0378404, the relevant disclosure of which is herein incorporated by reference.

Alternatively, the drug mixture of the invention may be delivered via a coated hydrogel controlled release dosage form having at least three components: (a) a composition containing the dispersion, (b) a water-swellable composition wherein the water-swellable composition is in a separate region within a core formed by the drug-containing composition and the water-swellable composition, and (c) a coating around the core that is water-permeable, water-insoluble, and has at least one delivery port therethrough. In use, the core imbibes water through the coating, swelling the water-swellable composition and increasing the pressure within the core, and fluidizing the dispersion-containing composition. Because the coating remains intact, the dispersion-containing composition is extruded out of the delivery port into an environment of use. Examples of such dosage forms are more fully disclosed in commonly assigned pending Provisional Application Ser. No. 60/171,968 filed Dec. 23, 1999, the relevant disclosure of which is herein incorporated by reference.

Alternatively, the compositions may be administered as multiparticulates. Multiparticulates generally refer to dosage forms that comprise a multiplicity of particles that may range in size from about 10 μm to about 2 mm, more typically about 100 μm to 1 mm in diameter. Such multiparticulates may be packaged, for example, in a capsule such as a gelatin capsule or a capsule formed from an aqueous-soluble polymer such as HPMCAS, HPMC or starch or they may be dosed as a suspension or slurry in a liquid.

Such multiparticulates may be made by any known process, such as wet- and dry-granulation processes, extrusion/spheronization, roller-compaction, or by spray-coating seed cores. For example, in wet- and dry-granulation processes, the composition of CETP inhibitor and concentration-enhancing polymer is prepared as described above. This composition is then granulated to form multiparticulates of the desired size. Other excipients, such as a binder (e.g., microcrystalline cellulose), may be blended with the composition to aid in processing and forming the multiparticulates. In the case of wet granulation, a binder such as microcrystalline cellulose may be included in the granulation fluid to aid in forming a suitable multiparticulate.

In any case, the resulting particles may themselves constitute the multiparticulate dosage form or they may be coated by various film-forming materials such as enteric polymers or water-swellable or water-soluble polymers, or they may be combined with other excipients or vehicles to aid in dosing to patients.

Compositions of the present invention may be used to treat any condition which is subject to treatment by administering a CETP inhibitor.

One aspect of this invention is directed to a method for treating atherosclerosis in a mammal (including a human being) by administering to a mammal in need of such treatment an atherosclerotic treating amount of a composition of the present invention.

Yet another aspect of this invention is directed to a method for treating peripheral vascular disease in a mammal (including a human being) by administering to a mammal in need of such treatment a peripheral vascular disease treating amount of a composition of the present invention.

Yet another aspect of this invention is directed to a method for treating dyslipidemia in a mammal (including a human being) by administering to a mammal in need of such treatment a dyslipidemia treating amount of a composition of the present invention.

Yet another aspect of this invention is directed to a method for treating hyperbetalipoproteinemia in a mammal (including a human being) by administering to a mammal in need of such treatment a hyperbetalipoproteinemia treating amount of a composition of the present invention.

Yet another aspect of this invention is directed to a method for treating hypoalphalipoproteinemia in a mammal (including a human being) by administering to a mammal in need of such treatment a hypoalphalipoproteinemia treating amount of a composition of the present invention.

Yet another aspect of this invention is directed to a method for treating hypercholesterolemia in a mammal (including a human being) by administering to a mammal in need of such treatment a hypercholesterolemia treating amount of a composition of the present invention.

Yet another aspect of this invention is directed to a method for treating hypertriglyceridemia in a mammal (including a human being) by administering to a mammal in need of such treatment a hypertriglyceridemia treating amount of a composition of the present invention.

Yet another aspect of this invention is directed to a method for treating familial hypercholesterolemia in a mammal (including a human being) by administering to a mammal in need of such treatment a familial-hypercholesterolemia treating amount of a composition of the present invention.

Yet another aspect of this invention is directed to a method for treating cardiovascular disorders in a mammal (including a human being) by administering to a mammal in need of such treatment a cardiovascular disorder treating amount of a composition of the present invention.

Yet another aspect of this invention is directed to a method for treating angina in a mammal (including a human being) by administering to a mammal in need of such treatment an angina treating amount of a composition of the present invention.

Yet another aspect of this invention is directed to a method for treating ischemia in a mammal (including a human being) by administering to a mammal in need of such treatment an ischemic disease treating amount of a composition of the present invention.

Yet another aspect of this invention is directed to a method for treating cardiac ischemia in a mammal (including a human being) by administering to a mammal in need of such treatment a cardiac ischemic treating amount of a composition of the present invention.

Yet another aspect of this invention is directed to a method for treating stroke in a mammal (including a human being) by administering to a mammal in need of such treatment a stroke treating amount of a composition of the present invention.

Yet another aspect of this invention is directed to a method for treating a myocardial infarction in a mammal (including a human being) by administering to a mammal in need of such treatment a myocardial infarction treating amount of a composition of the present invention.

Yet another aspect of this invention is directed to a method for treating reperfusion injury in a mammal (including a human being) by administering to a mammal in need of such treatment a reperfusion injury treating amount of a composition of the present invention.

Yet another aspect of this invention is directed to a method for treating angioplastic restenosis in a mammal (including a human being) by administering to a mammal in need of such treatment an angioplastic restenosis treating amount of a composition of the present invention.

Yet another aspect of this invention is directed to a method for treating hypertension in a mammal (including a human being) by administering to a mammal in need of such treatment a hypertension treating amount of a composition of the present invention.

Yet another aspect of this invention is directed to a method for treating the vascular complications of diabetes in a mammal (including a human being) by administering to a mammal in need of such treatment a vascular complications of diabetes treating amount of a composition of the present invention.

Yet another aspect of this invention is directed to a method for treating obesity in a mammal (including a human being) by administering to a mammal in need of such treatment an obesity treating amount of a composition of the present invention.

Yet another aspect of this invention is directed to a method for treating endotoxemia in a mammal (including a human being) by administering to a mammal in need of such treatment an endotoxemia treating amount of a composition of the present invention.

Other features and embodiments of the invention will become apparent from the following examples which are given for illustration of the invention rather than for limiting its intended scope.

EXAMPLES

Example 1

This example discloses preparation of an amorphous solid dispersion of [2R,4R]4-[(3,5-bis-trifluoromethyl-benzyl)-methoxycarbonyl-amino]-2-cyclopropyl-6-trifluoromethyl-3,4-dihydro-2H-quinoline-1-carboxylic acid isopropyl ester ("Drug 1"), which has a solubility in water of less than 1 µg/mL and a Clog P value of 7.6. A dispersion of 10 wt % Drug 1 and 90 wt % polymer was made by mixing Drug 1 in the solvent acetone together with a "medium fine" (AQUOT-MF) grade of the cellulosic ester polymer HPMCAS (manufactured by Shin Etsu) to form a solution. The solution comprised 0.053 wt % Drug 1, 0.477 wt % HPMCAS, and 99.47 wt % acetone. The dispersion was prepared using a "mini" spray-dryer, which consisted of an atomizer in the top cap of a vertically oriented stainless steel pipe. The atomizer was a two-fluid nozzle (Spraying Systems Co. 1650 fluid cap and 64 air cap), where the atomizing gas was nitrogen delivered to the nozzle at 10° C. and a flow rate of 15 µm/min, and the solution to be spray dried was delivered to the nozzle at room temperature and a flow rate of 1.3 mL/min using a syringe pump. Filter paper with a supporting screen was clamped to the bottom end of the pipe to collect the solid spray-dried material and allow the nitrogen and evaporated solvent to escape. These SDD preparation parameters are summarized in Table 1.

Control 1

Comparative composition Control 1 was simply 0.18 mg crystalline Drug 1.

Examples 2-3

Spray-dried dispersions were prepared using the procedure described in Example 1 except that the concentration-enhancing polymer was varied as noted in Table 1.

Example 4

A spray-dried dispersion was prepared using the procedure described in Example 1 except that the ratio of Drug 1 to HPMCAS-MF was 1:1 (50 wt % Drug 1), as shown in Table 1.

TABLE 1

| Example | Drug 1 Mass (mg) | Aqueous-Soluble Polymer* | Polymer Mass (mg) | Solvent | Solvent Mass (g) | Spray Apparatus |
|---------|------------------|--------------------------|-------------------|---------|------------------|-----------------|
| 1 | 9 | HPMCAS-MF | 81 | acetone | 17 | mini |
| 2 | 3.8 | HPMCP | 33.7 | acetone | 6 | mini |
| 3 | 3.5 | PVP | 31.5 | Acetone/MeOH | 6 0.12 | mini |
| 4 | 25 | HPMCAS-MF | 25 | acetone | 12 | mini |

*Polymer designations: HPMCAS = hydroxypropyl methyl cellulose acetate succinate; HPMCP = hydroxypropyl methyl cellulose phthalate; PVP = polyvinylpyrrolidone.

Example 5

The spray-dried dispersions of Examples 1 to 4 were evaluated in in vitro dissolution tests using a microcentrifuge method. In this method, 1 mg of the spray-dried dispersions was added to a 1.5-mL microcentrifuge tube. The tube was placed in a 37° C. sonicating bath, and 1 mL of a model-fasted duodenal solution (MFDS) (comprising sodium taurocholate/1-palmitoyl-2-oleoyl-sn-glycero-3-phosphocholine (NaTC-POPC) in phosphate-buffered saline (PBS) at pH 6.5 and 290 mOsm/kg) was added. The samples were quickly mixed using a combination of vortex mixer and sonication for about 90 seconds. The theoretical maximum concentration ("$TC_{max}$") of drug for Examples 1-3 if all the drug dissolved was 100 µg/mL, while for Example 4 the $TC_{max}$, was 500 µg/mL. The samples were centrifuged at 13,000 G at 37° C. for 1 minute. The resulting supernatant solution was then sampled (100 µL) and diluted with 200 µL methanol and then analyzed by HPLC. The tubes were then mixed on the vortex mixer and allowed to stand undisturbed at 37° C. until the next sample. Samples were collected at 3, 10, 30, 60, and 90 minutes and for Examples 1 and 2 at 1200 minutes. Data for Examples 1 to 4 are shown in Table 2.

For Control 1, an in vitro test was performed using the procedure described above, except that 0.18 mg of crystalline Drug 1 was placed in a microcentrifuge tube and mixed with 1.8 ml of MFDS. The test results are included in Table 2.

TABLE 2

| Example | Time (min) | Concentration (µg/mL) | AUC (min · µg/mL) |
|---|---|---|---|
| 1 | 0 | 0 | 0 |
|   | 3 | 83 | 120 |
|   | 10 | 79 | 690 |
|   | 30 | 85 | 2,300 |
|   | 60 | 84 | 4,900 |
|   | 90 | 77 | 7,300 |
|   | 1200 | 26 | 64,400 |
| 2 | 0 | 0 | 0 |
|   | 3 | 81 | 122 |
|   | 10 | 75 | 670 |
|   | 30 | 75 | 2,200 |
|   | 60 | 64 | 4,200 |
|   | 90 | 74 | 6,300 |
|   | 1200 | 21 | 58,700 |
| 3 | 0 | 0 | 0 |
|   | 3 | 35 | 53 |
|   | 10 | 33 | 290 |
|   | 30 | 30 | 900 |
|   | 60 | 28 | 1,800 |
|   | 90 | 28 | 2,600 |
| 4 | 0 | 0 | 0 |
|   | 3 | 62 | 94 |
|   | 10 | 63 | 530 |
|   | 30 | 54 | 1,700 |
|   | 60 | 52 | 3,300 |
|   | 90 | 40 | 4,700 |
| Control 1 | 0 | 0 | 0 |
|   | 4 | <0.1 | <0.1 |
|   | 10 | 0.3 | 1 |
|   | 20 | 0.3 | 4 |
|   | 40 | 0.9 | 16 |
|   | 90 | 0.8 | 57 |

TABLE 3

| Example | Aqueous-Soluble Polymer* | Concentration in the dispersion (wt %) | $TC_{max}$ (µg/mL) | $C_{max,90}$ (µg/mL) | $AUC_{90}$ (min · µg/mL) |
|---|---|---|---|---|---|
| 1 | HPMCAS-MF | 10 | 100 | 85 | 7300 |
| 2 | HPMCP | 10 | 100 | 81 | 6300 |
| 3 | PVP | 10 | 100 | 35 | 2600 |
| 4 | HPMCAS-MF | 50 | 500 | 63 | 4700 |
| Control 1 | None | — | 100 | 0.9 | 57 |

*Polymer designations: HPMCAS = hydroxypropyl methyl cellulose acetate succinate; HPMCP = hydroxypropyl methyl cellulose phthalate, PVP = polyvinylpyrrolidone.

The results of the in vitro dissolution tests are summarized in Table 3, which shows the maximum concentration of Drug 1 in solution during the 90-minute test ($C_{max,90}$), and the area under the aqueous concentration versus time curve during the 90-minute test ($AUC_{90}$). The results show that the performance of the spray-dried dispersions of Examples 1 to 4 was much better than that of the crystalline drug alone (Control 1), with $C_{max,90}$ values ranging from 39- to 94-fold that of the crystalline drug, Control 1, and $AUC_{90}$ values ranging from 45- to 128-fold that of the crystalline drug, Control 1.

Examples 6-7

Examples 6-7 demonstrates the utility of the amorphous dispersions of the present invention with another CETP inhibitor, [2R,4S]4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester ("Drug 2"), which has a solubility in water of <1 µg/ml, and a Clog P value of 7.5. To prepare Example 6, an amorphous solid dispersion of 25 wt % Drug 2 and 75 wt % polymer was made by mixing Drug 2 in the solvent acetone together with a "medium fine" (AQUOT-MF) grade of the cellulosic ester polymer HPMCAS (manufactured by Shin Etsu) to form a solution. The solution comprised 2.5 wt % Drug 2, 7.5 wt % HPMCAS, and 90 wt % acetone. This solution was then spray-dried by directing an atomizing spray using a two-fluid external-mix spray nozzle at 2.7 bar (37 psig) at a feed rate of 150 g/min into the stainless-steel chamber of a Niro PSD1 spray-dryer, maintained at a temperature of 155° C. at the inlet and 70° C. at the outlet. The preparation parameters are summarized in Table 4. The resulting amorphous solid spray-dried dispersion was collected via a cyclone and then dried in a Gruenberg solvent tray-dryer by spreading the spray-dried particles onto polyethylene-lined trays to a depth of not more than 1 cm and then drying them at 40° C. for 24 hours.

Example 7 was prepared following the general procedure described in Example 6 except that the dispersion contained 10 wt % Drug 2 and the spray solution comprised 1.0 wt % Drug 2, 9.0 wt % HPMCAS-MF, and 90 wt % acetone. The preparation parameters are summarized in Table 4.

TABLE 4

| Example | Drug 2 Mass (g) | Aqueous-Soluble Polymer | Polymer Mass (g) | Solvent | Solvent Mass (g) | Spray Apparatus |
|---|---|---|---|---|---|---|
| 6 | 100 | HPMCAS-MF | 300 | acetone | 3600 | PSD-1 |
| 7 | 100 | HPMCAS-MF | 900 | acetone | 9000 | PSD-1 |
| Control 2 | 0.0018 | none | — | — | — | — |

Comparative composition Control 2 consisted of 1.8 mg of the crystalline form of Drug 2 alone.

Example 8

The spray-dried dispersions of Examples 6 and 7 were evaluated in an in vitro dissolution test using a microcentrifuge method. In this test, the spray-dried dispersion was added to a microcentrifuge tube for a Drug 2 dose of about 1000 µg/mL (7.2 mg for Example 6, 18 mg for Example 7). The tube was placed in a 37° C. sonicating bath, and 1.8 mL phosphate buffered saline (PBS) at pH 6.5 and 290 mOsm/kg was added. The samples were quickly mixed using a vortex mixer for about 60 seconds. The samples were centrifuged at 13,000 G at 37° C. for 1 minute. The resulting supernatant solution was then sampled and diluted 1:6 (by volume) with methanol and then analyzed by high-performance liquid chromatography (HPLC). The contents of the tubes were mixed on the vortex mixer and allowed to stand undisturbed at 37° C. until the next sample was taken. Samples were collected at 4, 10, 20, 40, 90, and 1200 minutes. The concentrations of drug obtained in these samples are shown in Table 5.

For Control 2, an in vitro dissolution test was performed using the procedures described above except that 1.8 mg of crystalline Drug 2 was used. The concentrations of drug obtained in in vitro dissolution tests are shown in Table 5.

TABLE 5

| Example | Time (mins) | Drug 2 Concentration (µg/mL) | AUC (min · µg/mL) |
|---|---|---|---|
| 6 | 0 | 0 | 0 |
|  | 4 | 328 | 660 |
|  | 10 | 701 | 3,700 |
|  | 20 | 781 | 11,200 |
|  | 40 | 805 | 27,000 |
|  | 90 | 780 | 66,600 |
|  | 1200 | 439 | 743,200 |

| Example | Time (mins) | Drug 2 Concentration (µg/mL) | AUC (min · µg/mL) |
|---|---|---|---|
| 7 | 0 | 0 | 0 |
|  | 4 | 925 | 1,900 |
|  | 10 | 923 | 7,400 |
|  | 20 | 910 | 16,600 |
|  | 40 | 890 | 34,600 |
|  | 90 | 858 | 78,300 |
|  | 1200 | 623 | 900,200 |

-continued

| Example | Time (mins) | Drug 2 Concentration (µg/mL) | AUC (min · µg/mL) |
|---|---|---|---|
| Control 2 | 0 | 0 | 0 |
|  | 4 | 6 | 12 |
|  | 10 | <1 | 30 |
|  | 20 | <1 | 30 |
|  | 40 | 3 | 60 |
|  | 90 | <1 | 135 |
|  | 1200 | <1 | 135 |

The results of dissolution tests for Examples 6 and 7, and Control 2 are summarized in Table 6, which shows the maximum concentration of Drug 2 in solution during the first 90 minutes of the test ($C_{max,90}$), the area under the aqueous concentration versus time curve after 90 minutes ($AUC_{90}$), and the concentration at 1200 minutes ($C_{1200}$).

TABLE 6

| Example | Aqueous-Soluble Polymer | Drug 2 Conc. in the Dispersion (wt %) | Receptor Solution | $TC_{max}$ (µg/mL) | $C_{max,90}$ (µg/mL) | $AUC_{90}$ (min · µg/mL) | $C_{1200}$ (µg/mL) |
|---|---|---|---|---|---|---|---|
| 6 | HPMCAS-MF | 25 | PBS | 994 | 805 | 66,600 | 439 |
| 7 | HPMCAS-MF | 10 | PBS | 988 | 925 | 78,300 | 623 |
| Control 2 | None (crystalline drug) | NA | PBS | 1000 | 6 | 135 | <1 |

The results summarized in Table 6 above show that the dissolution results for the compositions of Examples 6 and 7 were much better than that of the crystalline drug alone, providing $C_{max,90}$ values that were 134-fold and 154-fold that of the crystalline drug (Control 2), respectively, and $AUC_{90}$ values that were 493-fold and 580-fold that of the crystalline drug (Control 2), respectively. It should be noted that the non zero concentrations of Drug 2 for Control 2 may be in error and the actual values were below the detection limit of about 1 µg/ml. Accurate measurements of the solubility of crystalline Drug 2 yield a value of about 0.01 µg/ml. Thus, the actual $C_{max,90}$ for Drug 2 in Control 2 is believed to be about 0.01 µg/ml. Using this value, the compositions of Examples 6 and 7 provided $C_{max,90}$ values that were about 80,000-fold to 92,500 fold that of the crystalline drug, and $AUC_{90}$ values that were about 70,000- to 80,000-fold that of the crystalline drug, respectively.

Examples 9-16

Spray-dried dispersions for Examples 9-16 were prepared using the procedure described in Example 1 (using a "mini" spray-dryer apparatus) except that Drug 2 was used instead of Drug 1. Other variables are summarized in Table 7.

Comparative composition Control 3 consisted of 0.72 mg of the crystalline form of Drug 2 alone.

TABLE 7

| Example | Drug 2 Mass (mg) | Aqueous-Soluble Polymer* | Polymer Mass (mg) | Solvent | Solvent Mass (g) | Spray Apparatus |
|---|---|---|---|---|---|---|
| 9 | 70 | HPMCAS-MF | 630 | acetone | 14 | mini |
| 10 | 70 | CAT | 630 | acetone | 14 | mini |

TABLE 7-continued

| Example | Drug 2 Mass (mg) | Aqueous-Soluble Polymer* | Polymer Mass (mg) | Solvent | Solvent Mass (g) | Spray Apparatus |
|---|---|---|---|---|---|---|
| 11 | 70 | CAP | 630 | acetone | 14 | mini |
| 12 | 250 | HPMCAS-MF | 750 | acetone | 75 | mini |
| 13 | 25 | CAP | 75 | acetone | 5 | mini |
| 14 | 3 | HPMC | 27 | Acetone/Methanol (1:1) | 10 | mini |
| 15 | 3 | HPMCP | 27 | Acetone | 10 | mini |
| 16 | 3 | PVP | 27 | Acetone/Methanol (9:1) | 10 | mini |

*Polymer designations: HPMCAS = hydroxypropyl methyl cellulose acetate succinate; CAT = cellulose acetate trimellitate, CAP = cellulose acetate phthalate, HPMC = hydroxypropyl methyl cellulose, HPMCP = hydroxypropyl methyl cellulose phthalate, PVP = polyvinylpyrrolidone.

Example 17

The dispersions of Examples 9-11 and 14 were evaluated in an in vitro dissolution test using receptor solutions of PBS using the procedures outlined in Example 8 except the $TC_{max}$ was either 400 µg/ml or 100 µg/ml as indicated in Table 9, depending on the amount of SDD added to the receptor solution. The data are presented in Table 8.

The dispersions of Examples 9-16 were also evaluated in an in vitro dissolution test using receptor solutions of MFDS using the procedures outlined in Example 8. The data are also presented in Table 8.

For Control 3, an in vitro dissolution test was performed using the procedure described above except that 0.72 mg of crystalline Drug 2 was used. The results are shown in Table 8.

TABLE 8

| Example | Receptor | Time (min) | Concentration (µg/ml) | AUC (min · µg/ml) |
|---|---|---|---|---|
| 9 | PBS | 0 | 0 | 0 |
|   |     | 4 | 370 | 740 |
|   |     | 10 | 364 | 2,940 |
|   |     | 20 | 356 | 6,500 |
|   |     | 40 | 336 | 13,500 |
|   |     | 90 | 318 | 29,800 |
|   |     | 1200 | 131 | 279,200 |
| 9 | MFDS | 0 | 0 | 0 |
|   |      | 4 | 391 | 780 |
|   |      | 10 | 388 | 3,120 |
|   |      | 20 | 384 | 7,000 |
|   |      | 40 | 372 | 14,500 |
|   |      | 90 | 340 | 32,300 |
|   |      | 1200 | 110 | 282,300 |
| 10 | PBS | 0 | 0 | 0 |
|    |     | 4 | 375 | 750 |
|    |     | 10 | 366 | 2,970 |
|    |     | 20 | 360 | 6,600 |
|    |     | 40 | 321 | 13,400 |
|    |     | 90 | 300 | 28,900 |
|    |     | 1200 | 54 | 225,900 |
| 10 | MFDS | 0 | 0 | 0 |
|    |      | 4 | 395 | 789 |
|    |      | 10 | 386 | 3,130 |
|    |      | 20 | 368 | 6,900 |
|    |      | 40 | 349 | 14,100 |
|    |      | 90 | 298 | 30,200 |
|    |      | 1200 | 92 | 246,400 |
| 11 | PBS | 0 | 0 | 0 |
|    |     | 4 | 383 | 764 |
|    |     | 10 | 381 | 3,050 |
|    |     | 20 | 360 | 6,800 |
|    |     | 40 | 338 | 13,800 |
|    |     | 90 | 302 | 29,600 |
|    |     | 1200 | 56 | 228,600 |
| 11 | MFDS | 0 | 0 | 0 |
|    |      | 4 | 409 | 818 |
|    |      | 10 | 380 | 3,190 |
|    |      | 20 | 374 | 7,000 |
|    |      | 40 | 357 | 14,300 |
|    |      | 90 | 326 | 31,300 |
|    |      | 1200 | 102 | 268,700 |
| 12 | MFDS | 0 | 0 | 0 |
|    |      | 4 | 136 | 272 |
|    |      | 10 | 168 | 1,180 |
|    |      | 20 | 161 | 2,800 |
|    |      | 40 | 145 | 5,900 |
|    |      | 90 | 122 | 12,600 |
|    |      | 1200 | 0 | 80,500 |
| 13 | MFDS | 0 | 0 | 0 |
|    |      | 4 | 285 | 571 |
|    |      | 10 | 277 | 2,260 |
|    |      | 20 | 245 | 4,900 |
|    |      | 40 | 218 | 9,500 |
|    |      | 90 | 176 | 19,400 |
|    |      | 1200 | 57 | 149,000 |
| 14 | PBS | 0 | 0 | 0 |
|    |     | 3 | 70 | 106 |
|    |     | 10 | 64 | 580 |
|    |     | 20 | 59 | 1,200 |
|    |     | 40 | 50 | 2,300 |
|    |     | 90 | 42 | 4,600 |
|    |     | 1200 | 18 | 37,900 |
| 14 | MFDS | 0 | 0 | 0 |
|    |      | 3 | 94 | 142 |
|    |      | 10 | 94 | 800 |
|    |      | 20 | 85 | 1,700 |
|    |      | 40 | 80 | 3,300 |
|    |      | 90 | 74 | 7,200 |
|    |      | 1200 | 28 | 63,700 |
| 15 | MFDS | 0 | 0 | 0 |
|    |      | 3 | 98 | 147 |
|    |      | 10 | 83 | 780 |
|    |      | 20 | 67 | 1,500 |
|    |      | 40 | 56 | 2,800 |
|    |      | 90 | 46 | 5,300 |
|    |      | 1200 | 25 | 44,500 |
| 16 | MFDS | 0 | 0 | 0 |
|    |      | 3 | 19 | 28 |
|    |      | 10 | 16 | 150 |
|    |      | 20 | 13 | 300 |
|    |      | 40 | 13 | 600 |
|    |      | 90 | 12 | 1,200 |
|    |      | 1200 | 15 | 16,100 |
| Control 3 | MFDS | 0 | 0 | 0 |
|    |      | 4 | <1 | <4 |
|    |      | 10 | <1 | <10 |
|    |      | 20 | <1 | <20 |
|    |      | 40 | <1 | <40 |
|    |      | 90 | <1 | <90 |

The results summarized in Table 9 show that the dissolution results for the compositions of Examples 9-16 were much better than that of the crystalline drug alone, providing $C_{max,90}$ values that were greater than 19- to 409-fold that of the crystalline drug (Control 3), when tested in MFDS, and $AUC_{90}$ values that were greater than 13- to 359-fold that of the crystalline drug (Control 3), when tested in MFDS.

TABLE 9

| Example | Aqueous-Soluble Polymer* | Conc. of Drug in the dispersion (wt %) | Receptor Solution | $TC_{max}$ (μg/mL) | $C_{max,90}$ (μg/mL) | $AUC_{90}$ (min·μg/mL) |
|---|---|---|---|---|---|---|
| 9 | HPMCAS-MF | 10 | PBS | 400 | 370 | 29,800 |
| 9 | HPMCAS-MF | 10 | MFDS | 400 | 391 | 32,300 |
| 10 | CAT | 10 | PBS | 400 | 375 | 28,900 |
| 10 | CAT | 10 | MFDS | 400 | 395 | 30,200 |
| 11 | CAP | 10 | PBS | 400 | 383 | 29,800 |
| 11 | CAP | 10 | MFDS | 400 | 409 | 31,300 |
| 12 | HPMCAS-MF | 25 | MFDS | 400 | 168 | 12,600 |
| 13 | CAP | 25 | MFDS | 400 | 285 | 19,400 |
| 14 | HPMC | 10 | PBS | 100 | 70 | 4,600 |
| 14 | HPMC | 10 | MFDS | 100 | 94 | 7,200 |
| 15 | HPMCP | 10 | MFDS | 100 | 98 | 5,300 |
| 16 | PVP | 10 | MFDS | 100 | 19 | 1,200 |
| Control 3 | None (crystalline drug) | NA | MFDS | 400 | <1 | <90 |

*Polymer designations: HPMCAS = hydroxypropyl methyl cellulose acetate succinate; CAT = cellulose acetate trimellitate, CAP = cellulose acetate phthalate, HPMC = hydroxypropyl methyl cellulose, HPMCP = hydroxypropyl methyl cellulose phthalate, PVP = polyvinylpyrrolidone.

cellulose, and 0.15 wt % polysorbate 80 in sterile water (Control 4). Dogs that had fasted overnight were dosed with the OPC. Blood was collected from the jugular vein of the dogs before dosing and at various time points after dosing. To 100 μL of each plasma sample, 5 mL of methyl-tert-butyl ether (MTBE) and 1 mL of 500 mM sodium carbonate buffer (pH 9) were added; the sample was vortexed for 1 minute and then centrifuged for 5 minutes. The aqueous portion of the sample was frozen in a dry-ice/acetone bath, and the MTBE layer was decanted and evaporated in a vortex evaporator. Dried samples were reconstituted in 100 μL of mobile phase (33% acetonitrile and 67% of 0.1% formic acid in water). Analysis was carried out by HPLC.

The results of these tests are shown in Table 11, where $C_{max,24}$ is the maximum concentration in the blood plasma during the first 24 hours, $T_{max}$ is the time to achieve the maximum concentration in the blood plasma and $AUC_{0-24}$ is the concentration in the blood plasma area under the curve in the first 24 hours. The results show that the $C_{max,24}$ and $AUC_{0-24}$ in the blood were much higher for the compositions of the present invention than the controls, with $C_{max,24}$ values that are 21.5- to 40-fold that of the crystalline drug (Control 4), and $AUC_{0-24}$ values that are 21.7- to 55.6-fold that of the crystalline drug (Control 4).

TABLE 11

| Example | Formulation | Dose (mg) | $C_{max,24}$ (mg/mL) | $T_{max}$ (hr) | $AUC_{0-24}$ (mg-hr/mL) |
|---|---|---|---|---|---|
| 18 | 25% Drug 2: HPMCAS OPC | 90 | 1.60 ± 0.60 | 1.10 ± 0.50 | 7.88 ± 2.95 |
| 19 | 10% Drug 2: HPMCAS OPC | 90 | 0.86 ± 1.75 | 2.17 ± 1.94 | 3.47 ± 1.71 |
| 20 | 10% Drug 2: CAP OPC | 90 | 1.51 ± 0.50 | 1.58 ± 1.28 | 8.89 ± 1.75 |
| Control 4 | Crystalline Drug 2 suspension | 90 | 0.04 ± 0.01 | 1.33 ± 0.52 | 0.16 ± 0.14 |

Examples 18-20

These examples demonstrate that the technology of this invention, when orally dosed to beagle dogs, gives a high systemic compound exposure ($C_{max}$ and AUC). Spray-dried dispersions were made using the procedures outlined in Examples 6, 7 and 11, and were used as an oral powder for constitution (OPC) by suspending 360 mg of the composition of Example 6 in about 15 mL of a solution of 3 wt % polyethylglycol (PEG) with a molecular weight of 3,350 daltons, 0.5 wt % methylcellulose, and 0.15 wt % Polysorbate 80 in sterile water (Example 18), suspending 900 mg of the composition of Example 7 in about 15 mL of a solution of 3 wt % PEG with a molecular weight of 3,350 daltons, 0.5 wt % methylcellulose, and 0.15 wt % Polysorbate 80 in sterile water (Example 19), and by suspending 900 mg of the composition of Example 11 in about 15 mL of a solution of 3 wt % PEG with a molecular weight of 3,350 daltons, 0.5 wt % methylcellulose, and 0.15 wt % Polysorbate 80 in sterile water (Example 20). A control OPC containing 90 mg of crystalline drug was also prepared by suspending 90 mg of crystalline drug in about 15 ml of a solution of 3 wt % PEG with a molecular weight of 3,350 daltons, 0.5 wt % methyl Examples 21-28

Example 21 demonstrates the utility of the amorphous dispersions of the present invention with another CETP inhibitor, [2R,4S]4-[(3,5-bis-trifluoromethyl-benzyl)-methoxycarbonyl-amino]-2-ethyl-6-trifluoromethyl-3,4-dihydro-2H-quinoline-1-carboxylic acid propyl ester ("Drug 3"), which has a solubility in water of less than 0.1 μg/ml, and a Clog P value of 8.0. To prepare Example 21, an amorphous solid dispersion of a CETP inhibitor comprising 10 wt % Drug 3 and 90 wt % polymer was made by mixing Drug 3 in the solvent acetone together with HPMCAS-MF to form a solution. The solution comprised 0.1 wt % Drug 3, 0.9 wt % HPMCAS, and 99 wt % acetone. This solution was pumped into a "mini" spray-dryer apparatus via a syringe pump at a rate of 1.3 mL/min. The polymer solution was atomized through a spray nozzle using a heated stream of nitrogen. The resulting solid spray-dried dispersion was collected on a filter paper at a yield of about 50%. The preparation parameters are summarized in Table 12.

Spray-dried dispersions were prepared using the procedure described to prepare Example 21 except that the aqueous-soluble polymer and sometimes the solvent was varied as noted in Table 12.

Comparative composition Control 5 consisted of 0.72 mg of the crystalline form of Drug 3 alone.

TABLE 12

| Example | Drug 3 Mass (mg) | Aqueous-Soluble Polymer* | Polymer Mass (mg) | Solvent | Solvent Mass (g) | Spray Apparatus |
|---|---|---|---|---|---|---|
| 21 | 20 | HPMCAS-MF | 180 | acetone | 20 | mini |
| 22 | 10 | HPMCP | 90 | acetone | 10 | mini |
| 23 | 10 | CAP | 90 | acetone | 10 | mini |
| 24 | 10 | CAT | 90 | acetone | 10 | mini |
| 25 | 10 | PVP | 90 | Acetone methanol | 9 1 | mini |
| 26 | 10 | HPMC | 90 | methanol | 10 | mini |
| 27 | 10 | HPMCAS-LF | 90 | acetone | 10 | mini |
| 28 | 10 | HPMCAS-HF | 90 | acetone | 10 | mini |

*Polymer designations: HPMCAS = hydroxypropyl methyl cellulose acetate succinate; HPMCP = hydroxypropyl methyl cellulose phthalate, CAP = cellulose acetate phthalate, CAT = cellulose acetate trimellitate, PVP = polyvinylpyrroildone, HPMC = hydroxypropyl methyl cellulose.

Example 29

The spray-dried dispersions of Examples 21-28 were evaluated in an in vitro dissolution test using a microcentrifuge method. In this method, 7.2 mg of each SDD was added to a 2-mL microcentrifuge tube. The tube was placed in a 37° C. sonicating bath, and 1.8 mL of a phosphate-buffered saline (PBS) solution at pH 6.5 and 290 mOsm/kg was added, resulting in a $TC_{max}$ of 400 µg/mL. The samples were quickly mixed using a combination of vortex mixer and sonication for about 90 seconds. The samples were centrifuged at 13,000 G at 37° C. for 1 minute. The resulting supernatant solution was then sampled and diluted 1:6 (by volume) with methanol and then analyzed by HPLC. The tubes were then mixed on the vortex mixer and allowed to stand undisturbed at 37° C. until the next sample. Samples were collected at 4, 10, 20, 40, 90 and 1200 minutes. Data are included in Table 13.

For Control 5, an in vitro dissolution test was performed using the procedure described above, except that 0.72 mg of non-crystalline Drug 3 was placed in a microcentrifuge tube and mixed with 1.8 mL of PBS. The test results are included in Table 14.

TABLE 13

| Example | Time (min) | Concentration (µg/mL) | AUC (min · µg/mL) |
|---|---|---|---|
| 21 | 0 | 0 | 0 |
| | 4 | 347 | 694 |
| | 10 | 361 | 2,800 |
| | 20 | 370 | 6,500 |
| | 60 | 396 | 14,000 |
| | 90 | 364 | 33,100 |
| | 1200 | 291 | 396,500 |
| 22 | 0 | 0 | 0 |
| | 4 | 373 | 685 |
| | 10 | 296 | 2,600 |
| | 20 | 264 | 5,400 |
| | 40 | 231 | 10,400 |
| | 90 | 174 | 20,500 |
| | 1200 | 33 | 135,000 |
| 23 | 0 | 0 | 0 |
| | 4 | 384 | 769 |
| | 10 | 368 | 3,000 |
| | 20 | 376 | 6,700 |
| | 40 | 356 | 14,100 |
| | 90 | 371 | 32,200 |
| | 1200 | 237 | 369,700 |
| 24 | 0 | 0 | 0 |
| | 4 | 390 | 780 |
| | 10 | 390 | 3,100 |
| | 20 | 386 | 7,000 |
| | 40 | 387 | 14,700 |
| | 90 | 379 | 33,900 |
| | 1200 | 231 | 372,400 |
| 25 | 0 | 0 | 0 |
| | 4 | 196 | 392 |
| | 10 | 158 | 1,500 |
| | 20 | 145 | 3,000 |
| | 40 | 134 | 5,800 |
| | 90 | 127 | 12,300 |
| | 1200 | 84 | 129,400 |
| 26 | 0 | 0 | 0 |
| | 4 | 346 | 693 |
| | 10 | 349 | 2,800 |
| | 20 | 343 | 6,200 |
| | 40 | 323 | 12,900 |
| | 90 | 296 | 28,400 |
| | 1200 | 209 | 308,700 |
| 27 | 0 | 0 | 0 |
| | 4 | 373 | 746 |
| | 10 | 348 | 2,900 |
| | 20 | 335 | 6,300 |
| | 40 | 315 | 12,800 |
| | 90 | 292 | 28,000 |
| | 1200 | 195 | 298,300 |
| 28 | 0 | 0 | 0 |
| | 4 | 72 | 144 |
| | 10 | 172 | 876 |
| | 20 | 316 | 3,300 |
| | 40 | 370 | 10,200 |
| | 90 | 405 | 29,600 |
| | 1200 | 355 | 451,400 |
| Control 5 | 0 | 0 | 0 |
| | 4 | <0.1 | <0.4 |
| | 10 | <0.1 | <1.0 |
| | 20 | <0.1 | <2.0 |
| | 40 | <0.1 | <4.0 |
| | 90 | <0.1 | <9.0 |

The results, summarized in Table 14, show that the dissolution results for the compositions of Examples 21 through 28 were much better than that of the crystalline drug alone, providing $C_{max,90}$ values that were greater than 1,900- to 4,050-fold that of the crystalline drug (Control 5), and $AUC_{90}$ values that were greater than 1,370- to 3,770-fold that of the crystalline drug (Control 5).

TABLE 14

| Example | Aqueous-Soluble Polymer* | Concentration of Drug 3 in Polymer (wt %) | $C_{max,90}$ (µg/mL) | $AUC_{90}$ (min · µg/mL) |
|---|---|---|---|---|
| 21 | HPMCAS-MF | 10 | 396 | 33,100 |
| 22 | HPMCP | 10 | 343 | 20,500 |
| 23 | CAP | 10 | 384 | 32,200 |
| 24 | CAT | 10 | 390 | 33,900 |
| 25 | PVP | 10 | 196 | 12,300 |
| 26 | HPMC | 10 | 349 | 28,400 |
| 27 | HPMCAS-LF | 10 | 373 | 28,000 |
| 28 | HPMCAS-HF | 10 | 405 | 29,600 |
| Control 5 | None | — | <0.1 | <9.0 |

*Polymer designations: HPMCAS = hydroxypropyl methyl cellulose acetate succinate; HPMCP = hydroxypropyl methyl cellulose phthalate, CAP = cellulose acetate phthalate, CAT = cellulose acetate trimellitate, PVP = polyvinylpyrrolidone, HPMC = hydroxypropyl methyl cellulose.

Examples 30-41

Examples 30 through 41 demonstrate the utility of the amorphous dispersions of the present invention with a variety of CETP inhibitors. The following drugs were all incorporated into amorphous solid dispersions: [2R,4S]4-[(3,5-bis-trifluoromethyl-benzyl)-methoxycarbonyl-amino]-6,7- dimethoxy-2-methyl-3,4-dihydro-2H-quinoline-1-carboxylic acid ethyl ester ("Drug 4"); [2R,4S]4-[(3,5-bis-trifluoromethyl-benzyl)-methoxycarbonyl-amino]-6,7-diethyl-2-methyl-3,4-dihydro-2H-quinoline-1-carboxylic acid ethyl ester ("Drug 5"); [2R,4S]4-[(3,5-bis-trifluoromethyl-benzyl)-methoxycarbonyl-amino]-2-methyl-2,3,4,6,7,8-hexahydro-cyclopenta[g]quinoline-1-carboxylic acid ethyl ester ("Drug 6"); [2R,4S]4-[acetyl-(3,5-bis-trifluoromethyl-benzyl)-amino]-2-ethyl-6-trifluoromethyl-3,4-dihydro-2H-quinoline-1-carboxylic acid isopropyl ester ("Drug 7"); [2S,4S]4-[(3,5-bis-trifluoromethyl-benzyl)-methoxycarbonyl-amino]-2-cyclopropyl-6-trifluoromethyl-3,4-dihydro-2H-quinoline-1-carboxylic acid isopropyl ester ("Drug 8"); [3S,5S]2 cyclopentyl-4-(4-fluoro-phenyl)-3-[fluoro-(4-trifluoromethyl-phenyl)-methyl]-7,7-dimethyl-5,6,7,8-tetrahydro-quinolin-5-ol ("Drug 9"). All of these compounds have a solubility in water of less than 1 μg/ml, with Clog P values ranging from 5.5 to 8.3. To prepare Examples 30-41, dispersions comprising 10 wt % drug and 90 wt % polymer were made by mixing each drug in the solvent acetone together with polymer to form a solution. Dispersions with HPMCAS-MF and CAP were prepared for each drug. The solutions comprised 0.05 wt % drug, 0.45 wt % polymer, and 99.5 wt % acetone. Each solution was pumped into a "mini" spray-dryer apparatus via a syringe pump at a rate of 1.3 mL/min. The polymer solution was atomized through a spray nozzle using a heated stream of nitrogen. The resulting solid spray-dried dispersion was collected on a filter paper at a yield of about 65%. The preparation parameters are summarized in Table 15.

Controls 6-11

The comparative compositions of Controls 6-11 consisted of 1.5 mg of the crystalline form of each of Drugs 4-9 alone.

TABLE 15

| Example | Drug No. | Drug Mass (mg) | Aqueous-Soluble Polymer* | Polymer Mass (mg) | Solvent | Solvent Mass (g) | Spray Apparatus |
|---|---|---|---|---|---|---|---|
| 30 | 4 | 5 | HPMCAS-MF | 45 | acetone | 10 | mini |
| 31 | 4 | 5 | CAP | 45 | acetone | 10 | mini |
| 32 | 5 | 5 | HPMCAS-MF | 45 | acetone | 10 | mini |
| 23 | 5 | 5 | CAP | 45 | acetone | 10 | mini |
| 34 | 6 | 5 | HPMCAS-MF | 45 | acetone | 10 | mini |
| 35 | 6 | 5 | CAP | 45 | acetone | 10 | mini |
| 36 | 7 | 5 | HPMCAS-MF | 45 | acetone | 10 | mini |
| 37 | 7 | 5 | CAP | 45 | acetone | 10 | mini |
| 38 | 8 | 5 | HPMCAS-MF | 45 | acetone | 10 | mini |
| 39 | 8 | 5 | CAP | 45 | acetone | 10 | mini |
| 40 | 9 | 5 | HPMCAS-MF | 45 | acetone | 10 | mini |
| 41 | 9 | 5 | CAP | 45 | acetone | 10 | mini |

*Polymer designations: HPMCAS = hydroxypropyl methyl cellulose acetate succinate, CAP = cellulose acetate phthalate.

Example 42

The spray-dried dispersions of Examples 30-41 were evaluated in an in vitro dissolution test using a microcentrifuge method. In this method, 15 mg of each SDD was added to a 2-mL microcentrifuge tube. The tube was placed in a 37° C. sonicating bath, and 1.5 mL of a phosphate-buffered saline (PBS) solution at pH 6.5 and 290 mOsm/kg) was added, resulting in a $TC_{max}$ of 1000 μg/mL. The samples were quickly mixed using a combination of vortex mixer and sonication for about 90 seconds. The samples were centrifuged at 13,000 G at 37° C. for 1 minute. The resulting supernatant solution was then sampled and diluted 1:6 (by volume) with methanol and then analyzed by HPLC. The tubes were then mixed on the vortex mixer and allowed to stand undisturbed at 37° C. until the next sample. Samples were collected at 4, 10, 20, 40, and 90 minutes. Data are included in Table 16.

For Controls 6-11, an in vitro dissolution test was performed using the procedure described above, except that 1.5 mg of non-crystalline drug was placed in a microcentrifuge tube and mixed with 1.5 mL of PBS. The test results are included in Table 16.

TABLE 16

| Example | Time (min) | Concentration (μg/mL) | AUC (min · μg/mL) |
|---|---|---|---|
| 30 | 0 | 0 | 0 |
|  | 4 | 999 | 2,000 |
|  | 10 | 836 | 7,500 |
|  | 20 | 729 | 15,300 |
|  | 60 | 571 | 28,300 |
|  | 90 | 471 | 54,400 |
| 31 | 0 | 0 | 0 |
|  | 4 | 591 | 1,200 |
|  | 10 | 599 | 4,800 |
|  | 20 | 557 | 10,500 |
|  | 40 | 500 | 21,100 |
|  | 90 | 427 | 44,300 |
| 32 | 0 | 0 | 0 |
|  | 4 | 1091 | 2,200 |
|  | 10 | 1079 | 8,700 |
|  | 20 | 1061 | 19,400 |
|  | 40 | 1033 | 40,300 |
|  | 90 | 985 | 90,800 |
| 33 | 0 | 0 | 0 |
|  | 4 | 836 | 1,700 |
|  | 10 | 965 | 7,100 |
|  | 20 | 971 | 16,800 |
|  | 40 | 973 | 36,200 |
|  | 90 | 943 | 84,100 |
| 34 | 0 | 0 | 0 |
|  | 4 | 852 | 1,700 |
|  | 10 | 890 | 6,900 |
|  | 20 | 896 | 15,900 |
|  | 40 | 852 | 33,300 |
|  | 90 | 781 | 74,200 |
| 35 | 0 | 0 | 0 |
|  | 4 | 536 | 1,100 |
|  | 10 | 623 | 4,600 |
|  | 20 | 650 | 10,900 |
|  | 40 | 713 | 24,500 |
|  | 90 | 610 | 57,600 |
| 36 | 4 | 0 | 0 |
|  | 10 | 947 | 1,900 |
|  | 20 | 912 | 7,500 |
|  | 40 | 876 | 16,400 |
|  | 90 | 832 | 33,500 |
|  | 1200 | 783 | 73,900 |
| 37 | 0 | 0 | 0 |
|  | 4 | 262 | 500 |
|  | 10 | 559 | 3,000 |
|  | 20 | 638 | 9,000 |
|  | 40 | 643 | 21,800 |
|  | 90 | 590 | 52,600 |
| 38 | 0 | 0 | 0 |
|  | 4 | 974 | 1,900 |
|  | 10 | 965 | 7,800 |
|  | 20 | 933 | 17,300 |
|  | 40 | 935 | 35,900 |
|  | 90 | 969 | 83,500 |
| 39 | 0 | 0 | 0 |
|  | 4 | 705 | 1,400 |
|  | 10 | 811 | 6,000 |
|  | 20 | 860 | 14,300 |
|  | 40 | 952 | 32,400 |
|  | 90 | 1003 | 81,300 |
| 40 | 0 | 0 | 0 |
|  | 4 | 224 | 400 |
|  | 10 | 503 | 2,600 |

TABLE 16-continued

| Example | Time (min) | Concentration (µg/mL) | AUC (min·µg/mL) |
|---|---|---|---|
| | 20 | 633 | 8,300 |
| | 40 | 699 | 21,600 |
| | 90 | 785 | 58,700 |
| 41 | 0 | 0 | 0 |
| | 4 | 196 | 400 |
| | 10 | 342 | 2,000 |
| | 20 | 527 | 6,400 |
| | 40 | 520 | 16,800 |
| | 90 | 596 | 44,700 |
| Control 6 | 0 | 0 | 0 |
| | 4 | <1 | <4 |
| | 10 | <1 | <10 |
| | 20 | <1 | <20 |
| | 40 | <1 | <40 |
| | 90 | <1 | <90 |
| Control 7 | 0 | 0 | 0 |
| | 4 | <1 | <4 |
| | 10 | <1 | <10 |
| | 20 | <1 | <20 |
| | 40 | <1 | <40 |
| | 90 | <1 | <90 |
| Control 8 | 0 | 0 | 0 |
| | 4 | <1 | <4 |
| | 10 | <1 | <10 |
| | 20 | <1 | <20 |
| | 40 | <1 | <40 |
| | 90 | <1 | <90 |
| Control 9 | 0 | 0 | 0 |
| | 4 | <1 | <4 |
| | 10 | <1 | <10 |
| | 20 | <1 | <20 |
| | 40 | <1 | <40 |
| | 90 | — | — |
| Control 10 | 0 | 0 | 0 |
| | 4 | <1 | <4 |
| | 10 | <1 | <10 |
| | 20 | <1 | <20 |
| | 40 | <1 | <40 |
| | 90 | <1 | <90 |
| Control 11 | 0 | 0 | 0 |
| | 4 | <1 | <4 |
| | 10 | <1 | <10 |
| | 20 | <1 | <20 |
| | 40 | <1 | <40 |
| | 90 | <1 | <90 |

The results, summarized in Table 17, show that the dissolution results for the compositions of Examples 30 through 41 were much better than that of each crystalline drug alone, providing $C_{max,90}$ values that were greater than 596- to 1091-fold that of each respective crystalline drug (Controls 6-11), and $AUC_{90}$ values that were greater than 490- to 1,000-fold that of each respective crystalline drug.

TABLE 17

| Example | Drug No. | Aqueous-Soluble Polymer* | Conc. of Drug in Polymer (wt %) | $C_{max,90}$ (µg/mL) | $AUC_{90}$ (min·µg/mL) |
|---|---|---|---|---|---|
| 30 | 4 | HPMCAS-MF | 10 | 999 | 54,400 |
| 31 | 4 | CAP | 10 | 599 | 44,300 |
| 32 | 5 | HPMCAS-MF | 10 | 1091 | 90,800 |
| 33 | 5 | CAP | 10 | 973 | 84,100 |
| 34 | 6 | HPMCAS-MF | 10 | 896 | 74,200 |
| 35 | 6 | CAP | 10 | 713 | 57,600 |
| 36 | 7 | HPMCAS-MF | 10 | 947 | 73,900 |
| 37 | 7 | CAP | 10 | 643 | 52,600 |
| 38 | 8 | HPMCAS-MF | 10 | 974 | 83,500 |
| 39 | 8 | CAP | 10 | 1003 | 81,300 |
| 40 | 9 | HPMCAS-MF | 10 | 785 | 58,700 |
| 41 | 9 | CAP | 10 | 596 | 44,700 |
| Control 6 | 4 | None | — | <1 | <90 |
| Control 7 | 5 | None | — | <1 | <90 |
| Control 8 | 6 | None | — | <1 | <90 |
| Control 9 | 7 | None | — | <1 | <90 |
| Control 10 | 8 | None | — | <1 | <90 |
| Control 11 | 9 | None | — | <1 | <90 |

*Polymer designations: HPMCAS = hydroxypropyl methyl cellulose acetate succinate, CAP = cellulose acetate phthalate.

The terms and expressions which have been employed in the foregoing specification are used therein as terms of description and not of limitation, and there is no intention, in the use of such terms and expressions, of excluding equivalents of the features shown and described or portions thereof, it being recognized that the scope of the invention is defined and limited only by the claims which follow.

The invention claimed is:

1. A pharmaceutical composition comprising a solid amorphous dispersion of a cholesteryl ester transfer protein inhibitor and a concentration-enhancing polymer, at least 60 wt % of said cholesteryl ester transfer protein inhibitor being non-crystalline,
   wherein
   said cholesteryl ester transfer protein inhibitor has a Clog P greater than 4 and a solubility in aqueous solution in the absence of said concentration-enhancing polymer of less than 10 µg/ml at any pH of from 1 to 8,
   said solid amorphous dispersion comprises particles comprising both said cholesteryl ester transfer protein inhibitor and said concentration-enhancing polymer, and
   said solid amorphous dispersion has a glass transition temperature that is different than the glass transition temperature of the pure amorphous cholesteryl ester transfer protein inhibitor alone and different than the glass transition temperature of the pure concentration-enhancing polymer alone.

2. The composition of claim 1 wherein said solid amorphous dispersion is substantially homogeneous so that less than 20 wt % of said cholesteryl ester transfer protein inhibitor is present in relatively pure amorphous domains in said solid amorphous dispersion.

3. The composition of claim 2 wherein said solid amorphous dispersion comprises a solid solution of said cholesteryl ester transfer protein inhibitor in said concentration-enhancing polymer.

4. The composition of claim 2 wherein said solid amorphous dispersion has a single glass-transition temperature.

5. The composition of claim 1 wherein said cholesteryl ester transfer protein inhibitor has a Clog P of at least 5.0.

6. The composition of claim 1 wherein said cholesteryl ester transfer protein inhibitor has a Clog P of at least 5.5.

7. The composition of claim 1 wherein the melting point of said cholesteryl ester transfer protein inhibitor is about 150° C. or less.

8. The composition of any one of claims 1 to 7 wherein said composition provides a relative oral bioavailability that is at least about 4 relative to a control composition comprising an equivalent amount of said cholesteryl ester transfer protein inhibitor and free from said polymer.

9. The composition of any one of claims 1 to 7 wherein said concentration-enhancing polymer is selected from the group consisting of hydroxypropyl methyl cellulose acetate succinate (HPMCAS), hydroxypropyl methyl cellulose phthalate (HPMCP), cellulose acetate phthalate (CAP), cellulose acetate trimellitate (CAT), methyl cellulose acetate phthalate, hydroxypropyl cellulose acetate phthalate, cellulose acetate terephthalate and cellulose acetate isophthalate.

10. A pharmaceutical composition comprising a solid amorphous dispersion of a cholesteryl ester transfer protein inhibitor and a concentration-enhancing polymer, wherein said cholesteryl ester transfer protein inhibitor has the structure of formula XIII, wherein

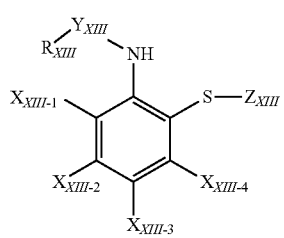

Formula XIII or pharmaceutically acceptable salts, enantiomers, stereoisomers, hydrates, or solvates of said compounds, in which $R_{XIII}$ is a straight chain or branched $C_{1-10}$ alkyl; straight chain or branched $C_{2-10}$ alkenyl; halogenated $C_{1-4}$ lower alkyl; $C_{3-10}$ cycloalkyl that may be substituted; $C_{5-8}$ cycloalkenyl that may be substituted; $C_{3-10}$ cycloalkyl $C_{1-10}$ alkyl that may be substituted; aryl that may be substituted; aralkyl that may be substituted; or a 5- or 6-membered heterocyclic group having 1 to 3 nitrogen atoms, oxygen atoms or sulfur atoms that may be substituted, $X_{XIII-1}$, $X_{XIII-2}$, $X_{XIII-3}$, $X_{XIII-4}$ may be the same or different and are a hydrogen atom; halogen atom; $C_{1-4}$ lower alkyl; halogenated $C_{1-4}$ lower alkyl; $C_{1-4}$ lower alkoxy; cyano group; nitro group; acyl; or aryl, respectively;

$Y_{XIII}$ is —CO—; or —SO$_2$—; and $Z_{XIII}$ is a hydrogen atom; or mercapto protective group.

11. The composition of claim 10 wherein said cholesteryl ester transfer protein inhibitor is selected from the group consisting of N,N'-(dithiodi-2,1-phenylene)bis[2,2-dimethyl-propanamide]; N,N'-(dithiodi-2,1-phenylene)bis[1-methyl-cyclohexanecarboxamide]; N,N'-(dithiodi-2,1-phenylene)bis[1-(3-methylbutyl)-cyclopentanecarboxamide]; N,N'-(dithiodi-2,1-phenylene)bis[1-(3-methylbutyl)-cyclohexanecarboxamide]; N,N'-(dithiodi-2,1-phenylene)bis[1-(2-ethylbutyl)-cyclohexanecarboxamide]; N,N'-(dithiodi-2,1-phenylene)bis-tricyclo[3.3.1.1$^{3,7}$]decane-1-carboxamide; propanethioic acid, 2-methyl-,S-[2[[[1-(2-ethylbutyl)cyclohexyl]carbonyl]amino]phenyl]ester; propanethioic acid, 2,2-dimethyl-, S-[2-[[[1-(2-ethylbutyl)cyclohexyl]carbonyl]amino]phenyl]ester; and ethanethioic acid, S-[2-[[[1-(2-ethylbutyl)cyclohexyl]carbonyl]amino]phenyl]ester.

12. The composition of claim 10 wherein said cholesteryl ester transfer protein inhibitor is propanethioic acid, 2-methyl-,S-[2[[[1-(2-ethylbutyl)cyclohexyl]carbonyl]amino] phenyl]ester.

13. The composition of any one of claims 10 to 12 wherein said solid amorphous dispersion is substantially homogeneous.

14. The composition of any one of claims 10 to 12 wherein the amount of said cholesteryl ester transfer protein inhibitor in crystalline form does not exceed 10 wt %.

15. The composition of any one of claims 10 to 12 wherein said concentration-enhancing polymer is selected from the group consisting of hydroxypropyl methyl cellulose acetate succinate (HPMCAS), hydroxypropyl methyl cellulose phthalate (HPMCP), cellulose acetate phthalate (CAP), cellulose acetate trimellitate (CAT), methyl cellulose acetate phthalate, hydroxypropyl cellulose acetate phthalate, cellulose acetate terephthalate and cellulose acetate isophthalate.

* * * * *